(12) United States Patent
Stout et al.

(10) Patent No.: US 7,122,181 B2
(45) Date of Patent: Oct. 17, 2006

(54) LENTIVIRAL VECTOR-MEDIATED GENE TRANSFER AND USES THEREOF

(75) Inventors: J. Timothy Stout, Portland, OR (US); Binoy Appukuttan, Portland, OR (US)

(73) Assignee: Research Development Foundation, Carson City, NV (US)

(*) Notice: Subject to any disclaimer, the term of this patent is extended or adjusted under 35 U.S.C. 154(b) by 285 days.

(21) Appl. No.: 10/245,050

(22) Filed: Sep. 17, 2002

(65) Prior Publication Data

US 2003/0082159 A1 May 1, 2003

Related U.S. Application Data

(63) Continuation-in-part of application No. 10/025,264, filed on Dec. 19, 2001, now abandoned.

(60) Provisional application No. 60/256,701, filed on Dec. 19, 2000.

(51) Int. Cl.
| | |
|---|---|
| A01N 63/00 | (2006.01) |
| A01N 43/04 | (2006.01) |
| C12N 5/00 | (2006.01) |
| C12N 15/00 | (2006.01) |
| C12N 15/63 | (2006.01) |

(52) U.S. Cl. ............... 424/93.2; 424/93.1; 424/93.6; 435/69.1; 435/320.1; 435/325; 435/455; 514/44

(58) Field of Classification Search ............. 424/93.1, 424/93.2, 93.6; 435/69.1, 320.1, 325, 455; 514/44
See application file for complete search history.

(56) References Cited

U.S. PATENT DOCUMENTS

| 5,969,120 A | 10/1999 | Fung .................. 536/23.1 |
| 6,004,798 A | 12/1999 | Anderson et al. ......... 435/235.1 |
| 2002/0114783 A1 | 8/2002 | Appukuttan et al. ....... 424/93.2 |
| 2002/0194630 A1 | 12/2002 | Manning, Jr. et al. .......... 800/8 |
| 2003/0045498 A1 | 3/2003 | Kovesdi et al. ............... 514/44 |
| 2003/0087859 A1 | 5/2003 | Kochanek et al. ............ 514/44 |

FOREIGN PATENT DOCUMENTS

| WO | WO 02/24234 | 3/2002 |
| WO | WO 02/49677 | 6/2002 |

OTHER PUBLICATIONS

Juengst BMJ, 326:1410–11, 2003.*
Brown et al Blood 100(4) :133–1140, 2002.*
Rosenberg et al, Science 287:1751, 2000.*
Friedmann, Science 287(5461):2163–5, 2000.*
Touchette, Nat. Med. 2(1) 7–8, 1996.*
Hamdi et al, Frontiers in Bioscience 8:e305–314, 2003.*
Borras, Exp. Eye Res. 76:643–652, 2003.*
McFarland et al Expert Opin. Biol. Ther 4(7):1053–1058, 2004.*
Murata, T. et al. *The Possibility of Gene Therapy for the Treatment of Choroidal Neovascularization: Ophthalmology*, Jul. 2000, vol. 107, No. 7, pp. 1364–1373.
Sakamoto, T. et al. *Inhibition of Experimental Proliferative Vitretinopathy by Retroviral Vector–mediated Transfer of Suicide Gene: Ophthalmology*, Oct. 1995, vol. 102, No. 10, pp. 1417–1424.
Acland et al., "Gene therapy restores vision in a canine model of childhood blindness," *Nature Genetics*, 28:92–95, 2001.
Akimoto et al., "Growth inhibition of cultured human tenon's fibroblastic cells by targeting the E2F transcription factor," *Exp. Eye Res.*, 67:395–401, 1998.
Ali et al., "Gene transfer into the mouse retina mediated by an adeno–associated viral vector," *Human Molecular Genetics*, 5(5):591–594, 1996.
Audo et al., "p21 and p35 gene therapy in a mouse model of retinoblastoma," ARVO Annual Meeting, vol. 2003, Abstract No. 1585, May 5, 2003.
Auricchio et al., "Inhibition of retinal neovascularization by intraocular viral–mediated delivery of anti–angiogenic agents," *Molecular Therapy*, 6(4):490–494, 2002.
Benihoud et al., "Efficient, repeated adenovirus–mediated gene transfer in mice lacking both tumor necrosis factor alpha and lymphotoxin α," *Journal of Virology*, 72(12):9514–9525, 1998.
Chen et al., "Stability of retinoblastoma gene expression determines the tumorigenicity of reconstituted retinoblastoma cells," *Cell Growth and Differentiation*, 3:119–125, 1992.
Cheon et al., "Adenovirus–mediated suicide–gene therapy using the herpes simplex virus thymidine kinase gene in cell and animal models of human prostate cancer: changes in tumour cells proliferative activity," *BJU International*, 85:759–766, 2000.
Claudio et al., "Adenoviral RB2/p130 gene transfer inhibits smooth muscle cell proliferation and prevents restenosis after angioplasty," *Circulation Research*, 85:1032–1039, 1999.
Dejneka and Bennett, "Gene therapy and retinitis pigmentosa: advances and future challenges," *BioEssays*, 23:662–668, 2001.
Dong et al., "Suppression of angiogenesis, tumorigenicity, and metastasis by human prostate cancer cells engineered to produce interferon–β,"*Cancer Res.*, 59:872–879, 1999.
Farrar et al., "On the genetics of retinitis pigmentosa and on mutation–independent approaches to therapeutic intervention," *The EMBO J.*, 21(5):857–864, 2002.

(Continued)

*Primary Examiner*—Sumesh Kaushal
(74) *Attorney, Agent, or Firm*—Fulbright & Jaworski LLP

(57) ABSTRACT

The present invention provides lentiviral vectors that are useful in human gene therapy for inherited or acquired proliferative ocular disease. It furnishes methods to exploit the ability of lentiviral vectors to transduce both mitotically active and inactive cells so that eye diseases may be treated.

26 Claims, 44 Drawing Sheets

OTHER PUBLICATIONS

Galileo et al., "Stable and efficient gene transfer into the mutant retinal pigment epithelial cells of the Mitf mouse using a lentiviral vector," *Current Eye Research*, 18(2):135–142, 1999.

Gasperini et al., "Gene expression and production of the monokine induced by IFN–gamma (MIG), IFN–inducible T cell alpha chemoattractant (I–TAC), and IFN–gamma–inducible protein–10 (IP–10) chemokines by human neutrophils," *J. Immunol.*, 162:4928–4937, 1999.

Green et al., "Two animal models of retinal degeneration are rescued by recombinant adeno–associated virus–mediated production of FGF–5 and FGF–18," *Molecular Therapy*, 3(4):507–515, 2001.

Harvey et al., "Intravitreal injection of adeno–associated viral vectors results in the transduction of different types of retinal neurons in neonatal and adult rats: a comparison with lentiviral vectors," *Molecular and Cellular Neuroscience*, 21:141–157, 2002.

Holmgren et al., "p53 induces angiogenesis–restricted dormancy in a mouse fibrosarcoma," *Oncogene*, 17:819–824, 1998.

Ikuno et al., "Attenuation of experimental proliferative vitreoretinopathy by inhibiting the platelet–derived growth factor receptor," *Investigative Ophthalmology & Visual Science*, 41(10):3107–3116, 2000.

Jomary et al., "Rescue of photoreceptor function by AAV–mediated gene transfer in a mouse model of inherited retinal degeneration," *Gene Therapy*, 4:683–690, 1997.

Kagawa et al., "Overexpression of the $p21^{sdi1}$ gene induced senescence–like state in human cancer cells: implication for senescence–directed molecular therapy for cancer," *Cell Death and Differentiation*, 6:765–772, 1999.

Kobayashi et al., "Novel gene therapy for rheumatoid arthritis by FADD gene transfer: induction of apoptosis of rheumatoid synoviocytes but not chondrocytes," *Gene Therapy*, 7:527–533, 2000.

Kreppel et al., "Long–term transgene expression in the RPE after gene transfer with a high–capacity adenoviral vector," *Investigative Ophthalmology & Visual Science*, 43(6):1965–1970, 2002.

Loewen et al., "Genetic modification of human trabecular meshwork with lentiviral vectors," *Human Gene Therapy*, 12:2109–2119, 2001.

Lotery et al., "Gene transfer to the nonhuman primate retina with recombinant feline immunodeficiency virus vectors," *Human Gene Therapy*, 13:689–696, 2002.

Miyoshi et al., "Stable and efficient gene transfer into the retina using an HIV–based lentiviral vector," *Proc. Natl. Acad. Sci., USA*, 94:10319–10323, 1997.

Mori et al., "AAA–mediated gene transfer of pigment epithelium–derived factor inhibits choroidal neovascularization," *Investigative Ophthalmology & Visual Science*, 43(6):1994–2000, 2002.

Riley et al., "Prospects for tumor suppressor gene therapy: RB as an example," *Tumor Suppressing Viruses, Genes and Drugs*, Maruta Publisher: Academic Press, San Diego, CA, 97–122, 2002.

Sakamoto et al., "Gene targeting to the retina," *Advanced Drug Delivery Reviews*, 52:93–102, 2001.

Schechner et al., "In vivo formation of complex microvessels lined by human endothelial cells in an immunodeficient mouse," *Proc. Natl. Acad. Sci., USA*, 97(16):9191–9196, 2000.

Scherr et al., "Effective reversal of a transformed phenotype by retrovirus–mediated transfer of a ribozyme directed against mutant N–ras," *Gene Therapy*, 5:1227–1234, 1998.

Schwerzenberger, "IL–17 stimulates granulopoiesis in mice: use of an alternate, novel gene therapy–derived method for in vivo evaluation of cytokines," *The Journal of Immunology*, 161:6383–6389, 1998.

Shirakawa et al., "p53 adenoviral vector (AD–CMV–p53 induced prostatic growth inhibition of primary cultures of human prostate and an experimental rat model," *The Journal of Gene Medicine*, 2:426–432, 2000.

Szekely et al., "RB–reconstituted human retinoblastoma cells form RB–positive intraocular and intracerebral but not subcutaneous tumors in scid mice," *Int. J. Cancer*, 61:683–691, 1995.

Takahashi et al., "Rescue from photoreceptor degeneration in the rd mouse by human immunodeficiency virus vector–mediated gene transfer," *Journal of Virology*, 73(9):7812–7816, 1999.

Wang et al., "Efficient and sustained transgene expression in human corneal cells mediated by a lentiviral vector," *Gene Therapy*, 7:169–200, 2000.

Wen et al., "Characterization of adenovirus p21 gene transfer, biodistribution, and immune response after local ocular delivery in New Zealand white rabbits," *Ex Eye Res.*, 77:355–365, 2003.

Yang et al., "Expression of a recombinant human RGR opsin in Lentivirus–transduced cultured cells," *Molecular Vision*, 6:237–242, 2000.

\* cited by examiner

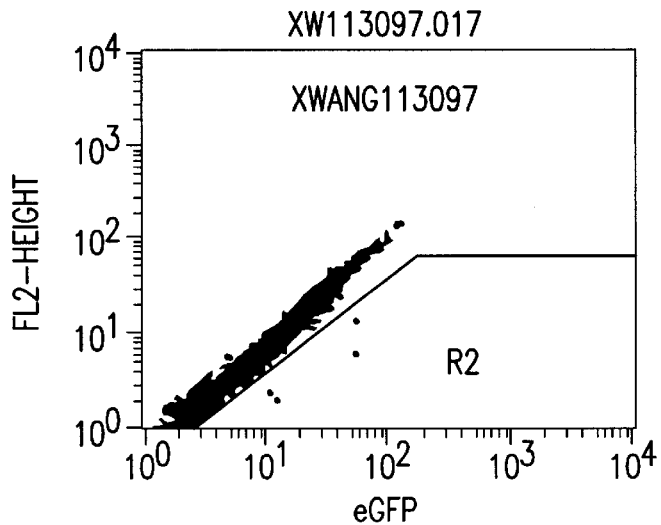
FIG.3B
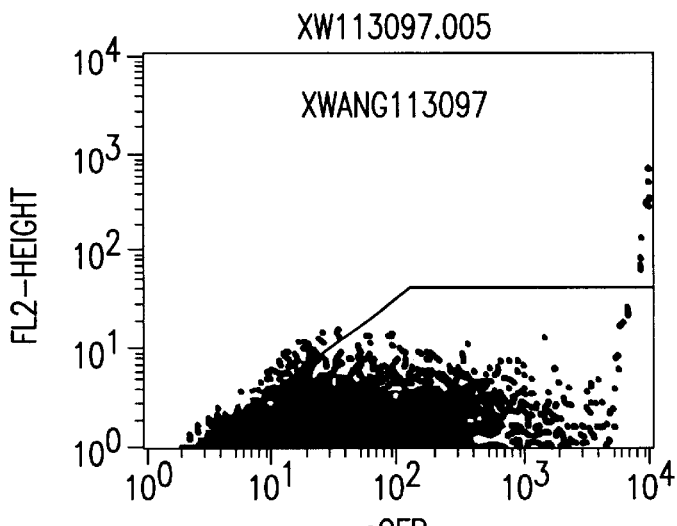
FIG.3C
| FILE: XW113097.005 | | GATE: G1 | |
|---|---|---|---|
| REGION | EVENTS | % GATED | % TOTAL |
| R1 | 6588 | 100.00 | 65.88 |
| R2 | 6500 | 98.66 | 65.00 |
FIG.3D

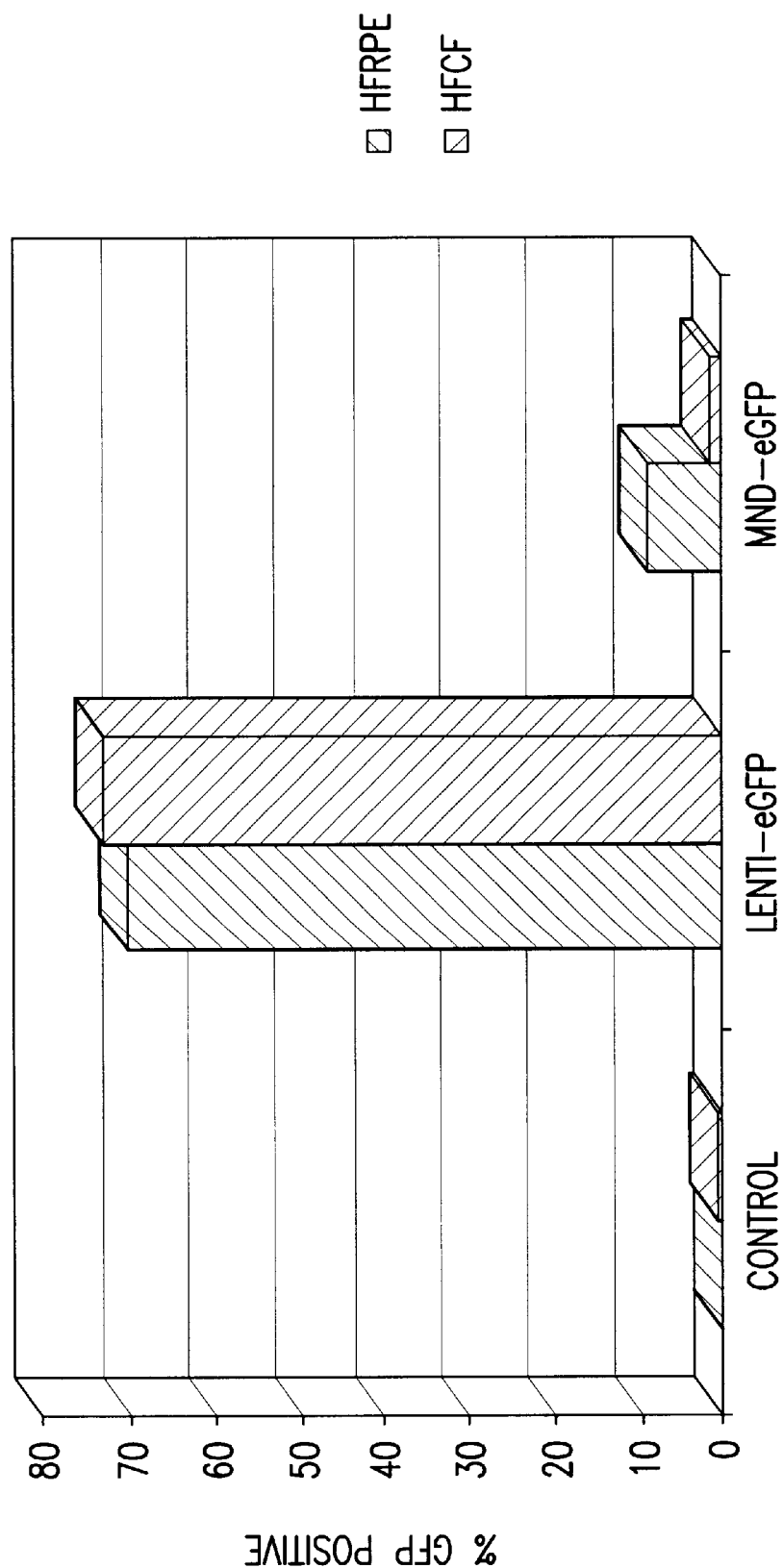

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<221> NAME/KEY: primer_bind
<223> OTHER INFORMATION: forward primer for Endostatin-Kringle-5 fusion
      cDNA

<400> SEQUENCE: 1
ctgagggatc cggcgaagga g                                           21

<210> SEQ ID NO 2
<211> LENGTH: 27
<212> TYPE: DNA
<213> ORGANISM: Artificial Sequence
<220> FEATURE:
<221> NAME/KEY: primer_bind
<223> OTHER INFORMATION: reverse primer for Endostatin-Kringle-5 fusion
      cDNA

<400> SEQUENCE: 2
caatgtatcg gatcctgtcg agctagc                                     27

<210> SEQ ID NO 3
<211> LENGTH: 8
<212> TYPE: PRT
<213> ORGANISM: Unknown
<220> FEATURE:
<221> NAME/KEY: CHAIN
<223> OTHER INFORMATION: elastin linker motif

<400> SEQUENCE: 3

Val Pro Gly Val Gly Thr Ala Ser
                  5           8

<210> SEQ ID NO 4
<211> LENGTH: 25
<212> TYPE: DNA
<213> ORGANISM: Artificial Sequence
<220> FEATURE:
<221> NAME/KEY: primer_bind
```

-continued

```
<223> OTHER INFORMATION: forward primer for Endostatin-Kringle-5
      fusion transcript

<400> SEQUENCE: 4
tctgagggtc cgctgaagcc cgggg                                              25

<210> SEQ ID NO 5
<211> LENGTH: 18
<212> TYPE: DNA
<213> ORGANISM: Artificial Sequence
<220> FEATURE:
<221> NAME/KEY: primer_bind
<223> OTHER INFORMATION: reverse primer for Endostatin-Kringle-5
      fusion transcript

<400> SEQUENCE: 5
caaatgaagg ggccgcac                                                      18
```

LENTIVIRAL VECTOR-MEDIATED GENE TRANSFER AND USES THEREOF

CROSS-REFERENCE TO RELATED APPLICATION

This is a continuation-in-part application of U.S. Ser. No. 10/025,264, filed Dec. 19, 2001 now abandoned, which claims benefit of provisional patent application U.S. Ser. No. 60/256,701, filed Dec. 19, 2000, now abandoned.

BACKGROUND OF THE INVENTION

1. Field of the Invention

The present invention relates generally to the fields of gene delivery vectors and gene therapy. More specifically, the present invention relates to lentiviral vectors useful in human gene therapy for inherited and proliferative ocular disease.

2. Description of the Related Art

One of the most common causes of human blindness is abnormal, intraocular cellular proliferation that often results in a loss of clarity of the visual axis or in a separation of the retina from the retinal pigment epithelium due to tractional forces applied directly to the retinal surface. Proliferative retinal detachment, whether it is related to proliferative diabetic disease, retinopathy of prematurity, proliferative vitreoretinopathy, or neovascular age-related muscular degeneration, ultimately will result in permanent loss of vision if left untreated.

The abnormal proliferation of new blood vessels within the eye, ocular neovascularization, is the most common cause of permanent blindness in developed countries. Three diseases are associated with the vast majority of all cases of intraocular neovascularization, namely diabetes, retinopathy of prematurity and age-related muscular degeneration. While these three clinical entities are distinct and affect different groups of patients, they share a final common pathway that involves uncontrolled division of endothelial cells leading to formation of new blood vessels that ultimately compromise retinal function. Ocular proliferative diseases affect 7% of the U.S. population and leads to annually 25,000 new cases of blindness in the United States. For people over 65 years old in the United States, 30% are affected by the diseases.

Proliferation of vascular endothelial cells within the retina initiates the process of proliferative diabetic retinopathy (PDR). If untreated, these endothelial cells continue to divide and eventually form fibrovascular membranes that extend along the inner surface of the retina or into the vitreous cavity. Contraction of the posterior vitreous surface results in traction at the sites of vitreo-fibrovascular adhesions and ultimately detaches the retina. Approximately 50% of Type 1 diabetics will develop PDR within 20 years of the diagnosis of diabetes, whereas 10% of patients with Type 2 disease will evidence PDR within a similar timeframe.

Blood vessels usually develop by one of two processes: vasculogenesis or angiogenesis. During vasculogenesis, a primitive network of capillaries is established during embryogenesis by the maturation of multipotential mesenchymal progenitors. In contrast, angiogenesis refers to a remodeling process involving pre-existing vessels. In angiogenesis new vascular buds emanate from older, established vessels and invade the surrounding tissue. In the retina, once the normal vascular network is established, the remodeling of this network is largely under the influence of tissue oxygen concentration. Hypoxia (oxygen paucity) stimulates angiogenesis. It is this process which results in blindness in millions of diabetics, premature infants or the aged in our society.

Current treatments for intraocular neovascular diseases are invasive and destructive. The treatments frequently require intraocular surgery that is associated with the death of some tissues. Thus there is a need for new approaches to treat these diseases, and it is of interest to determine whether genes that modulate angiogenesis can be introduced into the eye to control the proliferative diseases. Currently it is difficult to perform gene transduction in mammalian cells with great degree of effectiveness. Results seen with traditional vectors such as adenoviral vectors, liposomes and dendrimer-based reagents are quite transient. It is also problematic to introduce these vectors into the eye without induction of a strong inflammatory response.

In order to mediate gene transfer to cells and tissues of the eye, the ideal gene delivery vector should have broad tropism and be able to transduce quiescent cells. The vector also needs to maintain sustained and robust transgene expression for the treatment of chronic diseases. Presently, there is a lack of means of transducing terminally differentiated or proliferating human cells within or derived from the eye. The present invention fulfills this long-standing need and desire in the art.

SUMMARY OF THE INVENTION

It is an object of the present invention to develop lentiviral vectors and methods of using these vectors in human gene therapy for inherited and proliferative ocular diseases. The usefulness of lentiviral vectors is described for the transduction of human retinal, corneal, vascular endothelial, proliferative vitreoretinopathic and retinal pigment epithelial cells.

The potential of suppressing intraocular cell division by a lentiviral-delivered constitutively active (mutant or variant) retinoblastoma (CA-rb) gene was demonstrated. Human ocular cells were tested in vitro and two models of intraocular proliferative disease (proliferative vitreoretinopathy and post-lens extraction posterior capsular opacification) were tested in vivo. Significant and long-lived inhibition of cell division in vitro was observed in many different cell types. Reduction in the severity of proliferative vitreoretinopathy and post-lens extraction posterior capsular opacification were observed in vivo.

It is further demonstrated that lentivirus-mediated transfer of genes known to be important in the development and inhibition of new blood vessel growth (angiogenesis) or pre-programmed cell death (apoptosis) could be useful in the treatment of pathologic ocular angiogenesis (e.g. diabetic retinopathy or "wet" age related macular degeneration) or pathologic cell death (e.g. "dry" age related macular degeneration). These genes were placed under the control of one of each of two separate strong promoters known to be active in human retinal, corneal and retinal pigment epithelial cells. Inhibition of corneal neovascularization was demonstrated in rabbit model. This inhibition of corneal neovascularization was shown to be associated with a prevention of graft failure in a model of corneal transplantation.

In addition, the lentiviral vectors of the present invention are useful in delivering genes known to be deficient in human patients with inherited eye disease. The transfer of these genes by the vectors disclosed herein forms the basis for useful therapies for patients with eye diseases.

The present invention is drawn to a method of inhibiting intraocular cellular proliferation in an individual having an ocular disease, comprising the step of: administering to said individual a pharmacologically effective dose of a lentiviral vector comprising a therapeutic gene that inhibits intraocular cellular proliferation.

The present invention is also drawn to a method of inhibiting intraocular neovascularization in an individual having an ocular disease, comprising the step of: administering to said individual a pharmacologically effective dose of a lentiviral vector comprising a therapeutic gene that inhibits intraocular neovascularization.

The present invention also provides a method of preventing neovascularization and corneal transplant failure by transducing corneal tissue ex vivo with a lentiviral vector comprising a therapeutic gene that inhibits neovascularization.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3B-3D shows fluorescent-activated cell sorting analysis of transduction efficiency. FIG. 3B, data outside of R2 gate reflects pre-transduction lack of fluorescence. FIG. 3C, demonstrates a post-transduction shift to >95% fluorescence, shown numerically in FIG. 3D.

FIG. 5 depicts expression stability in human retinal pigment epithelial cells. Cells were exposed to eGFP-containing lentiviral vectors and were subsequently maintained for at least 120 days in continuous culture.

FIG. 6 illustrates human fetal cell transgene expression. This graph depicts the highly efficient mode of transduction achieved with lentiviral vectors when compared with a non-lentiviral retroviral vector (MND-eGFP) or no viral vector (control) in human fetal cells.

FIG. 7A-B are schematic representations of the human cornea. FIG. 7C-D demonstrate human corneal endothelial transduction by an e-GFP-containing lentiviral vectors. Human corneal buttons, removed at the time of corneal transplant, were exposed to lentiviral particles. Descemet's membrane was subsequently removed and photographed in room light (FIG. 7D) and under conditions amenable to fluorescence detection (FIG. 7C). FIG. 7E-F demonstrate lentiviral-mediated eGFP gene transfer to human corneal epithelial cells. FIG. 7E is a light micrograph of a human cornea with an artifactually detached epithelial layer. Fluorescent microscopy FIG. 7F reveals epithelial fluorescence.

FIG. 34 shows the presence of eGFP in the corneal micropocket in treated animals.

FIG. 37 shows an inhibitory effect on neovascularization in animals treated with a Mig/IP10 lentiviral vector.

IP10 lentiviral vector. Note the lack of blood vessels into the cornea.

DETAILED DESCRIPTION OF THE INVENTION

Figure 1:
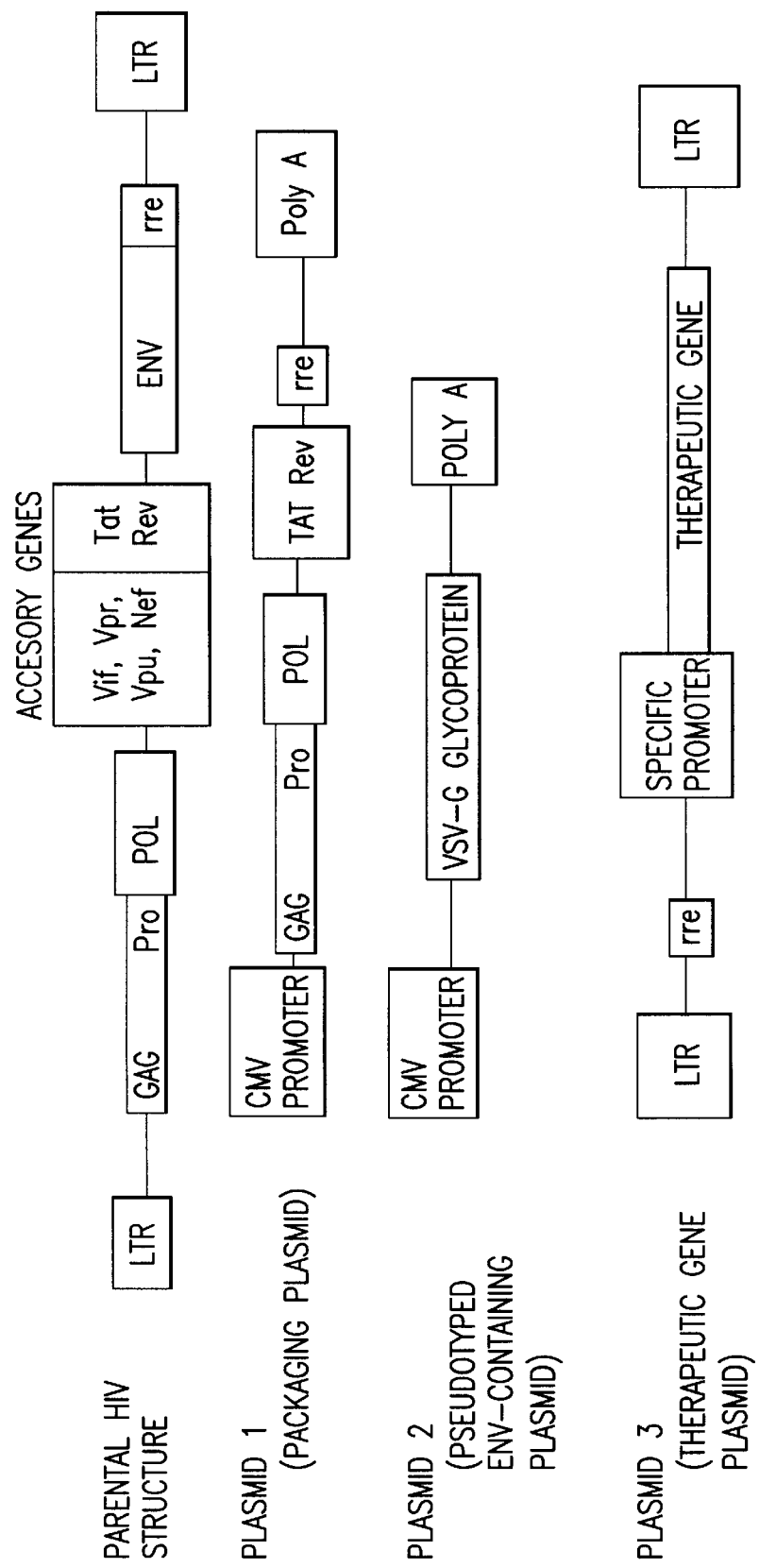
FIG. 1 depicts the vector provided by Dr. Inder Verma (Salk Institute, San Diego, Calif.). HIV: human immunodeficiency virus, LTR: long terminal repeat, GAG: HIV GAG gene, POL: HIV reverse transcriptase, ENV: HIV envelope gene, rre: rev-responsive element, CMV: cytomegalovirus, VSV: vesicular stomatitis virus, Poly A: polyadenylation signal, Specific promoter: any transcription-enhancing promoter can be place here so as to modulate spatial, temporal or quantitative aspects of therapeutic gene expression, Therapeutic gene: any gene with therapeutic potential can be placed here—examples include, but are not limited to, CA-rb, or genes whose deficiency results in disease.

Lentiviruses are slow viruses whose natural pathogenicity occurs over a period of months to years. This viral genus includes such retroviruses as HIV. These viruses are known to infect and transduce a wide variety of terminally differentiated, mitotically active or inactive human cell types. Their transduction efficiency is very high, even cell lines traditionally very refractory to gene transfer such as human retinal, corneal, trabecular, lenticular, retinal pigment epithelial, proliferative vitreoretinopathic and vascular endothelial cells can be transduced using this vector.

Upon infection with lentivirus, the viral genetic material integrates itself within the host genome. Thus, the viral genes become a permanent part of the host cell's genetic material and gene expression is constant for the life of the cell. Each cell transduced by a lentivirus will transmit the genetic information to its progeny. Under natural conditions of infection, lentivirus is an intraocular pathogen that does not induce inflammatory responses. Therefore, lentiviruses are good candidates as vectors in gene therapy for intraocular diseases. Previous work with this virus has demonstrated its successful use in transduction of both neural and retinal cells (Naldini et al., 1996; Miyoshi et al., 1997).

The present invention provides new lentiviral vectors that incorporated an IRES (internal ribosome entry site) element between two cloning sites. The IRES element allows mRNA-ribosome binding and protein synthesis. This backbone can accommodate two different expressible genes. A single message is produced in transduced cells; however, this message is functionally bi-cistronic and can drive the synthesis of two different proteins because of the IRES element. These two genes can be placed under the control of strong promoters such as CMV or HTLV promoters. Alternatively, one of skill in the art would readily employ other promoters known to be active in human retinal, corneal or retinal pigment epithelial cells. In this fashion each of the potentially therapeutic genes discussed below can be linked to a marker gene (e.g. the enhanced green fluorescent gene, the eGFP gene) so that transduced cells can simultaneously be marked and express the therapeutic gene of interest. Marked cells can easily be isolated in vitro and observed in vivo.

It would be apparent to one of skill in the art that other marker genes besides the enhanced green fluorescent protein gene could be incorporated into the lentiviral vector. A person having ordinary skill in this art would also readily be able to construct lentiviral vectors containing other therapeutic genes of interest in addition to those disclosed herein. Moreover, the lentiviral vector system disclosed herein can transfer genes known to be deficient in human patients with inherited eye disease or other diseases. The transfer of these genes to human ocular cells or other tissues by this system forms the basis for useful therapies for patients with various diseases.

The basic discovery detailed herein demonstrates that lentiviral vectors can transfer a variety of genes to modify abnormal intraocular proliferation and, hence, decrease the incidence of neovascular disease, retinal detachment or post-cataract extraction posterior capsular opacification. A number of therapeutic genes may be useful in clinical circumstances for in vivo inhibition of intraocular cell division. These genes include a variety of recently identified modulators for the process of new blood vessel growth (angiogenesis) or apoptosis. It is believe that genetic control of the expression of these modulators via lentivirus-mediated gene transfer would prove useful in the treatment of intraocular neovascular diseases such as age-related macular degeneration (AMD), retinopathy of prematurity (ROP) and proliferative diabetic retinopathy (PDR).

Vascular endothelial cells play a central role in both vasculogenesis and angiogenesis. These cells respond mitogenically (become active with regards to cell division or migration) to a variety of protein cytokines. For example, vascular endothelial growth factor (VEGF), angiogenin, angiopoietin-1 (Ang1) and angiotropin are cytokines that stimulate endothelial cell division, migration or cell-cell adhesion, and thus favor the process of angiogenesis. Endostatin, soluble (decoy) VEGF receptors (sflt), and thrombospondin are endogenous protein cytokines that appear to inhibit angiogenesis. The present invention demonstrates that many of these inhibitory proteins delivered by lentiviral vectors are useful in the treatment of intraocular neovascularization. Examples of genes that can be incorporated into the lentiviral vectors of the present invention include, but are not limited to, the following genes:

Tissue Inhibitors of Metalloproteinases

The tissue inhibitors of metalloproteinases (TIMPs) represent a family of ubiquitous proteins that are natural inhibitors of the matrix metalloproteinases (MMPs). Matrix metalloproteinases are a group of zinc-binding endopeptidases involved in connective tissue matrix remodeling and degradation of the extracellular matrix (ECM), an essential step in tumor invasion, angiogenesis, and metastasis. The matrix metalloproteinases each have different substrate specificities within the extracellular matrix and are important in its degradation. The analysis of matrix metalloproteinases in human mammary pathology showed that several matrix metalloproteinases were involved in degradation of the extracellular matrix: collagenase (MMP1) degrades fibrillar interstitial collagens; gelatinase (MMP2) mainly degrades type IV collagen; and stromelysin (MMP3) has a wider range of action.

There are four members of the TIMP family. TIMP-1 and TIMP-2 are capable of inhibiting tumor growth, invasion, and metastasis that has been related to matrix metalloproteinase inhibitory activity. Furthermore, both TIMP-1 and TIMP-2 are involved in the inhibition of angiogenesis. Unlike other members of the TIMP family, TIMP-3 is found only in the ECM and may function as a marker for terminal differentiation. Finally, TIMP-4 is thought to function in a tissue-specific fashion in extracellular matrix hemostasis (Gomez et al., 1997).

TIMP-1

Tissue inhibitor of metalloproteinase-1 (TIMP-1) is a 23kD protein that is also known as metalloproteinase inhibitor 1, fibroblast collagenase inhibitor, collagenase inhibitor and erythroid potentiating activity (EPA). The gene encoding TIMP-1 has been described by Docherty et al. (1985). TIMP-1 complexes with metalloproteinases (such as collagenases) and causes irreversible inactivation. The effects of TIMP-1 have been investigated in transgenic mouse models: one that overexpressed TIMP-1 in the liver, and another that expressed the viral oncogene Simian Virus 40/T antigen (TAg) leading to heritable development of hepatocellular carcinomas. In double transgenic experiments in which the TIMP-1 lines were crossed with the TAg transgenic line, overexpression of hepatic TIMP-1 was reported to block the development of TAg-induced hepatocellular carcinomas by inhibiting growth and angiogenesis (Martin et al., 1996).

TIMP-2

Tissue inhibitor of metalloproteinase-2 (TIMP-2) is a 24kD protein that is also known as metalloproteinase inhibitor 2. The gene encoding TIMP-2 has been described by Stetler-Stevenson et al. (1990). Metalloproteinase (MMP2) which plays a critical role in tumor invasion is complexed and inhibited by TIMP-2. Thus, TIMP-2 could be useful to inhibit cancer metastasis (Musso et al., 1997). When B16F10 murine melanoma cells, a highly invasive and metastatic cell line, were transfected with a plasmid coding for human TIMP-2 and injected subcutaneously in mice, TIMP-2 over-expression limited tumor growth and neoangiogenesis in vivo (Valente et al., 1998).

TIMP-3

Tissue inhibitor of metalloproteinase-3 (TIMP-3) is also known as metalloproteinase inhibitor 3. When breast carcinoma and malignant melanoma cell lines were transfected with TIMP-3 plasmids and injected subcutaneously into nude mice, suppression of tumor growth was observed (Anand-Apte et al., 1996). However, TIMP-3 overexpression had no effect on the growth of the two tumor cell lines in vitro. Thus, it was suggested that the TIMP-3 released to the adjacent extracellular matrix by tumor cells inhibited tumor growth by suppressing the release of growth factors sequestered in extracellular matrix, or by inhibiting angiogenesis (Anand-Apte et al., 1996).

TIMP-4

Tissue inhibitor of metalloproteinase-4 (TIMP-4) is also known as metalloproteinase inhibitor 4. The TIMP-4 gene and tissue localization have been described by Greene et al. (1996). Biochemical studies have shown that TIMP-4 binds human gelatinase A similar to that of TIMP-2 (Bigg et al., 1997). The effect of TIMP-4 modulation on the growth of human breast cancers in vivo was investigated by Wang et al. (1997). Overexpression of TIMP-4 was found to inhibit cell invasiveness in vitro, and tumor growth was significantly reduced following injection of nude mice with TIMP-4 tumor cell transfectants in vivo (Wang et al., 1997).

Endostatin, Angiostatin, PEX, Kringle-5 and Fusion Genes

J. Folkman and his colleagues (Boehm et al., 1997) showed that treatment of mice with Lewis lung carcinomas with the combination of endostatin+angiostatin proteins induced complete regression of the tumors, and that mice remained healthy for the rest of their life. This effect was obtained only after one cycle (25 days) of endostatin+angiostatin treatment, whereas endostatin alone required 6 cycles to induce tumor dormancy.

D. Hanahan and colleagues (Bergers et al., 1999) demonstrated a superior antitumoral effect of the combination of endostatin+angiostatin proteins in a mouse model for pancreatic islet carcinoma. Endostatin+angiostatin combination resulted in a significant regression of the tumors, whereas endostatin or angiostatin alone had no effect.

Endostatin XVIII

Endostatin, an angiogenesis inhibitor produced by hemangioendothelioma, was first identified by O'Reilly et al. (1997). Endostatin is a 20kD C-terminal fragment of collagen XVIII that specifically inhibits endothelial proliferation, and potently inhibits angiogenesis and tumor growth. In fact, primary tumors have been shown to regress to dormant microscopic lesions following the administration of recombinant endostatin (O'Reilly et al., 1997). Endostatin is reported to inhibit angiogenesis by binding to the heparin sulfate proteoglycans involved in growth factor signaling (Zetter, 1998).

Endostatin XV

Recently, a C-terminal fragment of collagen XV (Endostatin XV) has been shown to inhibit angiogenesis like Endostatin XVIII, but with several functional differences (Sasaki et al., 2000).

Angiostatin

Angiostatin, an internal fragment of plasminogen comprising the first four kringle structures, is one of the most potent endogenous angiogenesis inhibitors described to date. It has been shown that systemic administration of angiostatin efficiently suppresses malignant glioma growth in vivo (Kirsch et al., 1998). Angiostatin has also been combined with conventional radiotherapy resulting in increased tumor eradication without increasing toxic effects in vivo (Mauceri et al., 1998). Other studies have demonstrated that retroviral and adenoviral mediated gene transfer of angiostatin cDNA resulted in inhibition of endothelial cell growth in vitro and angiogenesis in vivo. The inhibition of tumor-induced angiogenesis produced an increase in tumor cell death (Tanaka et al., 1998). Gene transfer of a cDNA coding for mouse angiostatin into murine T241 fibrosarcoma cells has been shown to suppress primary and metastatic tumor growth in vivo (Cao et al., 1998).

PEX

PEX is the C-terminal hemopexin domain of MMP-2 that inhibits the binding of MMP-2 to integrin $\alpha v \beta 3$ and blocks cell surface collagenolytic activity required for angiogenesis and tumor growth. It was cloned and described by Brooks et al. (1998).

Kringle-5

The kringle-5 domain of human plasminogen, which shares high sequence homology with the four kringles of angiostatin, has been shown to be a specific inhibitor for endothelial cell proliferation. Kringle-5 appears to be more potent than angiostatin on inhibition of basic fibroblast growth factor-stimulated capillary endothelial cell proliferation (Cao et al., 1997). In addition to its antiproliferative properties, kringle-5 also displays an anti-migratory activity similar to that of angiostatin that selectively affects endothelial cells (Ji et al., 1998).

Angiostatic Fusion Genes

Novel angiostatic fusion genes can be cloned using an elastin peptide motif (Val-Pro-Gly-Val-Gly) as a linker. These fusions combine two potent angiostatic genes to increase the suppression of tumor angiogenesis. Since these molecules operate through different mechanisms, their combination may result in synergistic effects. Examples of angiostatic fusion proteins include, but are not limited to, the fusion of endostatin 18 and angiostatin (endo/ang), endostatin 18 and the kringle 5 motif of plasminogen (endo/K5), as well as the monokine-induced by interferon-gamma and the interferon-alpha inducible protein 10 (MIG/IP10).

Chemokines

Chemokines are low-molecular weight pro-inflammatory cytokines capable of eliciting leukocyte chemotaxis.

Depending on the chemokine considered, the chemoattraction is specific for certain leukocyte cell types. Expressing chemokine genes into tumors may lead to more efficient recruiting of leukocytes capable of antitumoral activity. Moreover, in addition to their chemotactic activity, some chemokines possess an anti-angiogenic activity, i.e. they inhibit the formation of blood vessels feeding the tumor. For this reason, these chemokines are useful in cancer treatment.

Monokine-Induced by Interferon-Gamma (MIG)

MIG, the monokine-induced by interferon-gamma, is a CXC chemokine related to IP-10 and produced by monocytes. MIG is a chemoattractant for activated T cells, and also possesses strong angiostatic properties. Intratumoral injections of MIG induced tumor necrosis (Sgadari et al., 1997).

Interferon-Alpha Inducible Protein 10 (IP-10)

IP-10, the interferon-alpha inducible protein 10, is a member of the CXC chemokine family. IP-10 is produced mainly by monocytes, but also by T cells, fibroblasts and endothelial cells. IP-10 exerts a chemotactic activity on lymphoid cells such as T cells, monocytes and NK cells. IP-10 is also a potent inhibitor of angiogenesis. It inhibits neovascularization by suppressing endothelial cell differentiation. Because of its chemotactic activity toward immune cells, IP-10 was considered as a good candidate to enhance antitumour immune responses. Gene transfer of IP-10 into tumor cells reduced their tumorigenicity and elicited a long-term protective immune response (Luster and Leder, 1993). The angiostatic activity of IP-10 was also shown to mediate tumor regression. Tumor cells expressing IP-10 became necrotic in vivo (Sgadari et al., 1996). IP-10 was also shown to mediate the angiostatic effects of IL-12 that lead to tumor regression (Tannenbaum et al., 1998).

Soluble VEGF Receptors

FLT-1 (fms-like tyrosine kinase 1 receptor) is a membrane-bound receptor of VEGF (VEGF Receptor 1). It has been shown that a soluble fragment of FLT-1 (sFLT-1) has angiostatic properties by way of its antagonist activity against VEGF. Soluble FLT-1 acts by binding to VEGF but also because it binds and blocks the external domain of the membrane-bound FLT-1. One example of sFLT-1 is a human sFLT-1 spanning the 7 immunoglobulin-like domains of the external part of FLT-1.

sFLK-1/KDR

FLK-1 or KDR (kinase insert domain receptor) is a membrane-bound receptor of VEGF (VEGF Receptor 2). It has been shown that a soluble fragment of KDR (sKDR) has angiostatic properties by way of its antagonist activity against VEGF. The sKDR also binds and blocks the external domain of the membrane-bound KDR. One example of sKDR is a human sKDR spanning the 7 immunoglobulin-like domains of the external part of KDR.

Vascular Endothelial Growth Factor (VEGF) and Basic Fibroblast Growth Factor (bFGF)

VEGF is a growth factor active in angiogenesis and endothelial cell growth. It induces endothelial proliferation and vascular permeability. bFGF is an angiogenic agent with many potential gene therapy uses such as atherosclerosis therapy. VEGF and bFGF are ideal candidates for novel gene transfer protocols designed to promote new blood vessel growth. Stimulating angiogenesis by gene transfer approaches offers the hope of treating tissue ischemia which is untreatable currently.

Apoptosis

Apoptosis is the term used to describe the process of programmed cell death or cell suicide. This process is a normal component of the development and health of multicellular organisms. The abnormal regulation of apoptosis has been implicated in a variety of pathological disorders from cancer to autoimmune diseases.

Bcl-2 Interacting Killer (BIK)

Bik is a 18kD (160 amino acids) potent pro-apoptotic protein, also known as apoptosis inducer NBK, BP4, and BIP1. Bik is encoded by the gene bik (or nbk). The function of Bik is to accelerate programmed cell death by complexing with various apoptosis repressors such as Bcl-XL, BHRF1, Bcl-2, or its adenovirus homologue E1B protein. In transient transfection studies, Bik promoted cell death in a manner similar to the pro-apoptotic members of the Bcl-2 family, Bax and Bak.

BAK

Bak, a Bcl-2 homologue, is a pro-apoptotic protein that promotes apoptosis by binding anti-apoptotic family members including Bcl-2 and Bcl-XL and inhibits their activity as previously is described for Bik (Chittenden et al., 1995).

BAX

Bax is a 21kD protein that functions as an apoptosis regulator. Bax accelerates programmed cell death by dimerizing with and antagonizing the apoptosis repressor Bcl-2. The ratio of these protein dimers is thought to relate to the initiation of apoptosis. The effect of recombinant Bax expression in K562 erythroleukemia cells has been investigated by Kobayashi et al. (1998). Transfection with the Bax vector into K562 cells resulted in the induction of apoptosis. Furthermore, cells stably transfected with Bax were found to be more sensitive to the chemotherapeutic agents ara-X, doxorubicin, and SN-38 (Kobayashi et al., 1998).

BAD

The Bad protein (Bcl-2 binding component 6, bad gene or bbc6 or bcl218) is a small protein (168 amino acids, 18kDa) which promotes cell death. It successfully competes for the binding to Bcl-XL and Bcl-2, thereby affecting the level of heterodimerization of both these proteins with Bax. It can reverse the death repressor activity of Bcl-XL, but not that of Bcl-2.

BCL-2

B cell leukemia/lymphoma-2 (Bcl-2) is the prototype member of a family of cell death regulatory proteins. Bcl-2 is found mainly in the mitochondria and blocks apoptosis by interfering with the activation of caspases. Gene transfer of Bcl-2 into tumor cells has been shown to enhance their metastatic potential (Miyake et al., 1999). Bcl-2 gene transfer may be applied to bone marrow transplant since Bcl-2 enhances the survival of hematopoietic stem cells after reconstitution of irradiated recipient (Innes et al., 1999). Also, Bcl-2 gene transfer could be useful against neurodegenerating diseases since expression of Bcl-2 in neurons protects them from apoptosis (Saille et al., 1999).

BCL-XS

Bcl-XS (short isoform) is a dominant negative repressor of Bcl-2 and Bcl-XL. It has been used in gene therapy experiments to initiate apoptosis in tumors that express Bcl-2 and Bcl-XL. Expression of Bcl-XS reduces tumor size (Ealovega et al., 1996) and sensitizes tumor cells to chemotherapeutic agents (Sumatran et al., 1995), suggesting a role for Bcl-XS in initiating cell death in tumors that express Bcl-2 or Bcl-XL (Dole et al., 1996).

GAX

Gax is an homeobox gene coding for a transcription factor that inhibits cell proliferation in a p21-dependent manner. Gax is down-regulated when cells are stimulated to proliferate. Gax over-expression leads to Bcl-2 down-regulation and Bax up-regulation in mitogen-activated cells (Perlman et al., 1998). Thus, Gax may be useful to inhibit the growth of certain tumor cells. Moreover, Gax over-expression in vascular smooth muscle cells inhibits their proliferation (Perlman et al., 1999). Hence, Gax gene transfer could limit vascular stenosis following vascular injuries.

Tumor Suppressor Genes

Various mutations of tumor suppressor genes have been associated with different types of cancers. In these cases, somatic gene therapy with wild-type versions of tumor suppressor genes have been contemplated as anti-cancer therapeutic approaches. p16, p21, p27 & p53 inhibit the cell cycle by acting on the cyclin-dependent kinases.

P16

P16, a 15kD protein (148 amino acids), is also known as CDK4I, P16-INK4, P16-INK4A, or multiple tumor suppressor 1 (MTS1). P16 is encoded by the gene cdkn2a or cdkn2. P16 forms a heterodimer with cyclin-dependent kinase 4 and 6, thereby preventing their interaction with cyclin D both in vitro and in vivo. Thus, P16 acts as a negative regulator of the proliferation of normal cells.

P16 (cdkn2) mutations are involved in tumor formation in a wide range of tissues. cdkn2a is homozygously deleted, mutated, or otherwise inactivated in a large proportion of tumor cell lines and some primary tumors including melanomas and tumors of the biliary tract, pancreas and stomach. Loss of p16IKN4a gene expression is commonly observed in mesothelioma tumors and other cell lines. It has been shown that p16INK4A transduction with an expressing adenovirus in mesothelioma cells resulted in decreased cell growth and the death of the transduced cells (Frizelle et al., 1998). Furthermore, adenoviral mediated gene transfer of wild-type p16 into three human glioma cell lines (U251 MG, U-87 MG and D54 MG) that were not expressing an endogenous p16/CDKN2 gene resulted in the arrest of cell growth in the G0 and G1 phases (Fueyo et al., 1996). In addition, adenoviral mediated gene transfer of wild-type p16-INK4A into lung cancer cell lines that do not express p16-INK4A inhibited tumor proliferation both in vitro and in vivo (Jin et al., 1995). Thus, the restoration of the wild-type P16 protein in tumor cells could have cancer therapeutic utility.

P21 p21 is an 18kD protein (164 amino acids) also known as Cyclin-Dependent Kinase Inhibitor 1 (CDKN1), melanoma differentiation associated protein 6 (MDA-6), and CDK-interacting protein 1. p21 is encoded by the gene CDKN1, also known as CIP1 and WAF1. p21 may be the important intermediate by which p53 mediates its role as an inhibitor of cellular proliferation in response to DNA damage. p21 may bind to and inhibit cyclin-dependent kinase activity, preventing the phosphorylation of critical cyclin-dependent kinase substrates and blocking cell cycle progression and proliferation. p21 is expressed in all adult human tissues. p21 gene transfer into tumor cells could be useful to inhibit tumor growth.

Recombinant adenovirus mediated p21 gene transfer in two human non-small cell lung cancer (NSCLC) cell lines resulted in a dose-dependent p21 induction and concomitant cell growth inhibition due to G0/G1 cell cycle arrest. Moreover, injection of an adenovirus carrying p21 into NSCLC pre-established tumors in mice reduced tumor growth and increased survival of the animals (Joshi et al., 1998). These results support the use of p21 for cancer gene therapy.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" [R. I. Freshney, ed. (1986)); "Immobilized Cells And Enzymes" (IRL Press, (1986)); B. Perbal, "A Practical Guide To Molecular Cloning" (1984).

A "vector" is a replicon, such as plasmid, phage or cosmid, to which another DNA segment may be attached so as to bring about the replication of the attached segment.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Various promoters may be used to drive vectors.

A cell has been "transduced" by exogenous or heterologous DNA when such DNA has been introduced inside the cell, usually by a viral vector. The transducing DNA may (as in the case of lentiviral vectors) or may not be integrated (covalently linked) into the genome of the cell. In prokaryotes, yeast, and mammalian cells for example, DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "therapeutic gene" refers to a gene that confers a desired phenotype. For example, a constitutively active retinoblastoma (CA-rb) gene is used to prevent intraocular proliferation or a genetic deficit is restored by the transfer of peripherin gene. Other desirable phenotypes include inhibition of tumor growth, inhibition or regulation of angiogenesis and regulation of apoptosis.

As used herein, the term "marker gene" refers to a coding sequence attached to heterologous promoter or enhancer elements and whose product is easily and quantifiably assayed when the construct is introduced into tissues or cells. Markers commonly employed include radioactive elements, enzymes, proteins (such as the enhanced green fluorescence protein) or chemicals which fluoresce when exposed to ultraviolet light, and others.

The present invention is directed to a novel means of treating inherited or proliferative blinding diseases by means of lentiviral gene transfer. There is provided a method of inhibiting intraocular cellular proliferation in an individual having an ocular disease, comprising the step of administering to said individual a pharmacologically effective dose of a lentiviral vector comprising a therapeutic gene that inhibits intraocular cellular proliferation. Representative examples of ocular diseases which may be treated using this method of the present invention include age-related macular degeneration, proliferative diabetic retinopathy, retinopathy of prematurity, glaucoma, and proliferative vitreoretinopathy. The therapeutic gene can be a constitutively active form of the retinoblastoma gene, a p16 gene or a p21 gene. Preferably, the lentiviral vector is administered in a dosage of from about $10^6$ to $10^9$ transducing units into the capsular, vitreal or sub-retinal space.

The present invention is also drawn to a method of inhibiting intraocular neovascularization in an individual having an ocular disease, comprising the step of administering to said individual a pharmacologically effective dose of a lentiviral vector comprising a therapeutic gene that inhibits intraocular neovascularization. Representative examples of ocular diseases which may be treated using this method of the present invention include age-related macular degeneration, proliferative diabetic retinopathy, retinopathy of prematurity, glaucoma, and proliferative vitreoretinopathy. The therapeutic gene can be a gene that regulates angiogenesis or apoptosis. In general, genes that regulate angiogenesis include genes that encode tissue inhibitor of metalloproteinase (TIMP)-1, TIMP-2, TIMP-3, TIMP-4, endostatin, angiostatin, endostatin XVIII, endostatin XV, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fms-like tyrosine kinase 1 receptor), and kinase insert domain receptor (KDR), whereas genes that regulate apoptosis include genes that encode Bcl-2, Bad, Bak, Bax, Bik, Bcl-X short isoform and Gax. Preferably, the lentiviral vector is administered in a dosage of from about $10^6$ to $10^9$ transducing units into the capsular, vitreal or sub-retinal space.

The present invention also provides a method of preventing neovascularization and corneal transplant failure. Corneal buttons are transduced ex vivo prior to transplantation with a lentiviral vector comprising a therapeutic gene that inhibits neovascularization. The therapeutic gene is a gene that regulates angiogenesis, and representative examples of such genes have been listed above.

Figure 19:
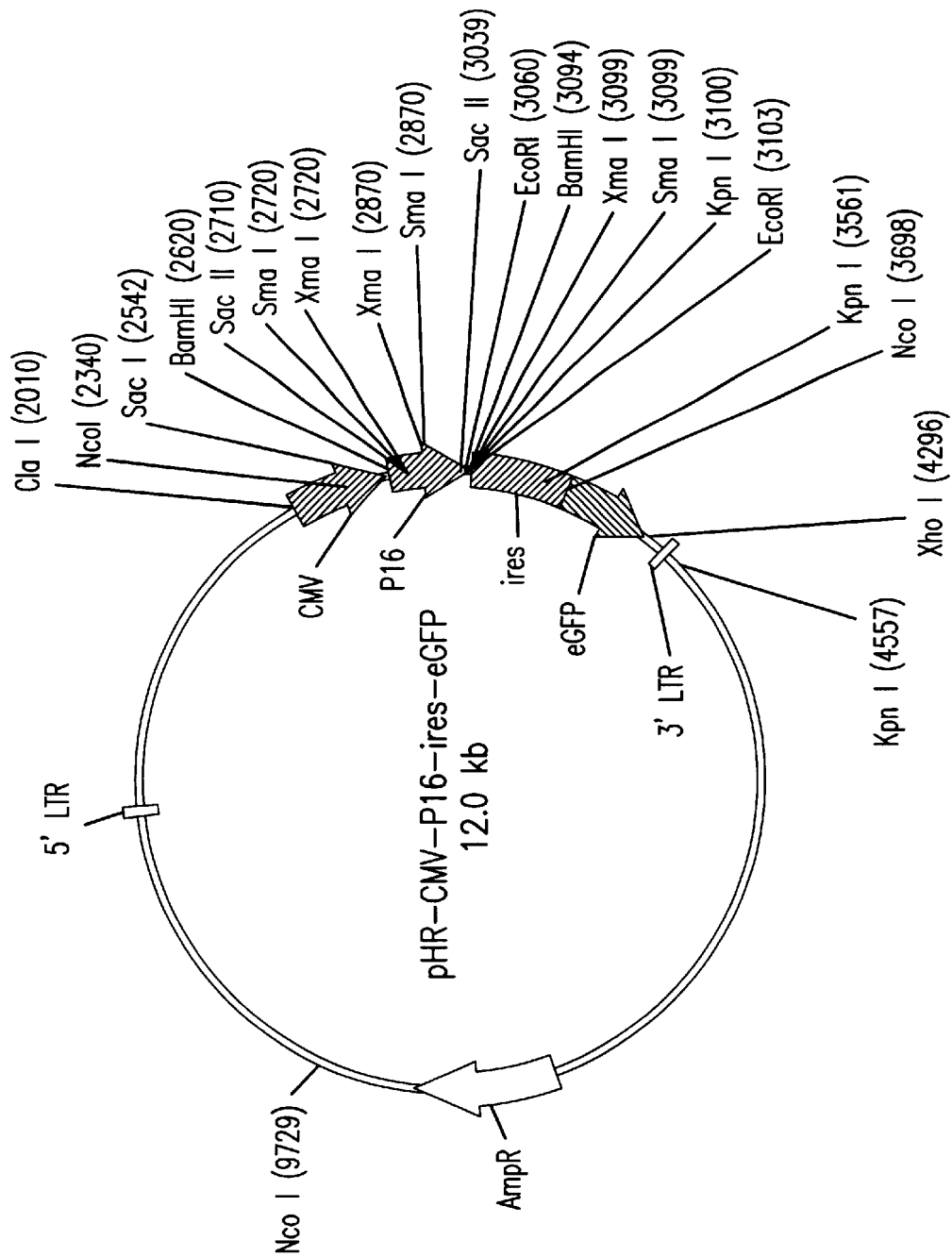
FIG. 19 shows a map for the lentiviral vector pHR-CMV-P16-ires-eGFP carrying a p16 gene.
Figure 20:
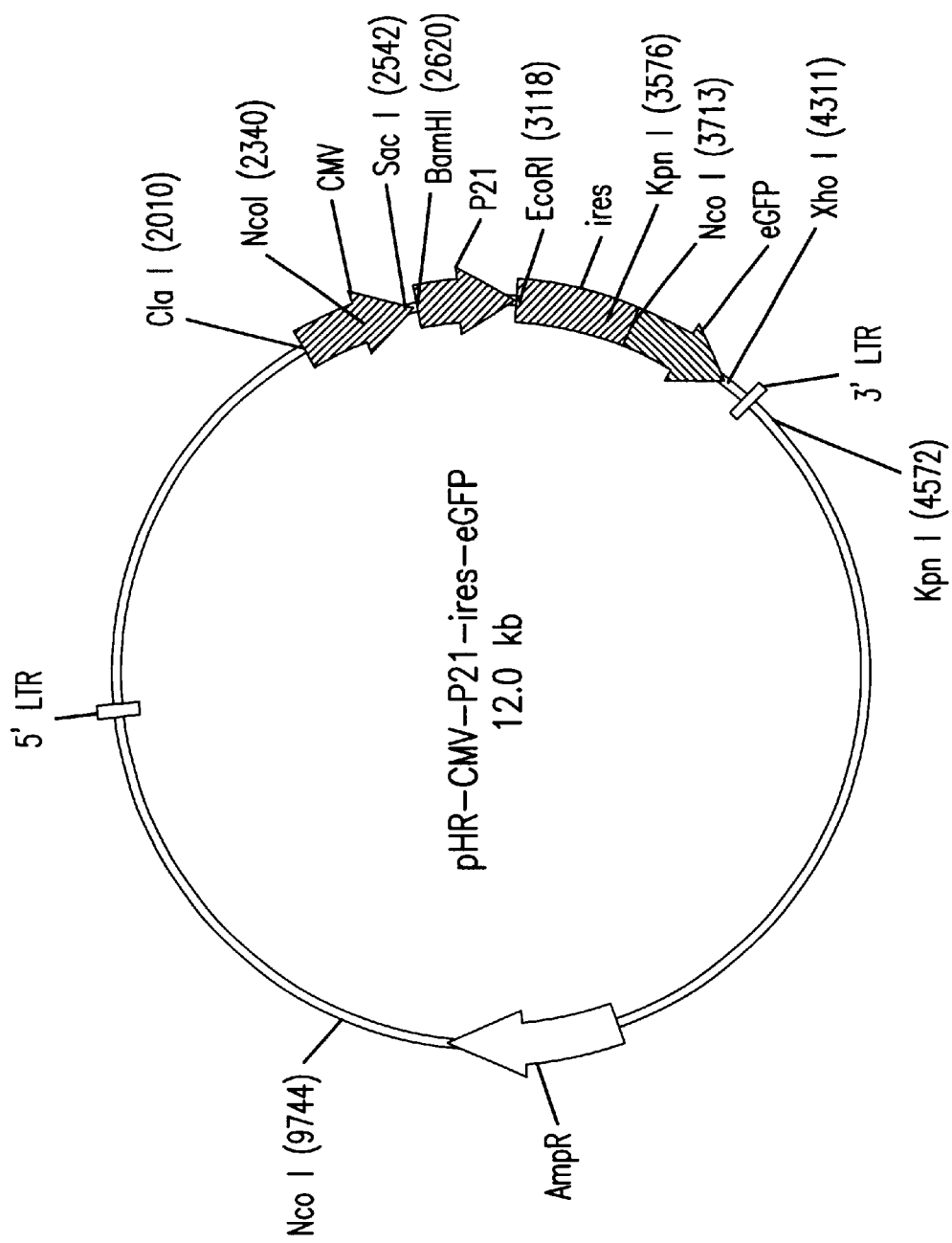
FIG. 20 shows a map for the lentiviral vector pHR-CMV-P21-ires-eGFP carrying a p21 gene.
Figure 30:
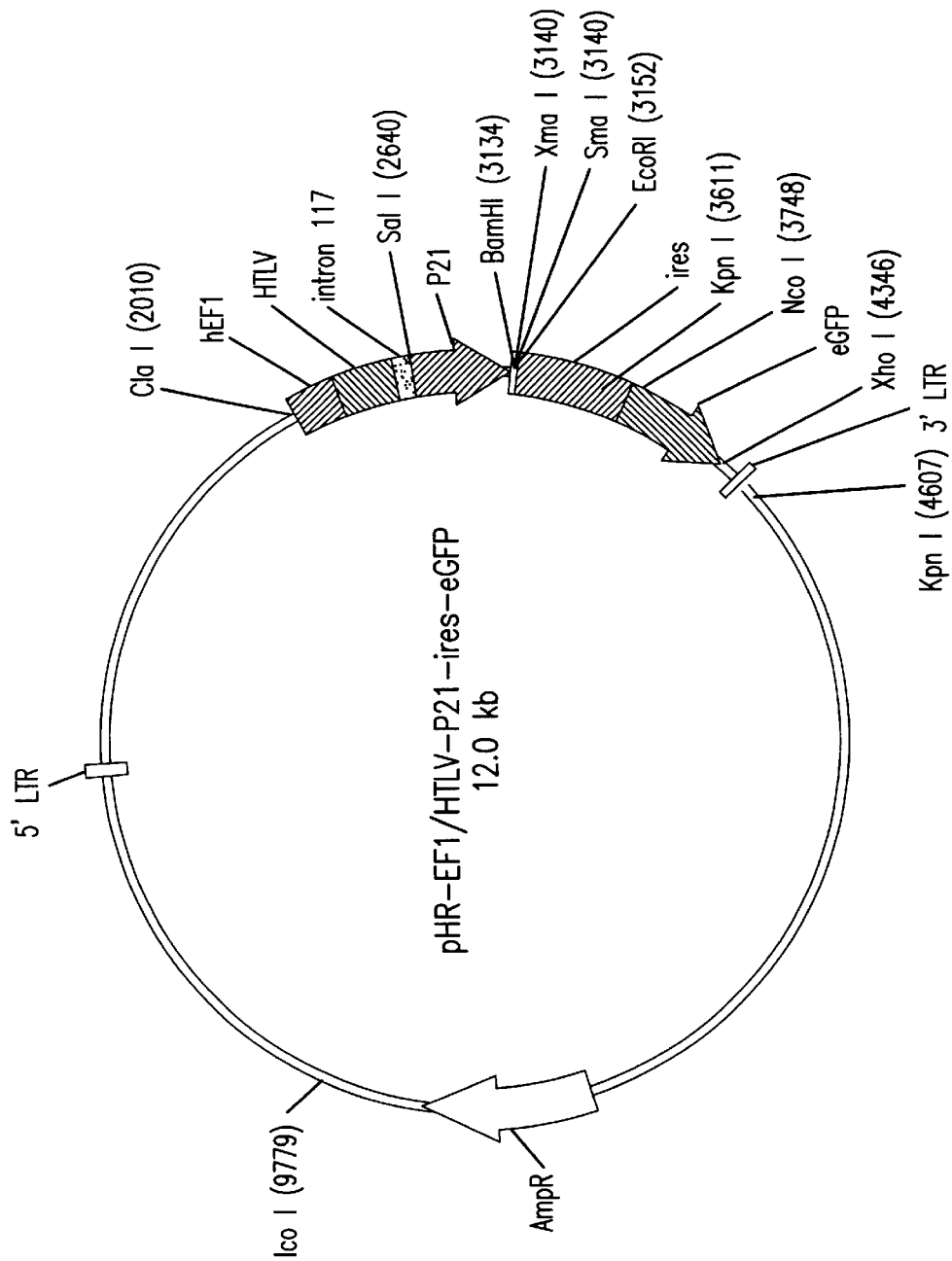
FIG. 30 shows a map for the lentiviral vector pHR-EF1/HTLV-P21-ires-eGFP carrying a p21 gene.

In another aspect of the present invention, there are provided lentiviral vectors capable of mediating gene transfer to a number of cell types. The recombinant lentiviral vectors comprise (i) an IRES (internal ribosome entry site) element between two cloning sites so that two different proteins are produced from a single transcript; (ii) a marker gene such as the enhanced green fluorescent protein gene; and (iii) a therapeutic gene. In general, the therapeutic gene can regulate tumor growth, angiogenesis or apoptosis. In one embodiment, therapeutic genes that regulate tumor growth include p16, p21, p27, p53 and PTEN, and representative lentiviral vectors are pHR-CMV-P16-ires-eGFP (FIG. 19), pHR-CMV-P21-ires-eGFP (FIG. 20) and pHR-EF1/HTLV-P21-ires-eGFP (FIG. 30).

Figure 16:
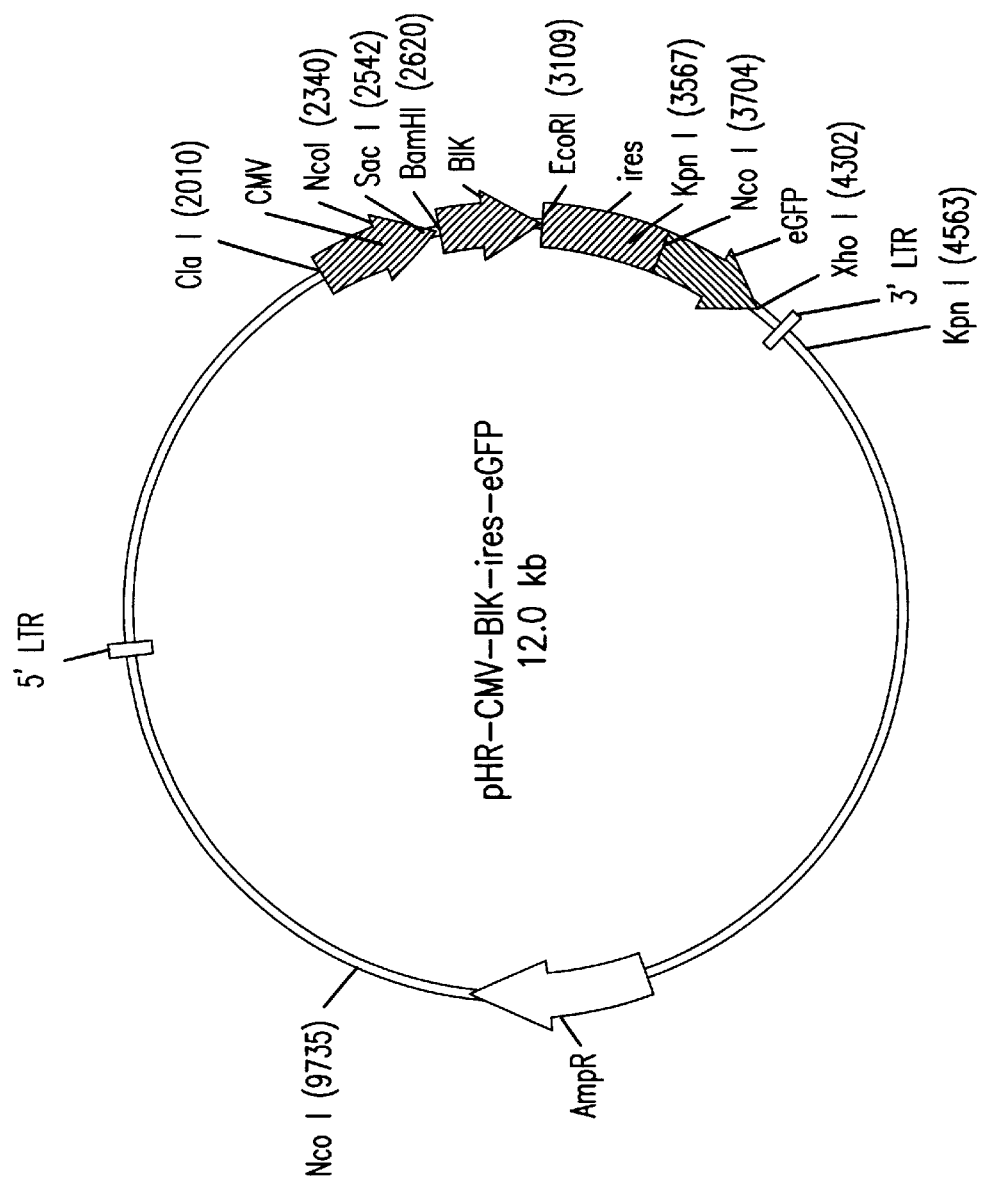
FIG. 16 shows a map for the lentiviral vector pHR-CMV-BIK-ires-eGFP carrying a BIK gene.

In another embodiment, therapeutic genes that regulate apoptosis include Bik, Bad, Bak, Bax, Bcl-2,Bcl-XL and Gax, and representative lentiviral vector is pHR-CMV-BIK-ires-eGFP (FIG. 16).

Figure 18:
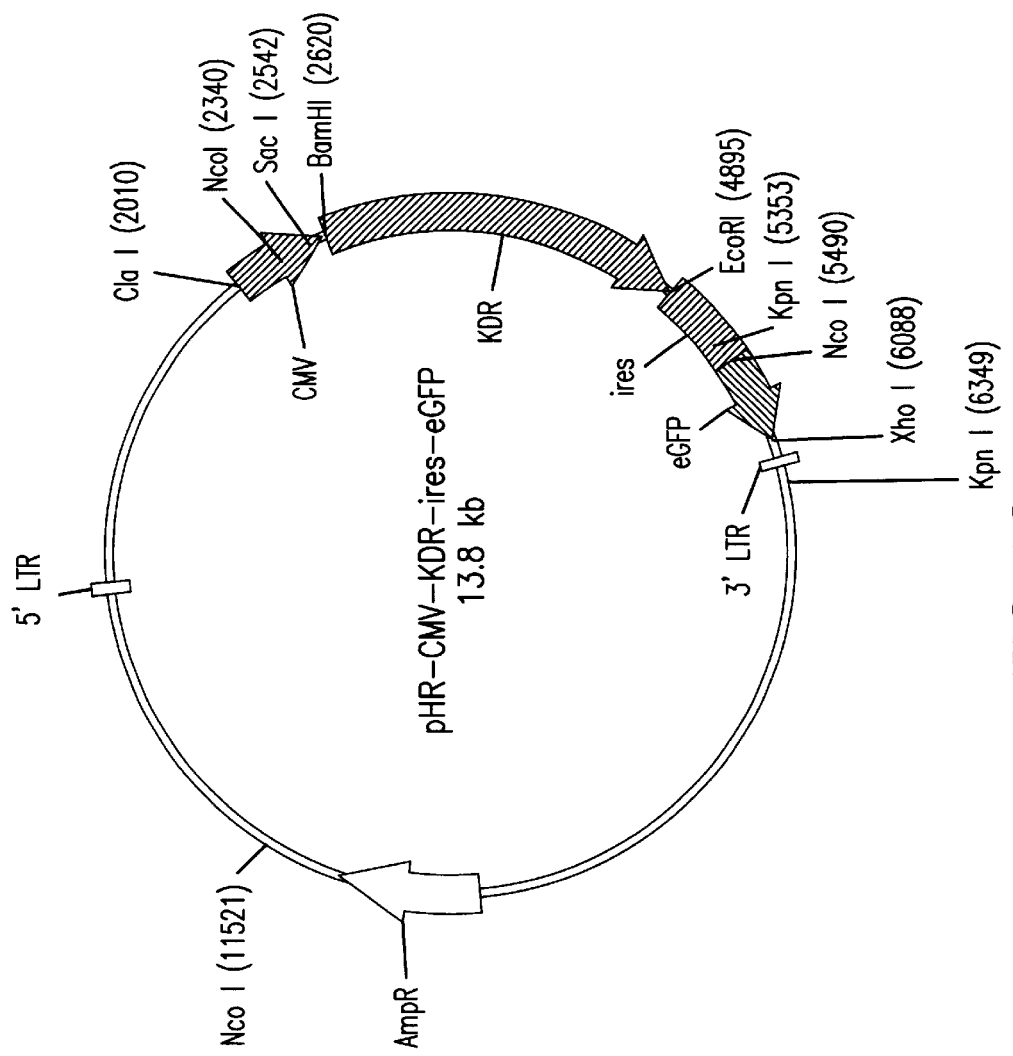
FIG. 18 shows a map for the lentiviral vector pHR-CMV-KDR-ires-eGFP carrying a KDR gene.
Figure 21:
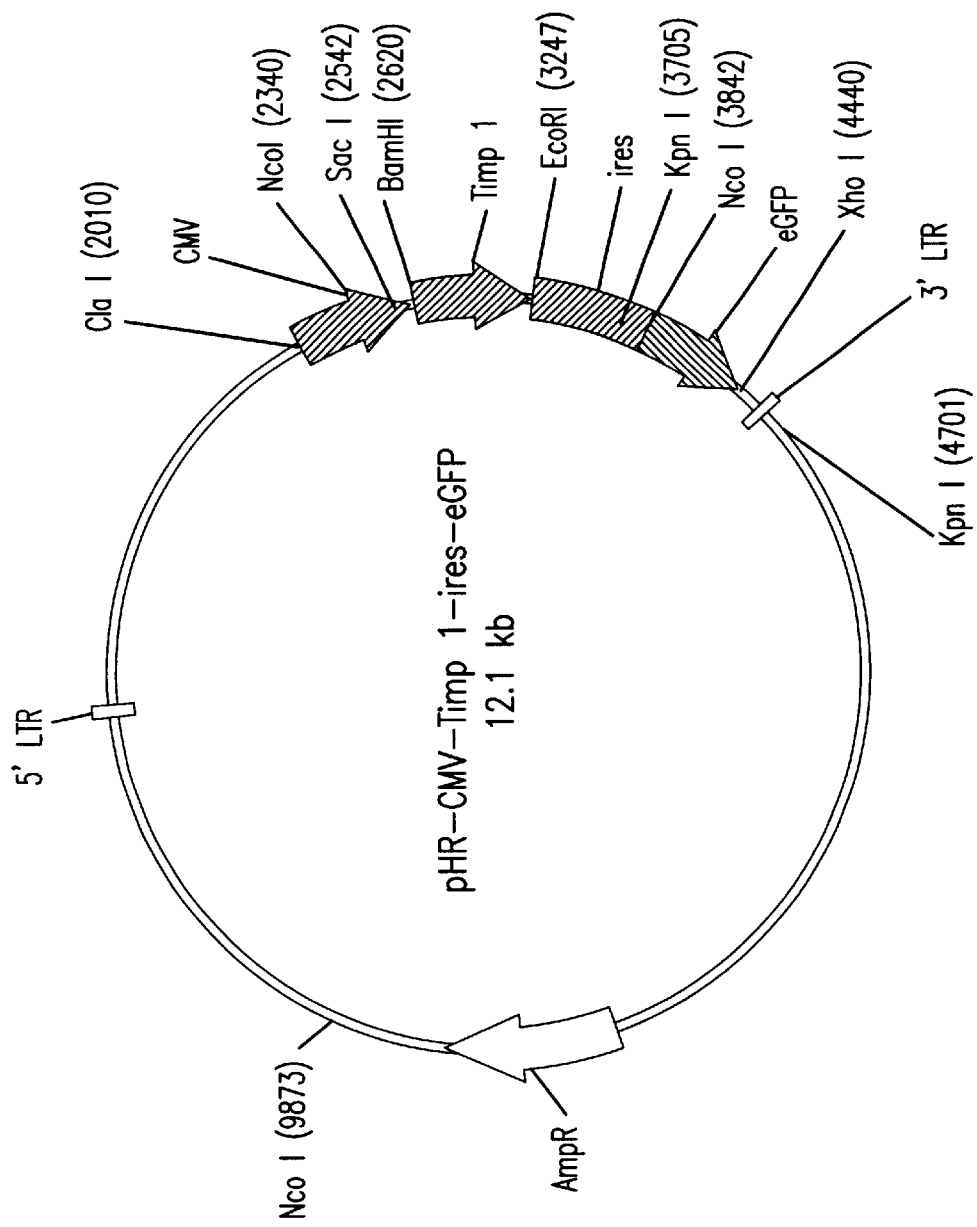
FIG. 21 shows a map for the lentiviral vector pHR-CMV-Timp1-ires-eGFP carrying a Timp1 gene.
Figure 22:
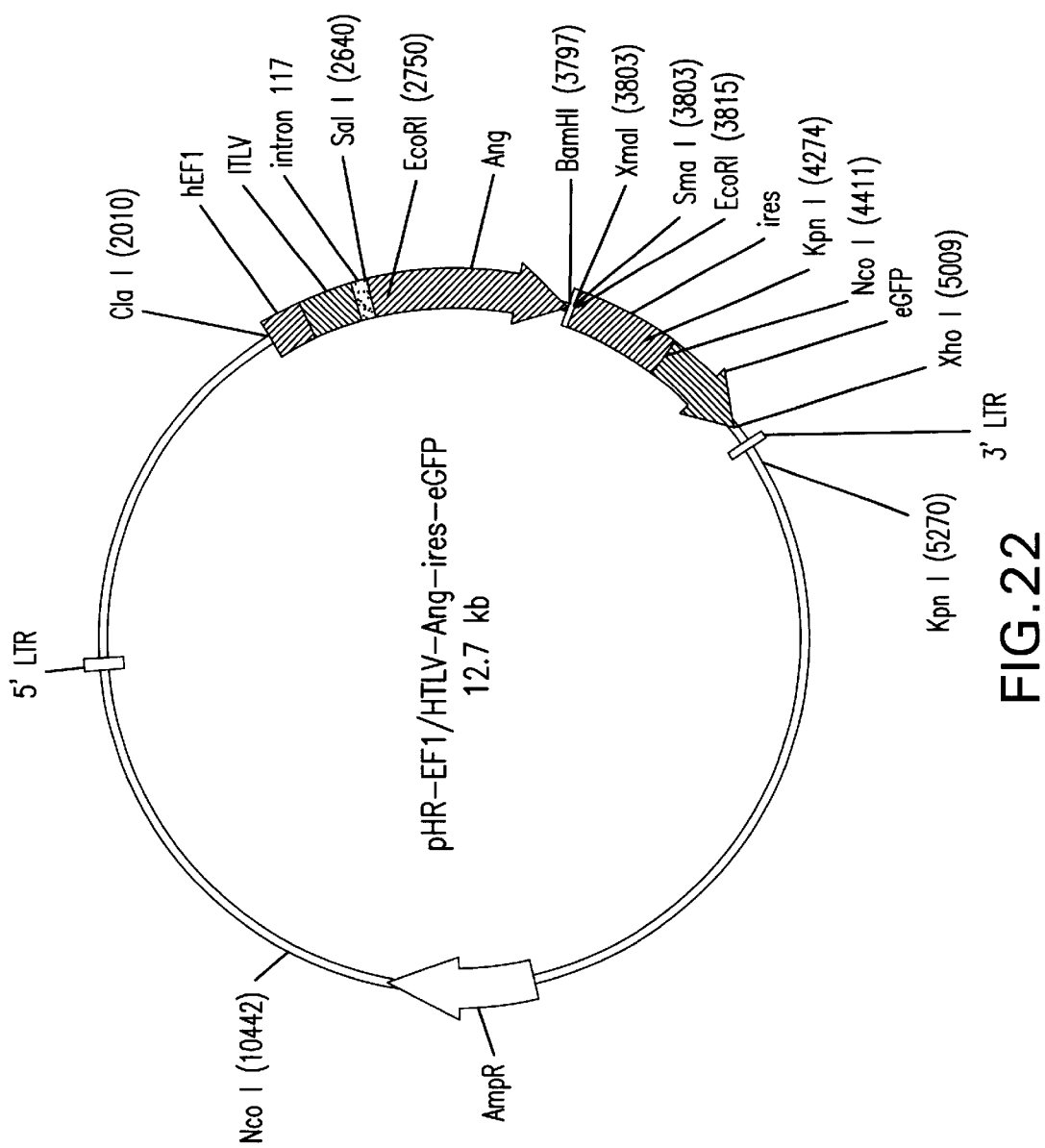
FIG. 22 shows a map for the lentiviral vector pHR-EF1/HTLV-Ang-ires-eGFP carrying an angiostatin gene.
Figure 23:
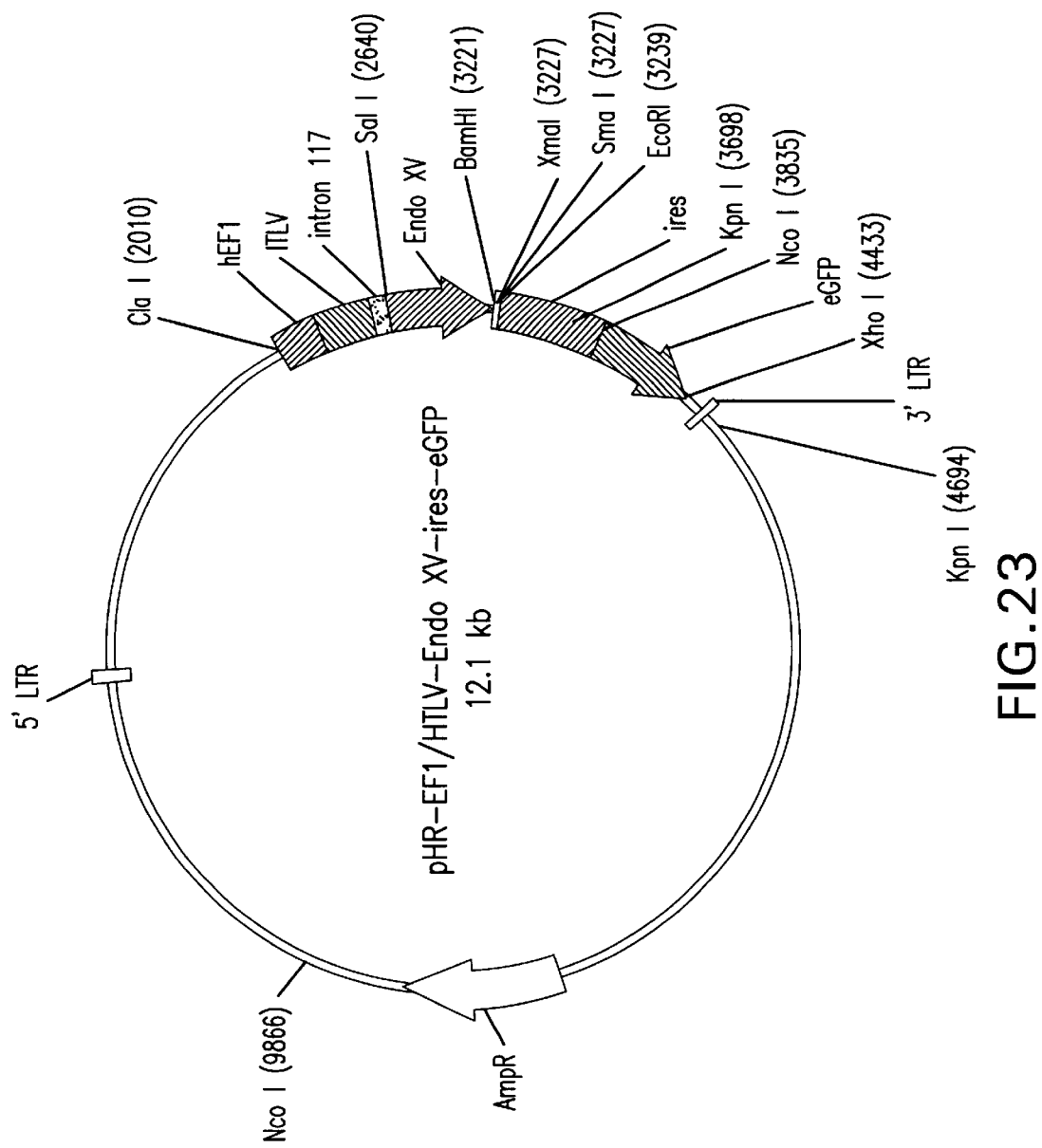
FIG. 23 shows a map for the lentiviral vector pHR-EF1/HTLV-Endo XV-ires-eGFP carrying an endostatin XV gene.
Figure 26:
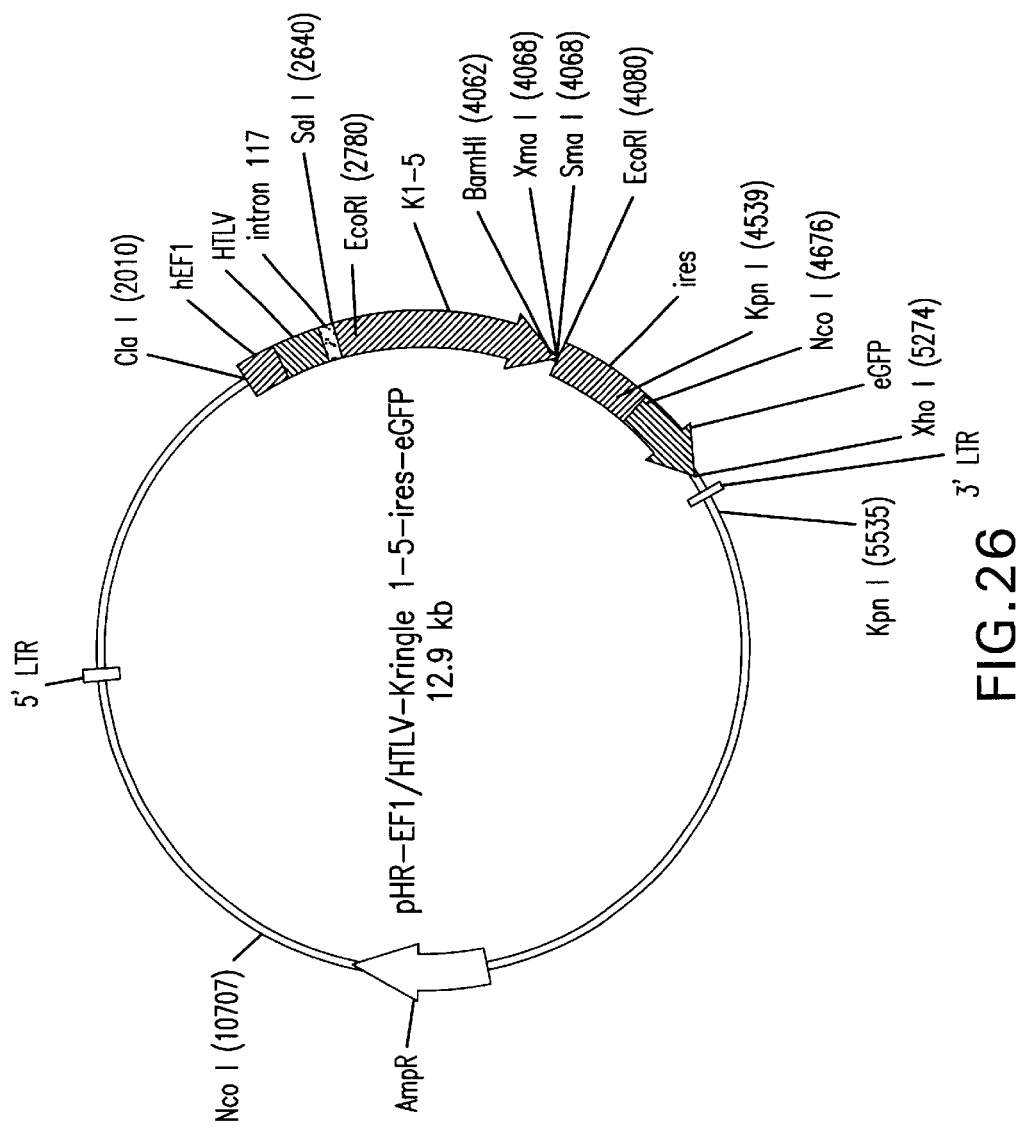
FIG. 26 shows a map for the lentiviral vector pHR-EF1/HTLV-Kringle 1-5-ires-eGFP carrying a Kringle gene.
Figure 28:
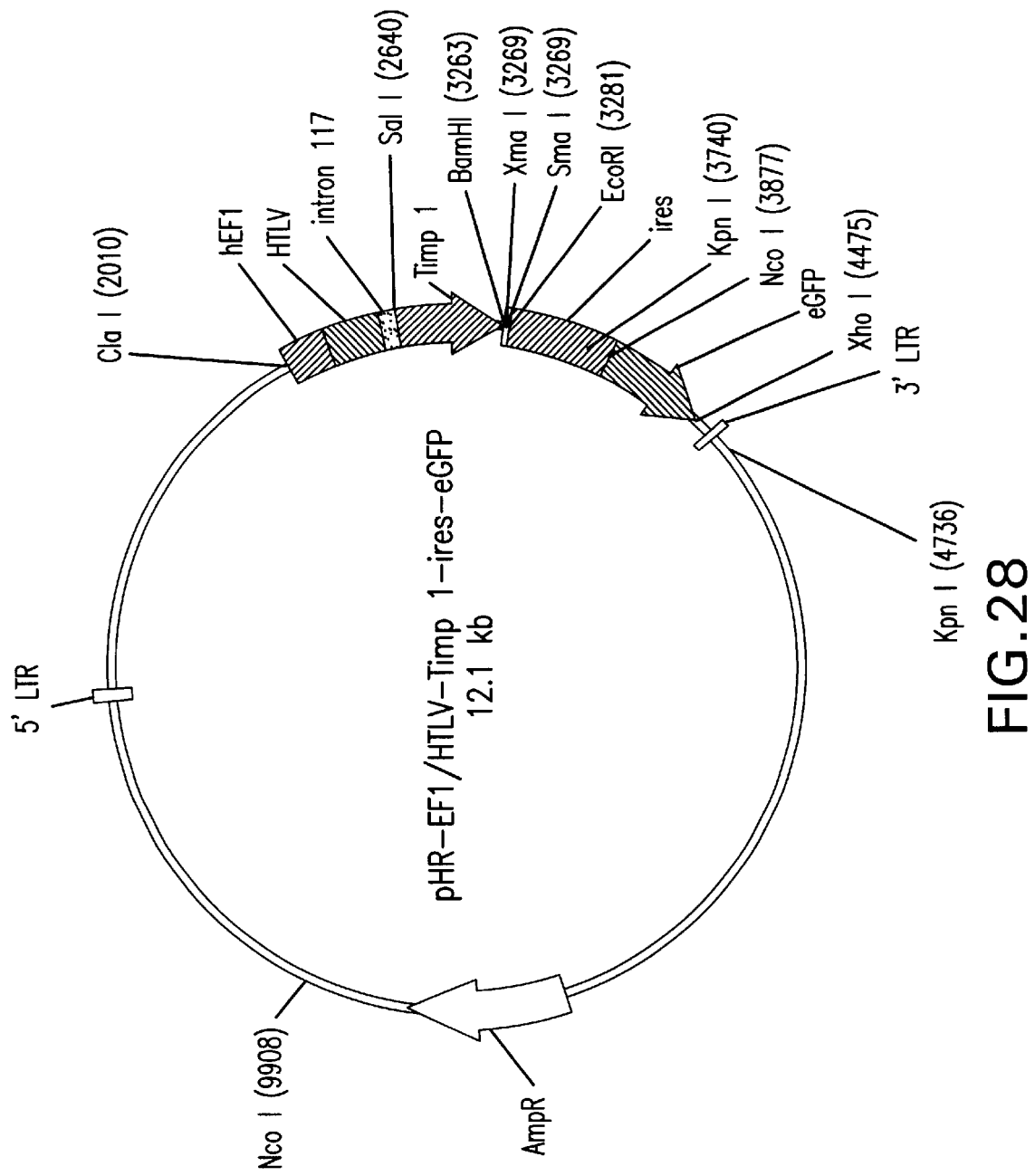
FIG. 28 shows a map for the lentiviral vector pHR-EF1/HTLV-Timp1-ires-eGFP carrying a Timp1 gene.
Figure 29:
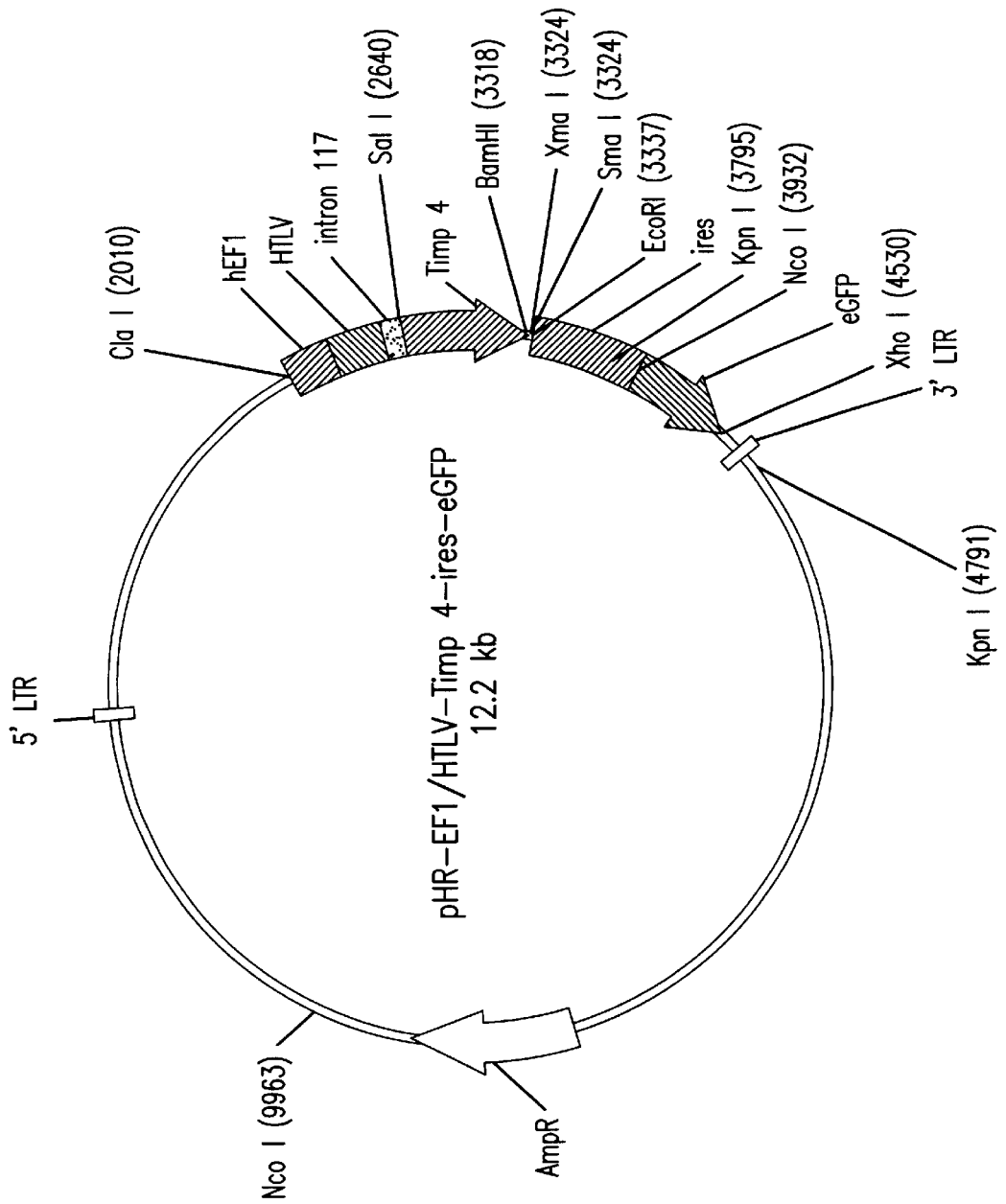
FIG. 29 shows a map for the lentiviral vector pHR-EF1/HTLV-Timp4-ires-eGFP carrying a Timp4 gene.
Figure 31:
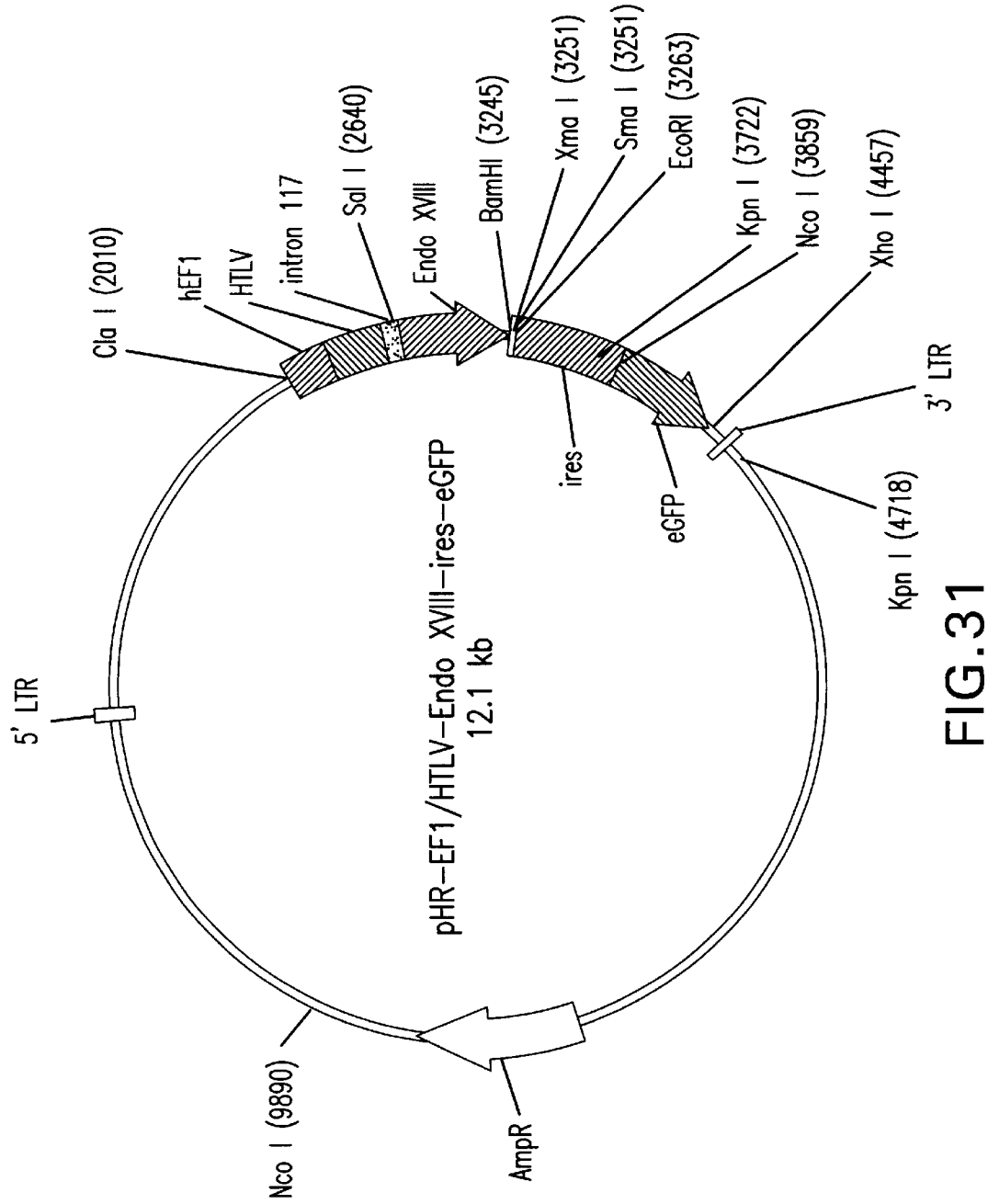
FIG. 31 shows a map for the lentiviral vector pHR-EF1/HTLV-Endo XVIII-ires-eGFP carrying an endostatin XVIII gene.

In yet another embodiment, therapeutic genes that regulate angiogenesis include genes that encode tissue inhibitor of metalloproteinase (TIMP)-1, TIMP-2, TIMP-3, TIMP-4, endostatin, angiostatin, endostatin XVIII, endostatin XV, the C-terminal hemopexin domain of matrix metalloproteinase-2, the kringle 5 domain of human plasminogen, FLT-1 (fms-like tyrosine kinase 1 receptor), KDR (kinase insert domain receptor), IP-10 (the interferon-alpha inducible protein 10) and MIG (the monokine-induced by interferon-gamma). Representative lentiviral vectors are pHR-CMV-KDR-ires-eGFP (FIG. 18), pHR-CMV-Timp1-ires-eGFP (FIG. 21), pHR-EF1/HTLV-Ang-ires-eGFP (FIG. 22), pHR-EF1/HTLV-Endo XV-ires-eGFP (FIG. 23), pHR-EF1/HTLV-Kringle 1-5-ires-eGFP (FIG. 26), pHR-EF1/HTLV-Timp1-ires-eGFP (FIG. 28), pHR-EF1/HTLV-Timp4-ires-eGFP (FIG. 29) and pHR-EF1/HTLV-Endo XVIII-ires-eGFP (FIG. 31).

Figure 15:
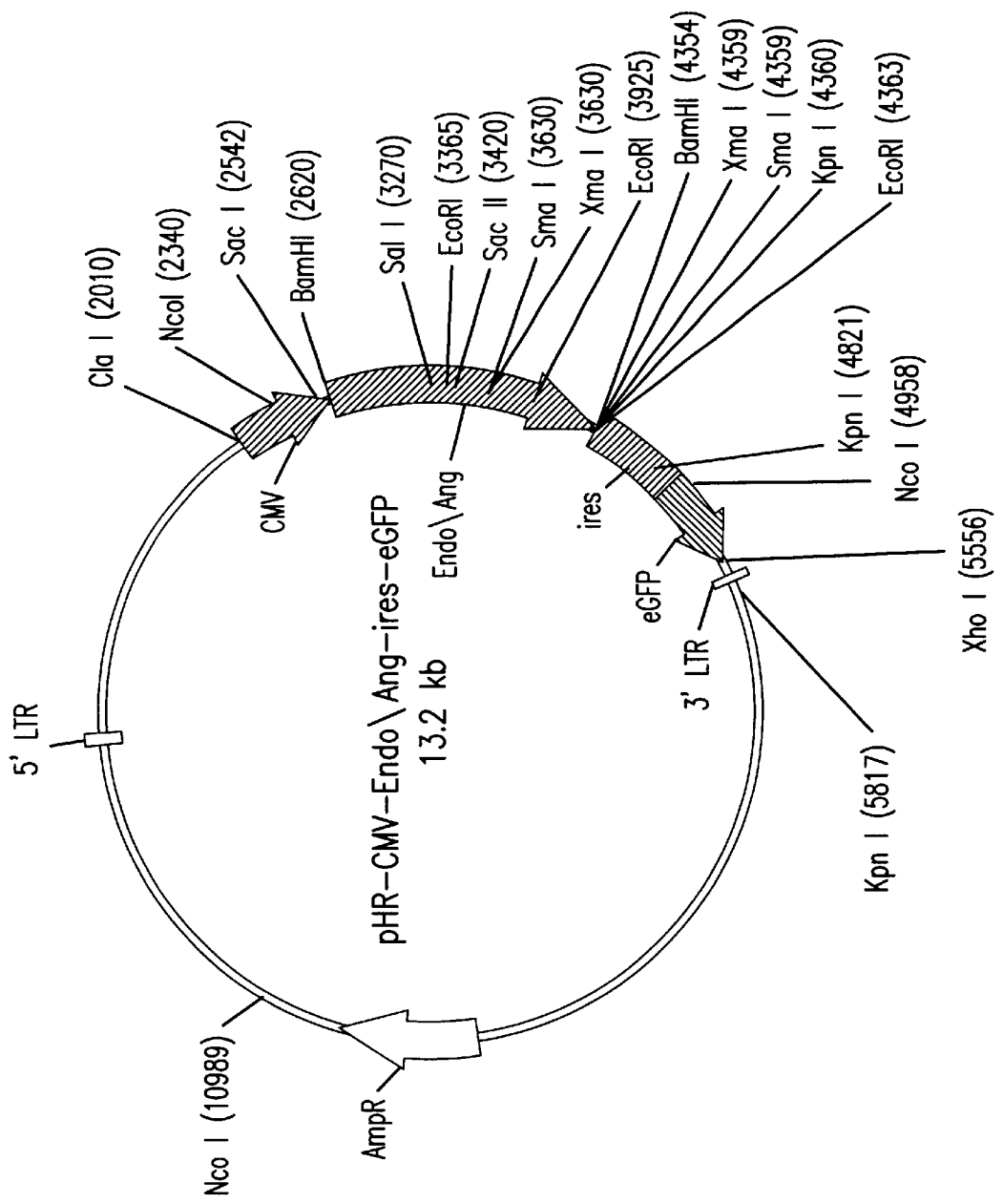
FIG. 15 shows a map for the lentiviral vector pHR-CMV-Endo/Ang-ires-eGFP carrying an endostatin/angiostatin fusion gene.
Figure 24:
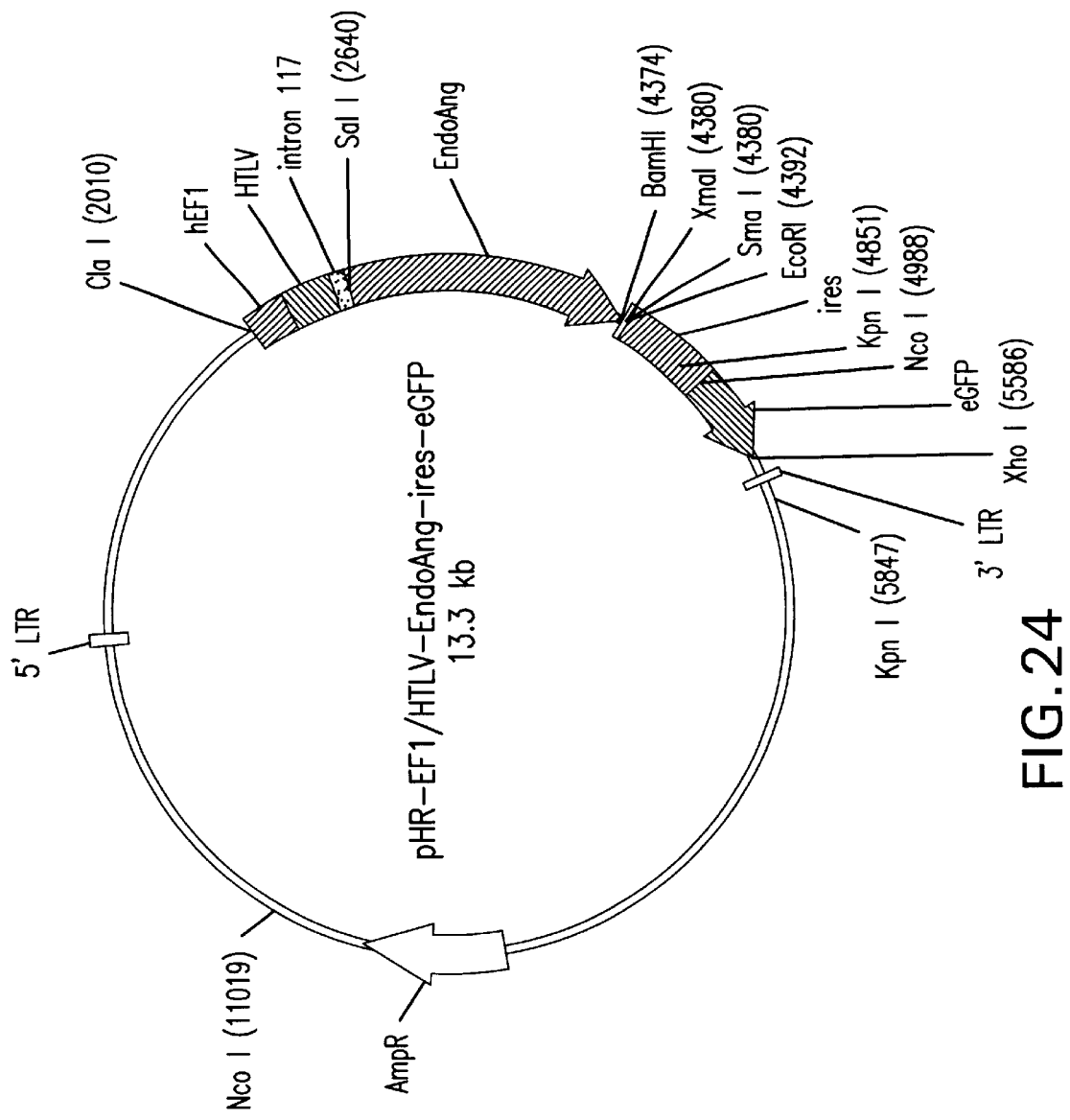
FIG. 24 shows a map for the lentiviral vector pHR-EF1/HTLV-EndoAng-ires-eGFP carrying an endostatin/angiostatin fusion gene.
Figure 25:
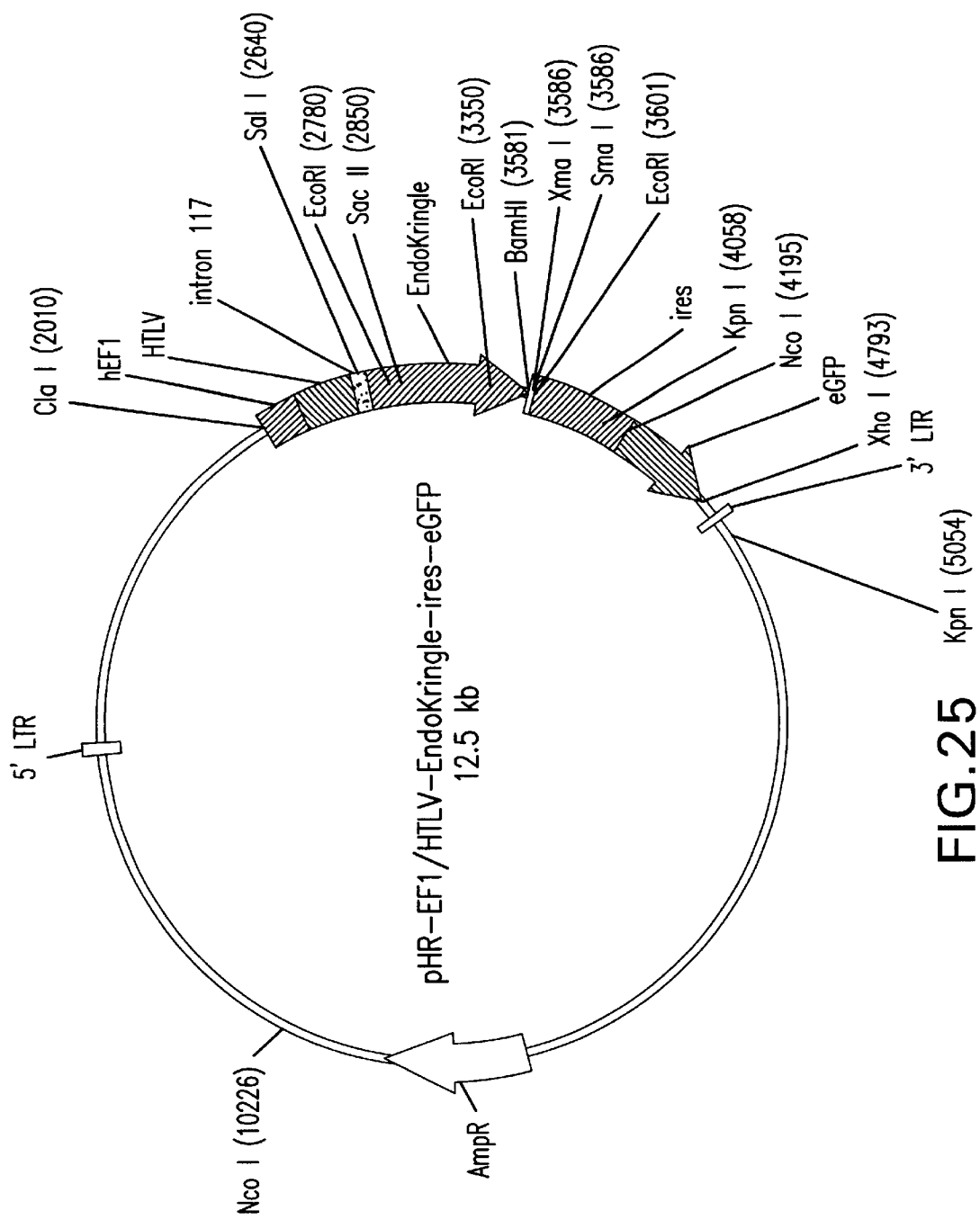
FIG. 25 shows a map for the lentiviral vector pHR-EF1/HTLV-EndoKringle-ires-eGFP carrying an endostatin/kringle fusion gene.
Figure 27:
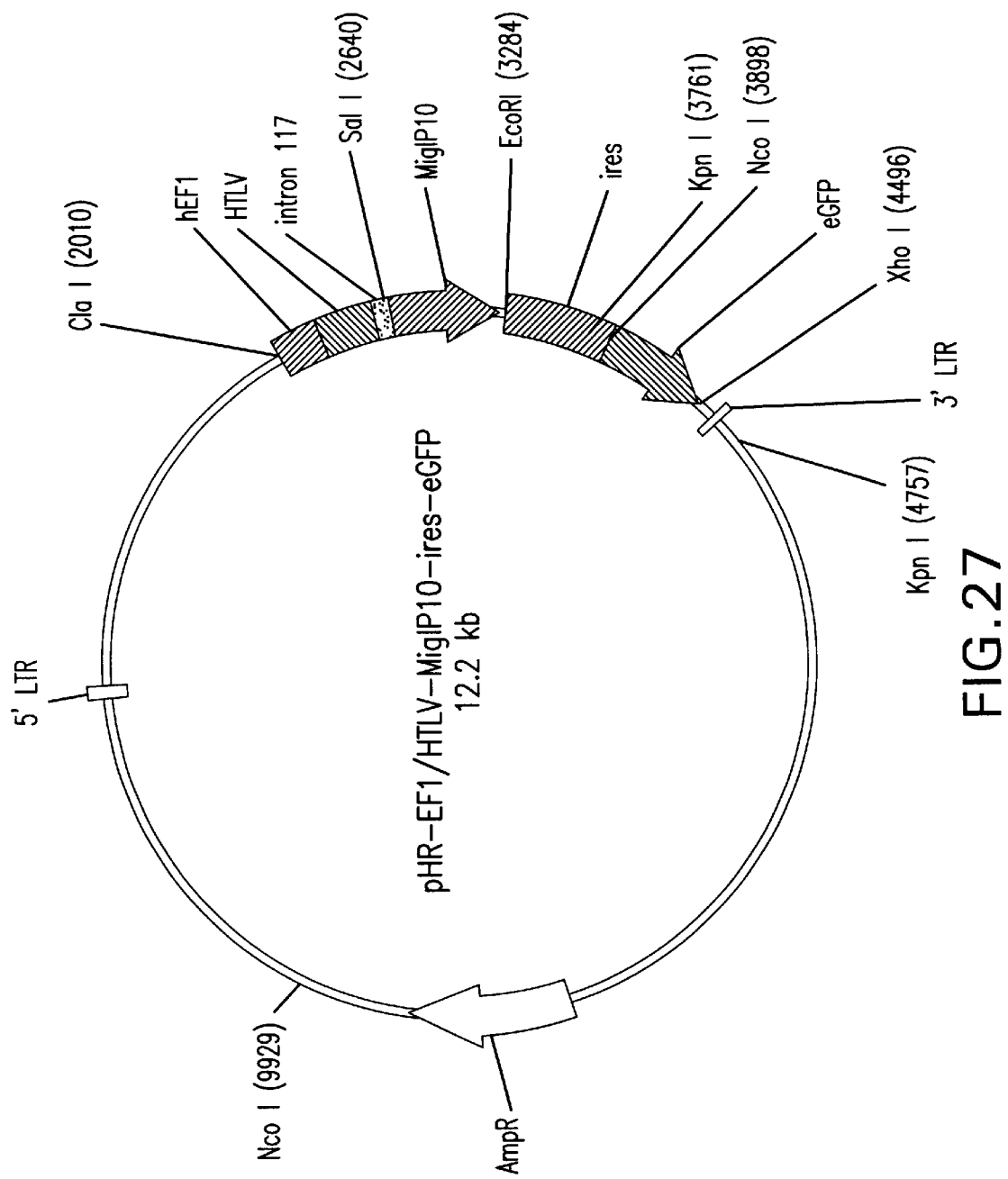
FIG. 27 shows a map for the lentiviral vector pHR-EF1/HTLV-MigIP10-ires-eGFP carrying a Mig/IP10 fusion gene.

In yet another embodiment, therapeutic genes that regulate angiogenesis encode angiostatic fusion protein such as a fusion protein of endostatin and angiostatin, endostatin and the kringle 5 domain of human plasminogen, and Mig (monokine-induced by interferon-gamma) and IP10 (interferon-alpha inducible protein 10). Representative lentiviral vectors are pHR-CMV-Endo/Ang-ires-eGFP (FIG. 15), pHR-CMV-Endo/Kringle-ires-eGFP (FIG. 17), pHR-EF1/HTLV-EndoAng-ires-eGFP (FIG. 24), pHR-EF1/HTLV-EndoKringle-ires-eGFP (FIG. 25) and pHR-EF1/HTLV-MigIP10-ires-eGFP (FIG. 27).

The following examples are given for the purpose of illustrating various embodiments of the invention and are not meant to limit the present invention in any fashion:

EXAMPLE 1

Cells and Tissue

Primary explants of human choroidal fibroblasts (HCF), human umbilical vein endothelial cells (HUVEC) and human fetal retinal pigment epithelial cells (HRPE) were established and were plated in conditions which either did or did not promote mitotic activity. Stable photoreceptor-derived cells (Y-79 and Weri-Rb-1) were also cultured.

Human retina and RPE, obtained at the time of enucleation for retinoblastoma were used to demonstrate the ability of lentiviral vectors to transduce these mitotically inactive cells and induce the expression of an exogenous human peripherin transgene. Human corneas obtained at the time of corneal transplant surgery were used to demonstrate the ability of lentiviral vectors to transduce these mitotically inactive cells with the marker gene enhanced green fluorescence protein gene.

EXAMPLE 2

Lentivirus Vector

A three plasmid-based lentiviral vectoring system pseudotyped with the vesicular stomatitis virus (VSV) envelope and which contained the green fluorescent protein (GFP) gene as a marker was used (FIG. 1). Recombinant lentiviruses were produced as described by Naldini et al. The cytomegalovirus (CMV) immediate-early gene promoter directed expression of eGFP in the plasmid pHR'-CMV-eGFP. Stocks of virus were generated as follows. Human kidney 293T cells ($5\times10^6$) were plated on 10 cm plates, and were cotransfected the following day with 10 ug of pCMVΔR8.91 (packaging function plasmid), 10 ug of pHR'-CMV-eGFP (marker gene plasmid), and 2 ug of pMD.G (the VSV-G envelope containing plasmid) by calcium phosphate precipitation in D10 growth medium (high glucose DMEM with 10% fetal bovine serum) and antibiotics. After 12–16 h at 37° C., the medium was removed and fresh D10 growth medium was added. Cells were cultured for an additional 10 hours. Fresh D10 medium containing 10 mM sodium butyrate and 20 mM Hepes buffer was added to the cells and the cells were cultured for another 12 hours. This medium was replaced with new D10 medium containing 20 mM Hepes buffer, and after 12 h the virus-containing medium was collected. Fresh medium was added and the supernatant was collected every 24 h for the following 4 days. The viral supernatant was stored at −80° C. immediately after collection.

Viral stock were concentrated by ultracentrifugation of the supernatant (19,000 rpm, Beckman SW28 rotor) for 140 min at room temperature and the resulting viral pellets were resuspended in 1–3 ml of phosphate-buffered saline. Aliquoted viral stocks were titered with 293 cells and the remaining samples were stored at −80° C.

All lentiviral vector supernatants were assayed for the presence of replication competent retrovirus (RCR) by infection of phytohemagglutinin-stimulated human peripheral blood mononuclear cells, with subsequent analysis of the culture medium for p24 gag by ELISA. RCR was not detected in any of the viral supernatants produced.

EXAMPLE 3
Lentivirus Vector Transduction

Figure 2:
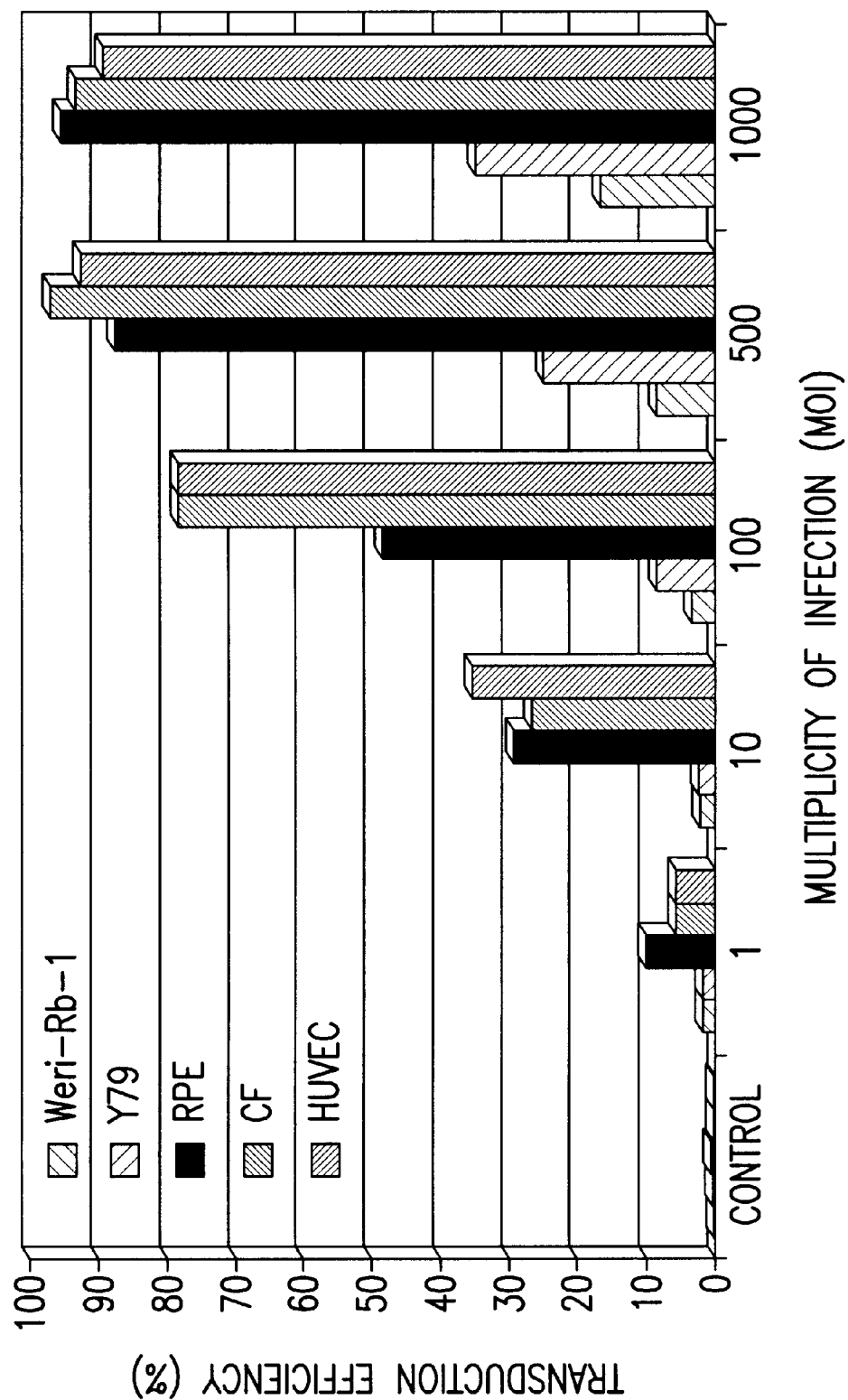
FIG. 2 shows in vitro transduction of the following human cell lines: human retinal pigment epithelial cells (RPE), human umbilical vein endothelial cells (HUVEC), Choroidal fibroblasts (CF), human retinoblastoma (retinal-derived) cells (Weri-Rb-1 and Y79). These cell lines were transduced with lentiviral particles containing a marker gene (the enhanced green fluorescent protein gene) and the fraction of cells expressing the marker gene were determined by fluorescent-activated cell sorting. A dose-response is noted as more cells are transduced with greater numbers of lentiviral particles (multiplicity of infection—MOI)
Figure 3A:
FIG. 3A demonstrates lentiviral transduction of cultured retinal pigment epithelial cells. Marker gene (eGFP) expression results in green, fluorescent cells.

Supernatants containing 2×10$^6$ replication-deficient lentiviral particles/ml were generated by the transfection of 293T cells with the lentivirus vector described above. Cells were cultured with the viral particles for 24 hours and then recovered in normal media for four days prior to the determination of GFP expression by fluorescent-activated cell sorting (FIGS. 2–3).

Transduction efficiency was measured as a function of multiplicity of infection with MOIs ranging from 1 to 1000. Results of in vitro transduction of a number of human cell lines demonstrate a positive correlation between MOI and transduction efficiency as more cells were transduced with increasing number of lentiviral particles (FIG. 2).

Figure 4:
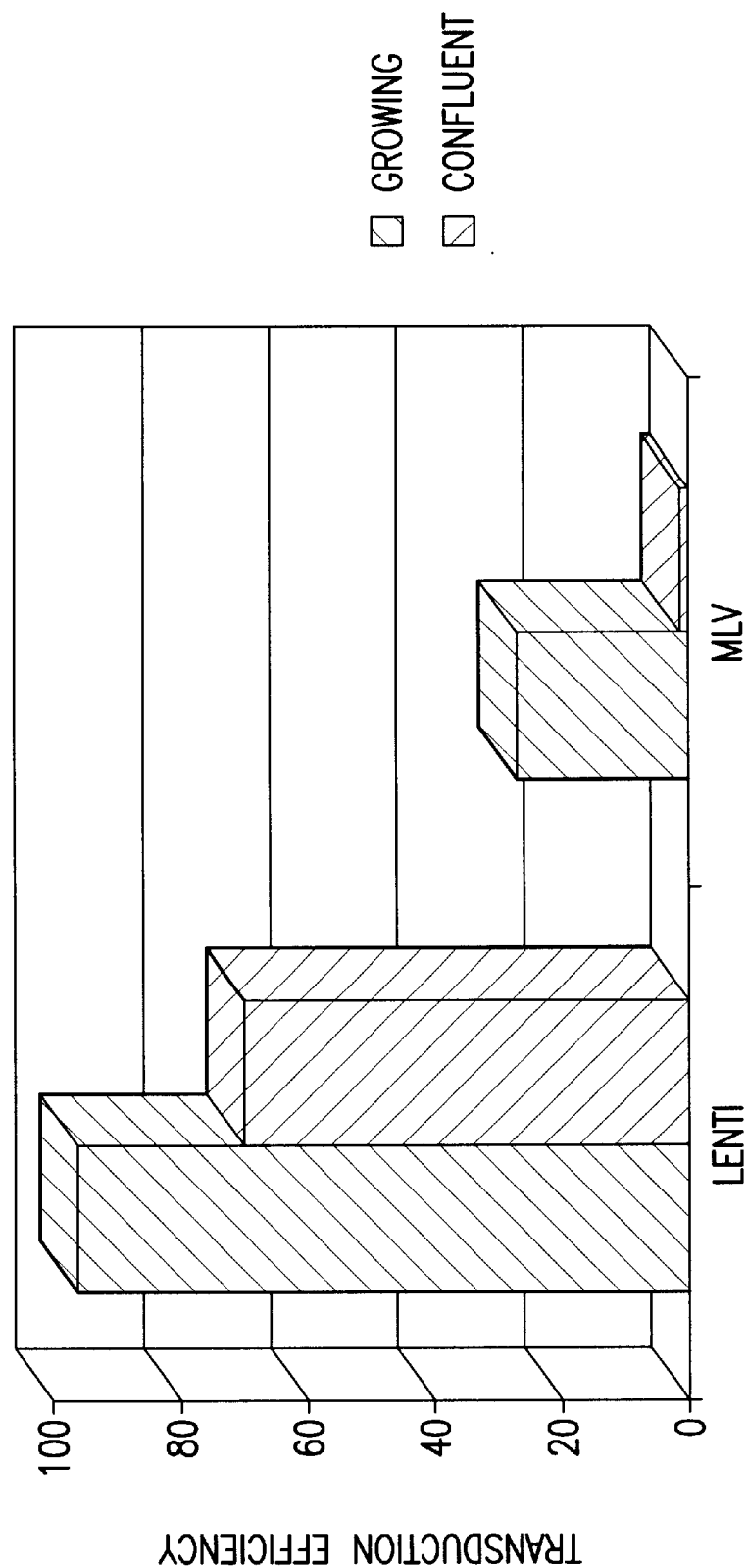
FIG. 4 illustrates mitotic activity and transduction efficiency in human retinal pigment epithelial cells. Human retinal pigment epithelial cells were transduced by lentiviral or murine leukemia viral (MLV) vectors. Cells were mitotically inactive (confluent) or mitotically active (growing) at the time of exposure to vector. These results demonstrate the superior ability of lentiviral vectors over other retroviral vectors to transduce non-dividing cells.

The ability of the lentiviral vector to transduce non-dividing cells was examined. Human retinal pigment epithelial cells were transduced by lentiviral or murine leukemia viral vectors. Cells were mitotically inactive (confluent) or mitotically active (growing) at the time of exposure to vector. Results shown in FIG. 4 demonstrate a superior ability of lentiviral vectors over other retroviral vectors to transduce non-dividing cells. The lentiviral vector was also highly efficient in transducing human fetal cells as compared with non-lentiviral retroviral vector (FIG. 6).

Figure 5A:
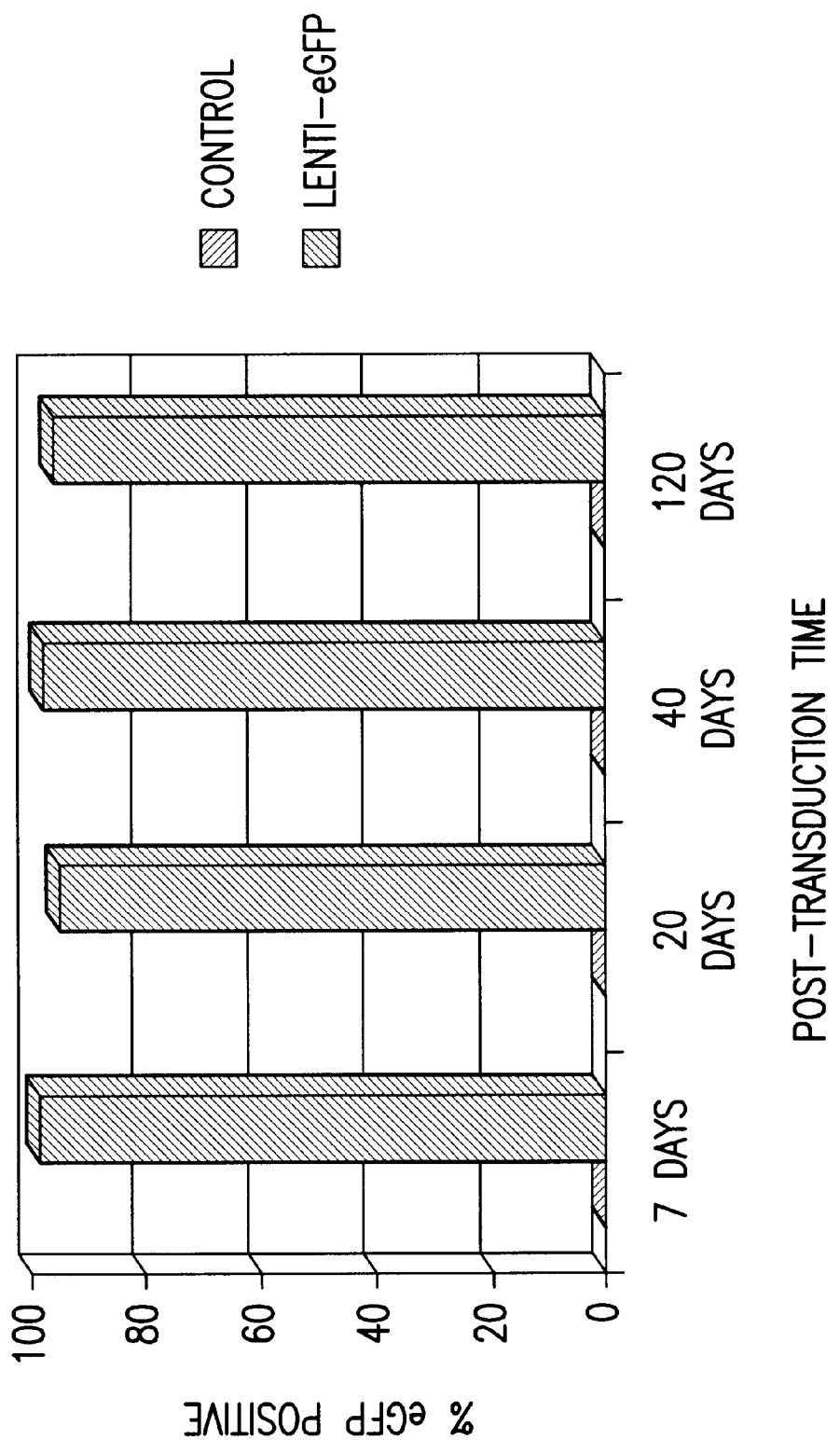
FIG. 5A depicts the stability of eGFP expression in these cells as well as a lack of selection for, or against, lentivirally transduced cells (the fraction of transduced cells remains constant over time).
Figure 5B:
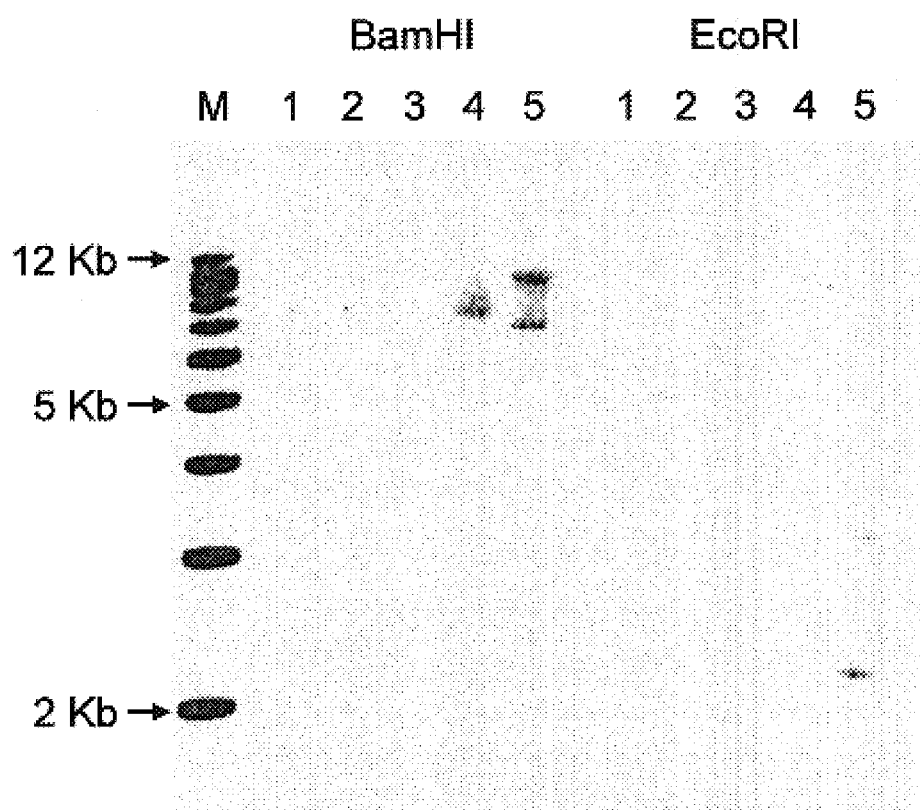
FIG. 5B is the result of Southern analysis on 5 clonal populations of cells. Lane 1 contains genomic DNA from the non-transduce parental line. Lanes 2 and 3 contain DNA from cells which were exposed to vector but were not green (non-transduces). Lanes 4 and 5 contain DNA from transduced, green cells. Cells remain e-GFP positive as the result of genomic integration.
Figures 7A, 7B:
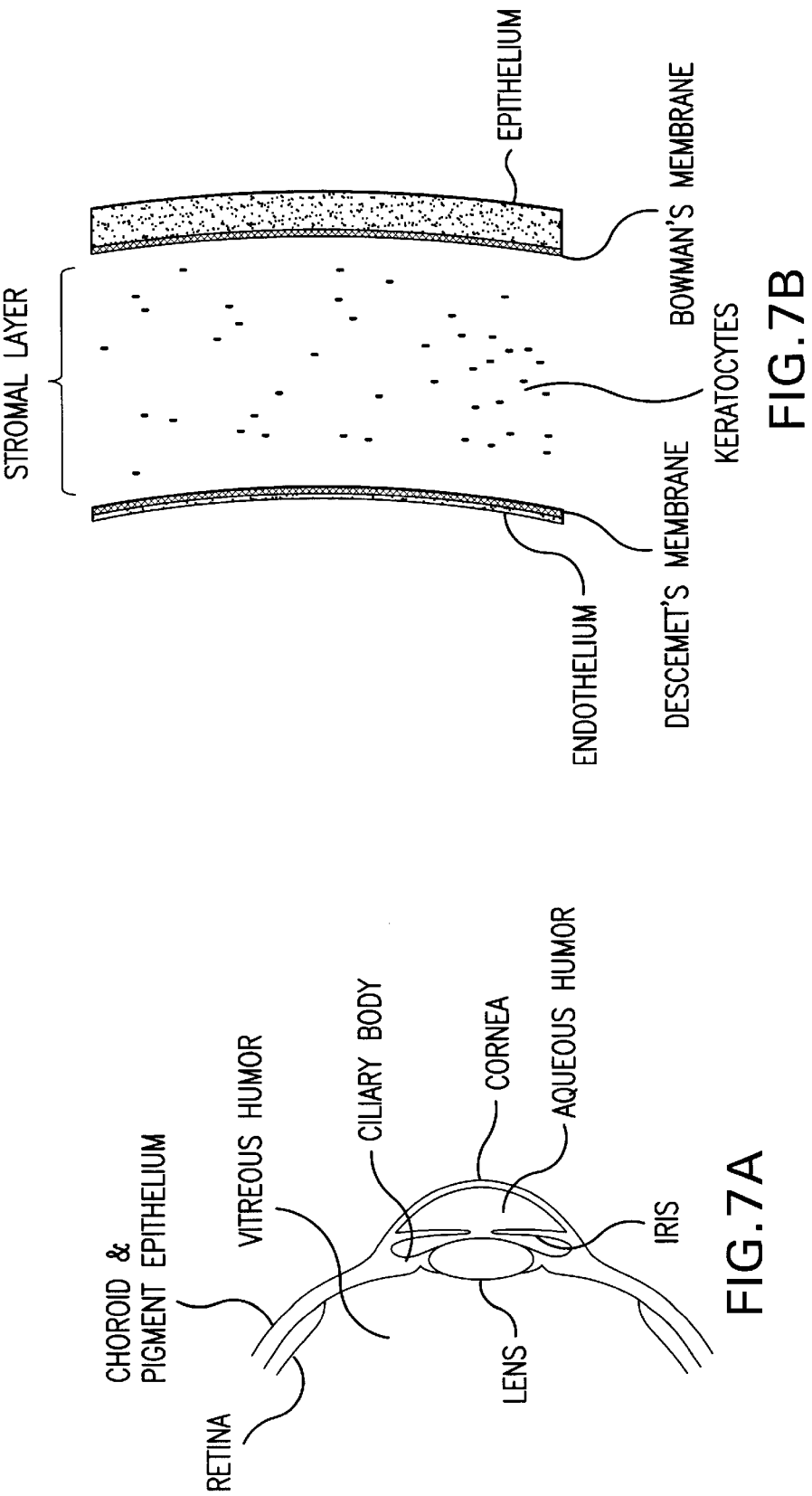
FIG. 7A-F demonstrates corneal transduction.
Figure 7C:
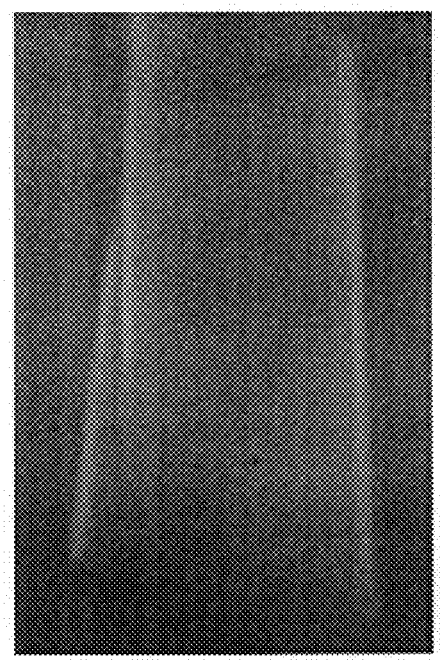
Figure 7D:
Figure 7E:
Figure 7F:
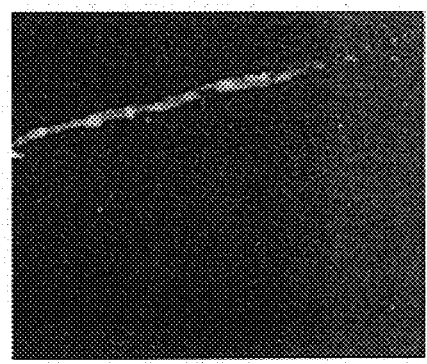

To determine the duration of eGFP transgene expression, cells transduced by the lentiviral vector were tested over a period of 120 days. Results of Southern Blot analysis on clonal populations of transduced cells indicate that the lentiviral-eGFP vector was integrated into the host genome (FIG. 5B). Expression of the integrated eGFP transgene was stable over 120 days and confer no selective advantage for or against the transduced cells (FIG. 5A).

EXAMPLE 4
Corneal Transduction in situ

Human corneal buttons obtained at the time of corneal transplant surgery were used to demonstrate the ability of lentiviral vectors to transduce these mitotically inactive cells with the marker gene enhanced green fluorescent protein gene (FIG. 7). Endothelial cells attached to Descemet's membrane were peeled away from the transduced corneal tissue, and examined by light and fluorescent microscopy. The corneal endothelium was positive for eGFP, indicating that efficient gene transfer and expression were attained (FIG. 7B). Efficient in situ transduction and eGFP expression in the epithelial layer was also observed (FIG. 7C).

In conclusion, these results indicate that a replication-defective lentiviral vector is able to transfer efficiently transgene to human corneal endothelial and epithelial cells in situ, and achieve long-term transgene expression. This vector could be useful in the treatment of corneal endothelial or epithelial disorders and can be applied to modify the genetic makeup of a donor cornea tissue ex vivo before transplantation in such a way as to modulate permanently the process of allograft rejection.

EXAMPLE 5
Growth Suppressor Therapy for Ocular Proliferative Disease

Figure 8:
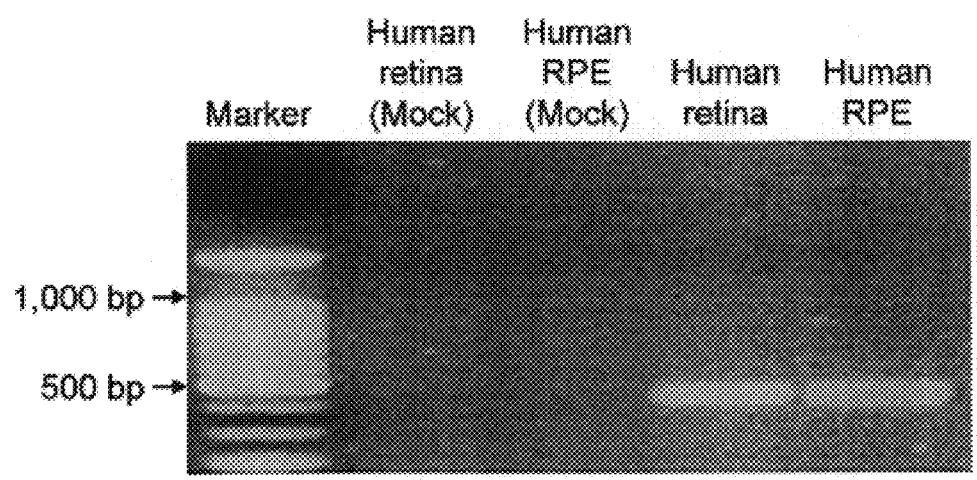
FIG. 8 provides an example of lentiviral gene transfer of a gene whose deficiency results in human disease. Normal human retinal or retinal pigment epithelial (RPE) tissue, surgically excised at the time of enucleation for retinoblastoma, was exposed to lentiviral vectors which either lacked a therapeutic gene (Mock) or contained the human peripherin gene. This gene, when genetically deficient in humans is known to result in a wide variety of disabling phenotypes. Results of reverse transcriptase-assisted polymerase chain reaction (rt-PCR) employing primers designed to recognize only the transferred peripherin gene were shown. The expression of human peripherin in human retinal and RPE was clearly demonstrated.

Human peripherin gene was used as one example of therapeutic gene. Genetic deficiency of peripherin gene in humans is known to result in a wide variety of disabling phenotypes. Normal human retinal or retinal pigment epithelial (RPE) tissue surgically excised at the time of enucleation for retinoblastoma was exposed to lentiviral vectors which either lacked a therapeutic gene or contained the human peripherin gene. Results in FIG. 8 demonstrate that the peripherin gene was efficiently transferred to human retinal tissue by the lentiviral vector.

Figure 9:
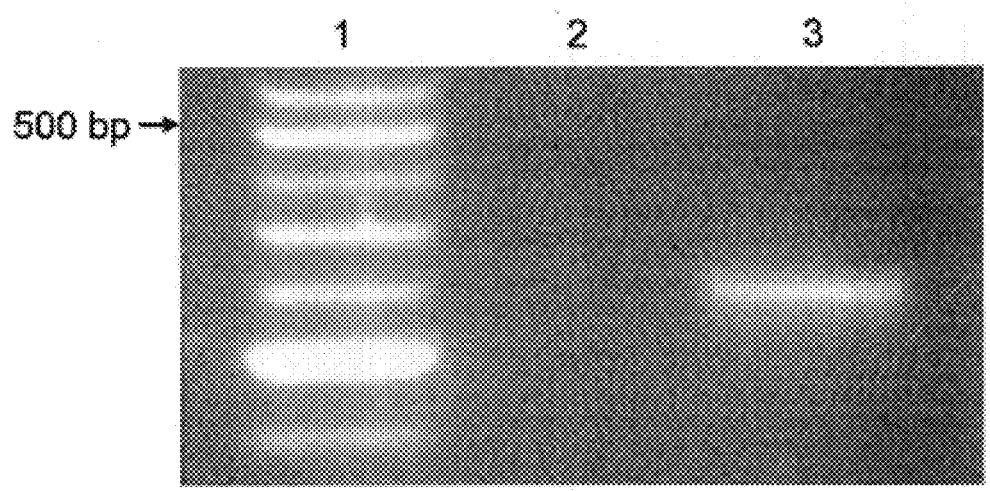
FIG. 9 demonstrates lentiviral-mediated expression of CA-rb mRNA. This shows the results of a reverse transcriptase-assisted polymerase chain reaction (rt-PCR) employing primers designed to recognize only the constitutively active form of the retinoblastoma gene. Lane 1: marker, Lane 2: reaction results with RNA isolated from lentiviral-eGFP transduced cells, Lane 3: reaction results with RNA isolated from lentiviral-CA-rb transduced cells. The reaction product was of the expected size.
Figure 10:
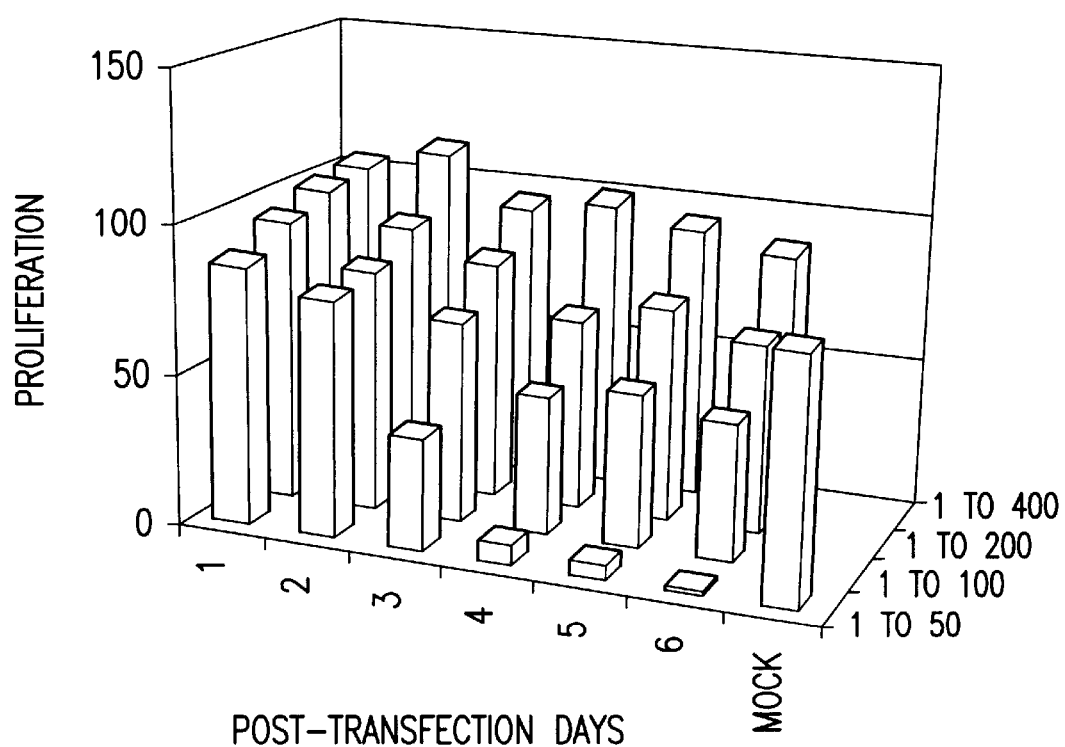
FIG. 10 shows the inhibitory effect of lentiviral CA-rb on human retinal and choroidal cell division. Cells were exposed to decreasing dilutions of a single lentiviral stock (1:400 dilution to 1:50 dilution) and growth was compared with cells exposed to lentiviral vectors which did not contain the CA-rb gene. An inhibitory effect on cell division was clearly seen over time and this effect was dose-dependant.
Figure 11:
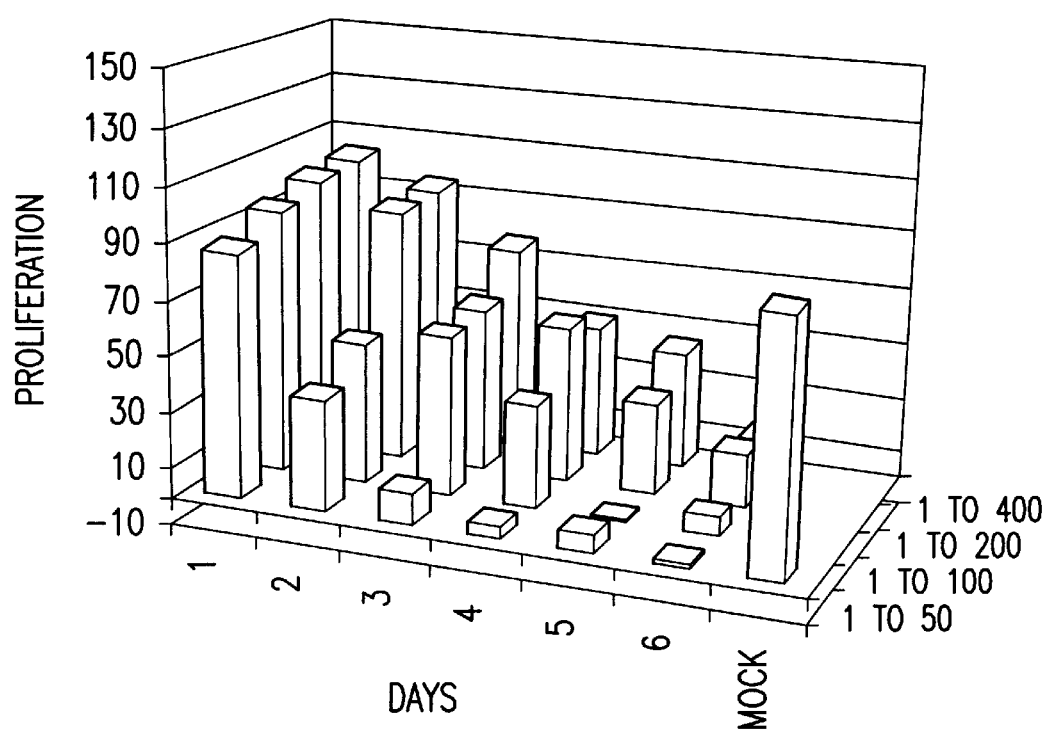
FIG. 11 shows the inhibitory effect of lentiviral CA-rb on human lens epithelial cell division. Cells removed from human eyes at the time of cataract extraction were exposed to decreasing dilutions of a single lentiviral stock (1:400 dilution to 1:50 dilution) and growth was compared with cells exposed to lentiviral vectors which did not contain the CA-rb gene. An inhibitory effect on cell division was clearly seen over time and this effect was dose-dependant.

As an another example of therapeutic gene transfer, the constitutively active form of the retinoblastoma gene (CA-rb) was used. The lentiviral vector disclosed herein mediated efficient transfer of the constitutively active form of the retinoblastoma gene (FIG. 9). The transferred CA-rb gene exhibited dose-dependent inhibitory effects on the proliferation of human retinal and choroidal cells (FIG. 10) and human lens epithelial cells (FIG. 11).

Figure 12A:
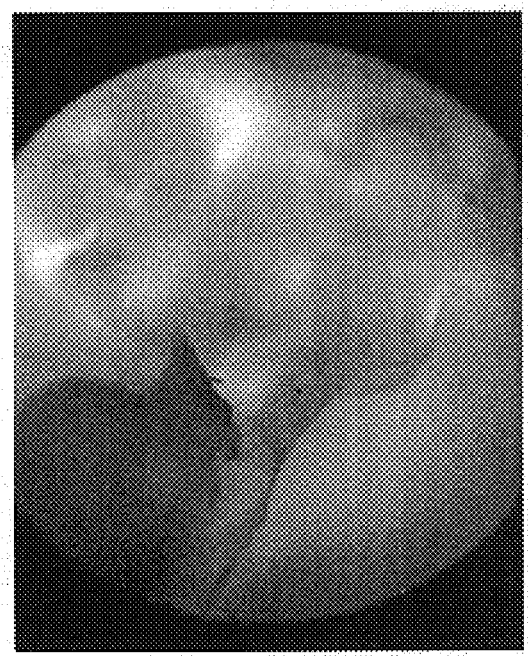
FIG. 12 shows the in vivo inhibitory effects of lentiviral CA-rb on blinding intraocular cellular proliferation. Proliferative vitreoretinopathy was induced in three sets of rabbits. One set was not treated, one set was treated with lentiviral vectors lacking the CA-rb gene and the last set was treated with intravitreally-delivered lentiviral CA-rb. Proliferative vitreoretinopathy and retinal detachment was noted in the first two sets at high frequency (>90%). The fraction of animals that went on to retinal detachment was significantly lower in the set treated with CA-rb (26%). Shown here are two retinal photographs. The eye on the left had a completely attached retina and was treated with CA-rb. The eye on the right had a completely detached retina, the consequence of intraocular vitreoretinopathic cellular proliferation, and was treated with lentiviral vectors lacking the CA-rb gene.
Figure 12B:
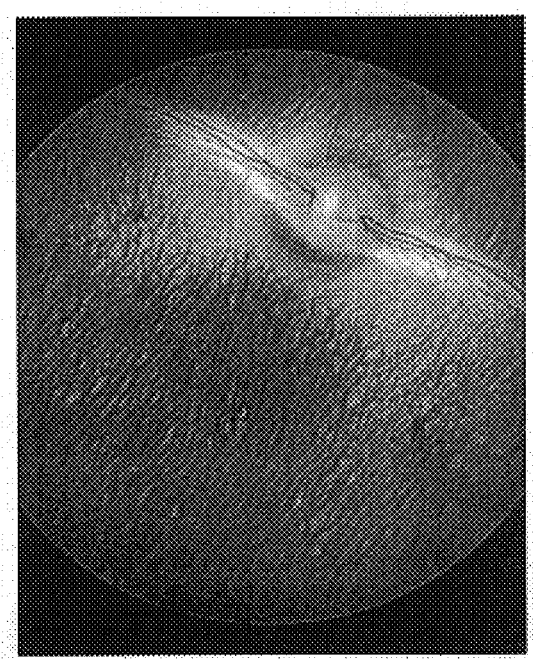

The constitutively active form of the retinoblastoma gene transferred by the lentiviral vector also inhibited intraocular cellular proliferation in vivo. Two models of intraocular proliferative disease (proliferative vitreoretinopathy and post-lens extraction posterior capsular opacification) were tested in vivo. Proliferative vitreoretinopathy was induced in three sets of rabbits (FIG. 12). One set was not treated, one set was treated with lentiviral vectors lacking the CA-rb gene and the last set was treated with intravitreally-delivered lentiviral CA-rb. Proliferative vitreoretinopathy and retinal detachment was noted in the first two sets at high frequency (>90%), whereas the fraction of animals that went on to retinal detachment was significantly lower in the set treated with CA-rb (26%).

Figure 13:
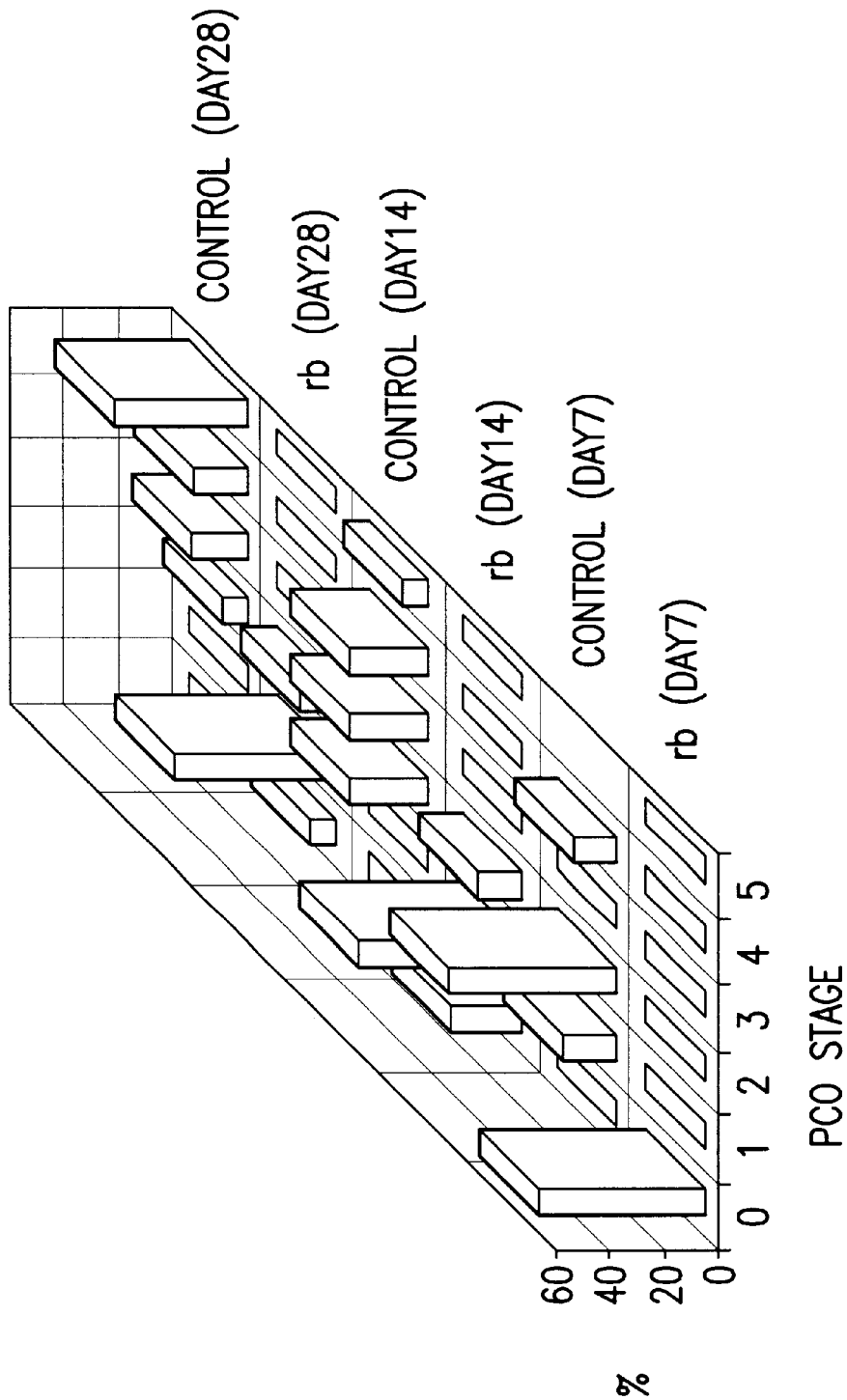
FIG. 13 shows the in vivo inhibitory effect of lentiviral CA-rb on the process of post-lens extraction posterior capsular opacification. Three sets of rabbits underwent standard phacoemulsfication to remove the native crystalline lens. The first set (group 1) was subsequently treated with nothing and the second two sets were treated with either empty lentiviral constructs (no therapeutic gene, group 2) or with lentiviral CA-rb (group3) delivered into the intact lens capsular bag at the time of closure of the cataract wound. Animals were serially examined for the presence of posterior capsular opacification. The presence of opacification was graded on a 1 to 5 scale where 1 represented no opacification and 5 represented opacification severe enough to preclude visualization of the retina with indirect binocular ophthalmoscopy. There were no statistically different results obtained between groups 1 and 2 (no treatment and empty vector). The graph here shows a striking inhibitory effect of lentiviral CA-rb on the development of posterior capsule opacification. By day 28, control animals had an average opacification score of 4.4 while animals treated with lentiviral CA-rb had an average opacification score of 2.1.

Results shown in FIG. 13 demonstrate in vivo inhibitory effect of lentiviral CA-rb on the process of post-lens extraction posterior capsular opacification. Three sets of rabbits underwent standard phacoemulsfication to remove the native crystalline lens. The first set (group 1) was subsequently treated with nothing and the second two sets were treated with either empty lentiviral constructs (no therapeutic gene, group 2) or with lentiviral CA-rb (group 3) delivered into the intact lens capsular bag at the time of closure of the cataract wound. Animals were serially examined for the presence of posterior capsular opacification. The presence of opacification was graded on a 1 to 5 scale where 1 represented no opacification and 5 represented opacification severe enough to preclude visualization of the retina with indirect binocular ophthalmoscopy. There were no statistically different results obtained between groups 1 and 2 (no treatment and empty vector), whereas a striking inhibitory effect of lentiviral CA-rb on the development of posterior capsule opacification was observed. By day 28, control animals had an average opacification score of 4.4 while animals treated with lentiviral CA-rb had an average opacification score of 2.1.

EXAMPLE 6
"Two Gene" Lentiviral Vector

A new lentiviral vector that incorporated an IRES (internal ribosome entry site) element between two cloning sites was constructed. The IRES element allows mRNA-ribosome binding and protein synthesis. This backbone can accommodate two different expressible genes. A single message is produced in transduced cells; however, because of the IRES element, this message is functionally bi-cistronic and can drive the synthesis of two different proteins. In this fashion a number of potentially therapeutic genes (Table 1) can be linked to a marker gene (e.g. the enhanced green fluorescent gene—eGFP gene) so that transduced cells will simultaneously be marked and able to express the therapeutic gene of interest. Marked cells can then easily be isolated in vitro and observed in vivo.

Figure 14:
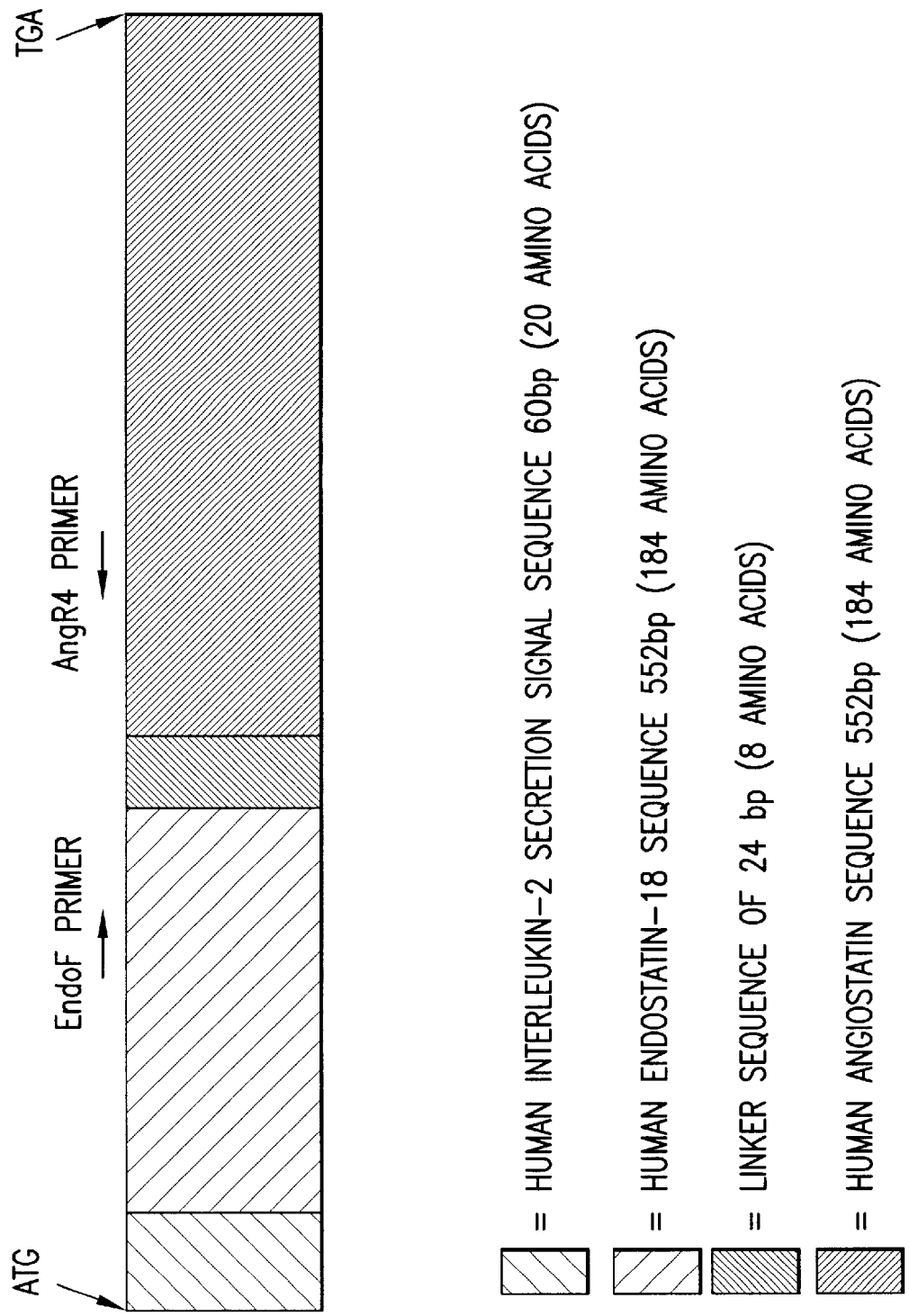
FIG. 14 shows a map for a endostatin-18/angiostatin fusion gene delivered by lentiviral vector.

The lentiviral vector can also carries fusion genes that combine the functional motifs of different angiostatic proteins via an elastin peptide linker. These fusion proteins combine two potent angiostatic genes to increase the suppression of tumor angiogenesis. Since these molecules operate through different mechanisms, their combination may result in additive or synergistic effects. Examples of angiostatic fusion proteins include, but are not limited to, the fusion of endostatin 18 and angiostatin (endo/ang, FIG. 14), endostatin18 and the kringle 5 motif of plasminogen (endo/k5), fusion of endostatin 18 and PEX, as well as the fusion of monokine-induced by interferon-gamma and the interferon-alpha inducible protein 10 (MIG/IP10). Genetic maps for a number of lentiviral vectors carrying various therapeutic genes are shown in FIGS. 15–31.

Figure 32:
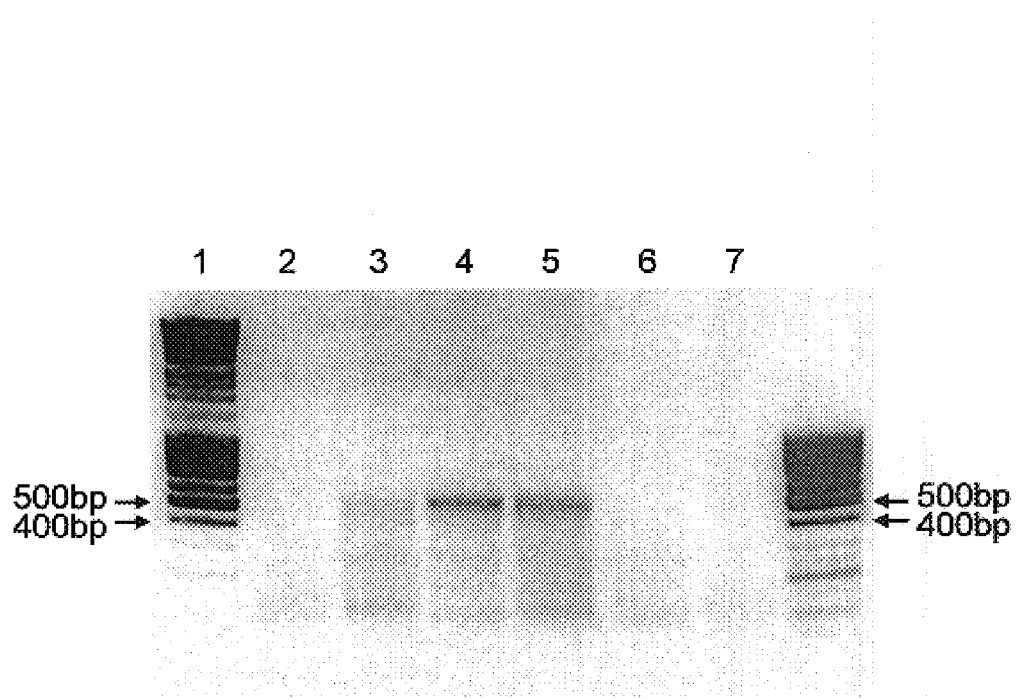
FIG. 32 shows RT-PCR of mRNA isolated from human dermal microvascular endothelial (hDMVE) cells transduced with the endostatin-18/angiostatin fusion gene. Lane1: 1000/100 bp ladder mix; lane 2–5: RT-PCR from mRNA isolated from hDMVE cells transduced with 1 µl, 5 µl, 10 µl and 20 µl of pHR'-eF1α/HTLV-Endo::Ang-IRES-eGFP virus supernatant from a single well of a 12 well plate; lane 6: RT-PCR from mRNA isolated from hDMVE cells incubated with 20 µl of PBS; lane 7: negative control (H2O as template for RT-PCR); lane 8: 100 bp ladder.

Naive cells known to not express the therapeutic gene were exposed to a lentiviral vector carrying one of the aforementioned fusion genes for 24 hours. Two days following this exposure, RNA was isolated from these cells and was tested for transgene expression by reverse-transcriptase assisted polymerase chain reaction (RT-PCR). FIG. 32 shows a positive RT-PCR product for the endostatin-18/angiostatin fusion gene from mRNA isolated from human dermal microvascular endothelial cells, thereby demonstrating lentiviral-mediated gene transfer in vitro.

TABLE 1

Candidate Therapeutic Genes

ANGIOGENESIS INHIBITORS
MMP inhibitors hTIMP1
hTIMP2
hTIMP3
hTIMP4
hPEX
Endostatin hEndo XV
hEndo XVIII
Angiostatin hKl-5
Anti-VEGF hFLTs
hFLK-1 (KDR)
Chemokines Mig
IP-10
TUMOR SUPPRESSORS hp16
hp21
hp27
hp53
hPTEN TABLE 1-continued Candidate Therapeutic Genes

APOPTOSIS hBad
hBak
hBax-a
hBc12-a
hBc1XL
hBik
hGAX

EXAMPLE 7

Animal Model of Neovascularization

Following the demonstration of in vitro lentiviral-mediated gene transfer as shown above, the ability to inhibit neovascularization in vivo was then examined. Neovascularization was induced in rabbit corneal tissues in the following fashion:

Creation of a Corneal Intrastromal Micropocket and Insertion of Nylon Mesh Impregnated with Lentivirus Rabbits underwent general anesthesia with Isoflourane (4 L/Min) and Oxygen (2 L/Min) by masking. One drop of Proparacaine was placed in the fornix for topical anesthesia. The Isoflourane was reduced to 2.5 L/Min. Betadine was placed in the fornix for 30 sec. and rinsed out with BSS (balanced saline solution, Alcon Inc). A lid speculum was placed in the eye. A 2.8 mm microkeratome was used to enter the corneal stroma at 12 o'clock. This intrastromal incision was developed into a 5×5 mm intrastromal pocket with a McPherson forceps and Iris Sweep instrument by sweeping back-and-forth. The 12 o'clock incision was opened up on either side so that the opening was 4.5 mm with Vannas scissors. A 4×4 mm Amersham hybridization nylon mesh (Amersham Bioscientist RPN 2519) impregenated with 10 μL of lentivirus was inserted into the pre-formed pocket. A drop of tobramycin was placed on the cornea. Isoflourane was discontinued and nasal oxygen was increased to 4 L/Min. In this fashion, rabbits were successfully brought out of general anesthesia after 20 minutes and returned to their cages with normal vital functions.

Rabbits received 0.2 cc of buprenex (0.3 mg/cc) SQ bid for two days for analgesia. Rabbits also received one drop of atropine and one drop of tobramycin for two days for post-op cycloplegia and antibiotic care. On the first post-operative day each rabbit received a drop of topical proparacaine for anesthesia and the nylon mesh was removed from the corneal intrastromal pocket with a 0.12 forceps. Post surgical pain control and care was monitored daily for two weeks.

Alkali Induced Neovascularization

Figure 33:
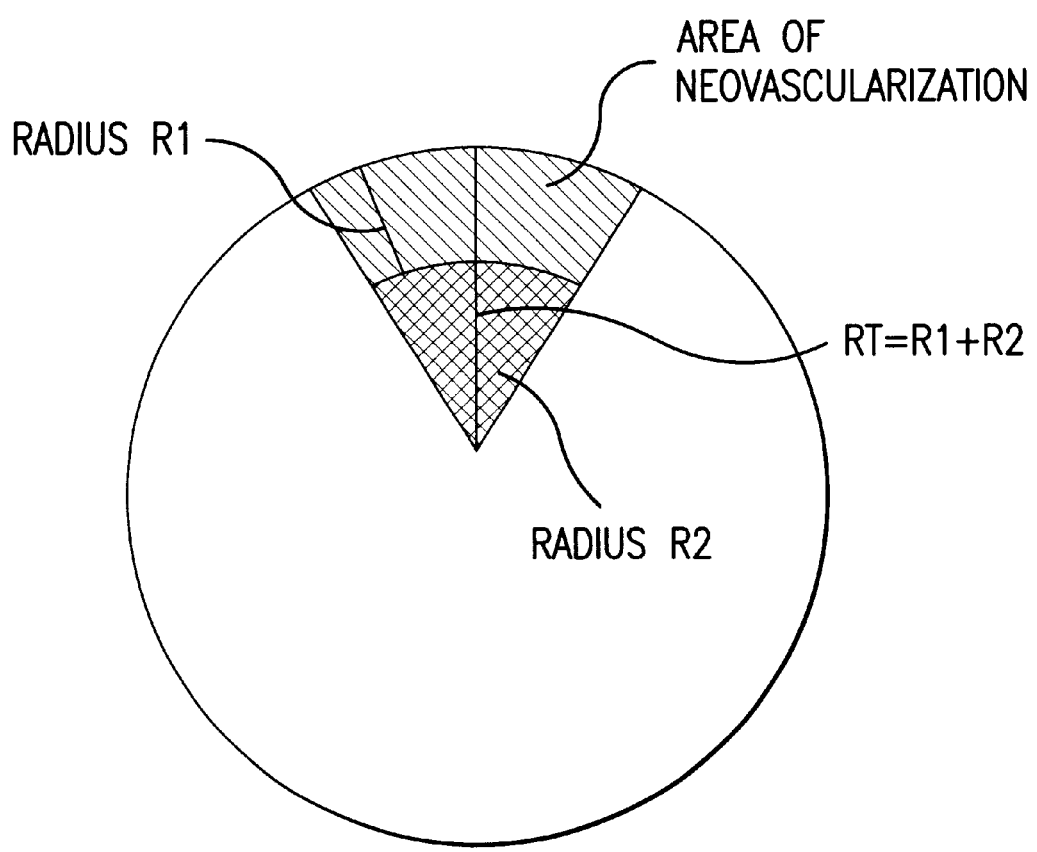
FIG. 33 shows a standardized method of evaluation for corneal neovascularization after alkali burn. The formula for the area of neovascularization is derived by calculating the area of the larger sector bounded by radius RT and subtracting the smaller sector bounded by radius R2. The area of the larger sector bounded by radius RT is the number of clock hours divided by 12 and multiplied by $\pi RT^2$. The area of the smaller sector bounded by radius R2 is the number of clock hours divided by 12 and multiplied by $\pi(R2)^2$. The resulting area derived from the subtraction of the two sectors would be the area of neovascularization.
Figure 34A:
FIG. 34A shows a fluorescent photomicrograph demonstrating the presence of eGFP expression in a micropocket.
Figure 34B:
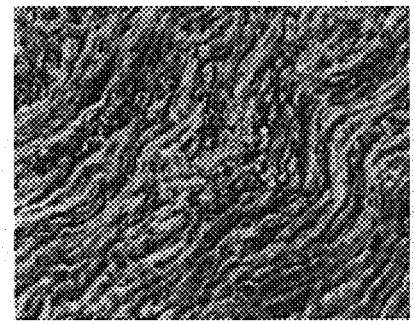
FIG. 34B shows a non-fluorescent photomicrograph of the same tissue as shown in A.
Figure 34C:
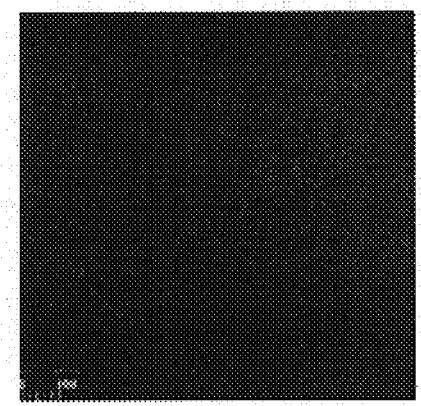
FIG. 34C shows a fluorescent photomicrograph of a similarly processed tissue from an untreated animal.

Two weeks after initial surgery, corneas were exposed to 6 mm Whatman #3 filter disks saturated with 20 μl of 1.0M NaOH for 1 minute. All corneas were then copiously washed with BSS. Rabbits received one drop of atropine and one drop of tobramycin for two days for post-op cycloplegia and antibiotic care. Digital photo-documentation was carried out to record the neovascular response. The neovascular response was measured by slit-lamp examination noting the clock hours and the length of vessels on post-trauma day 1, 3, 5, 7, and 10. Neovascularization was quantified by calculating the area of vessel growth as described in FIG. 33. Confocal microscopy was performed to document the expression of enhanced green fluorescent protein, the marker gene included in the lentiviral bicistronic message. FIG. 34 shows photomicrographs demonstrating the presence of eGFP within the corneal micropocket in animals treated with the lentiviral vector.

EXAMPLE 8

Inhibition of Neovascularization by the Endo/K5 Fusion Gene

The present example examines whether lentiviral mediated expression of an Endostatin:Kringle-5 fusion gene has an inhibitory effect on neovascularization and failure of corneal transplants.

More than 30,000 corneal transplants are performed each year in the United States. This is more than all heart, kidney, and liver transplants combined. Corneal transplantation is one of the most successful transplants in humans, with success rate exceeding 90%. Still there are a significant number of corneal transplants that undergo rejection and graft failure every year. The need for regrafting a failed transplant is one of the top two indications for corneal transplantation in many centers in the U.S., competing with pseudophakic bullous keratopathy in frequency. The major risk factors for rejection are prior corneal transplantation, glaucoma, and preoperative corneal vascularization. Prevention of corneal neovascularization would be a pivotal step towards inhibiting graft failure and rejection, and the development of a biological agent to combat pro-angiogenic stimulation would be a useful tool.

Endostatin, a 20 kDa C-terminal fragment of Collagen XVIII, has been shown to be an endogenous inhibitor of angiogenesis and tumor growth in a hemangioendothelioma model in rats. Endostatin impedes proliferation and migration by down regulating the expression of genes involved in cell growth, anti-apoptosis and angiogenesis specifically within endothelial cells. Angiostatin, a protein derived from proteolytic cleavage of an internal fragment of plasminogen, contains up to 4 kringle domains and inhibits angiogenesis-dependent tumor growth. Kringle-5 of plasminogen shares 46%–57% amino acid identity to each of the four kringle domains of angiostatin and is a more potent inhibitor of basic fibroblast growth factor-stimulated angiogenesis than angiostatin alone. Kringle-5 acts specifically on endothelial cells by inhibiting cell migration. The angiostatic fusion protein consisting of mouse Endostatin and mouse Angiostatin has been shown to have a more potent biological effect than either gene product alone in an in vitro cancer model. In this example, the biologically active domains of human endostatin 18 and human kringle-5 were linked to make the fusion protein Endo::K-5 for the purpose of producing a protein able to inhibit both endothelial cell proliferation and migration.

Lentiviral Production

Figure 17:
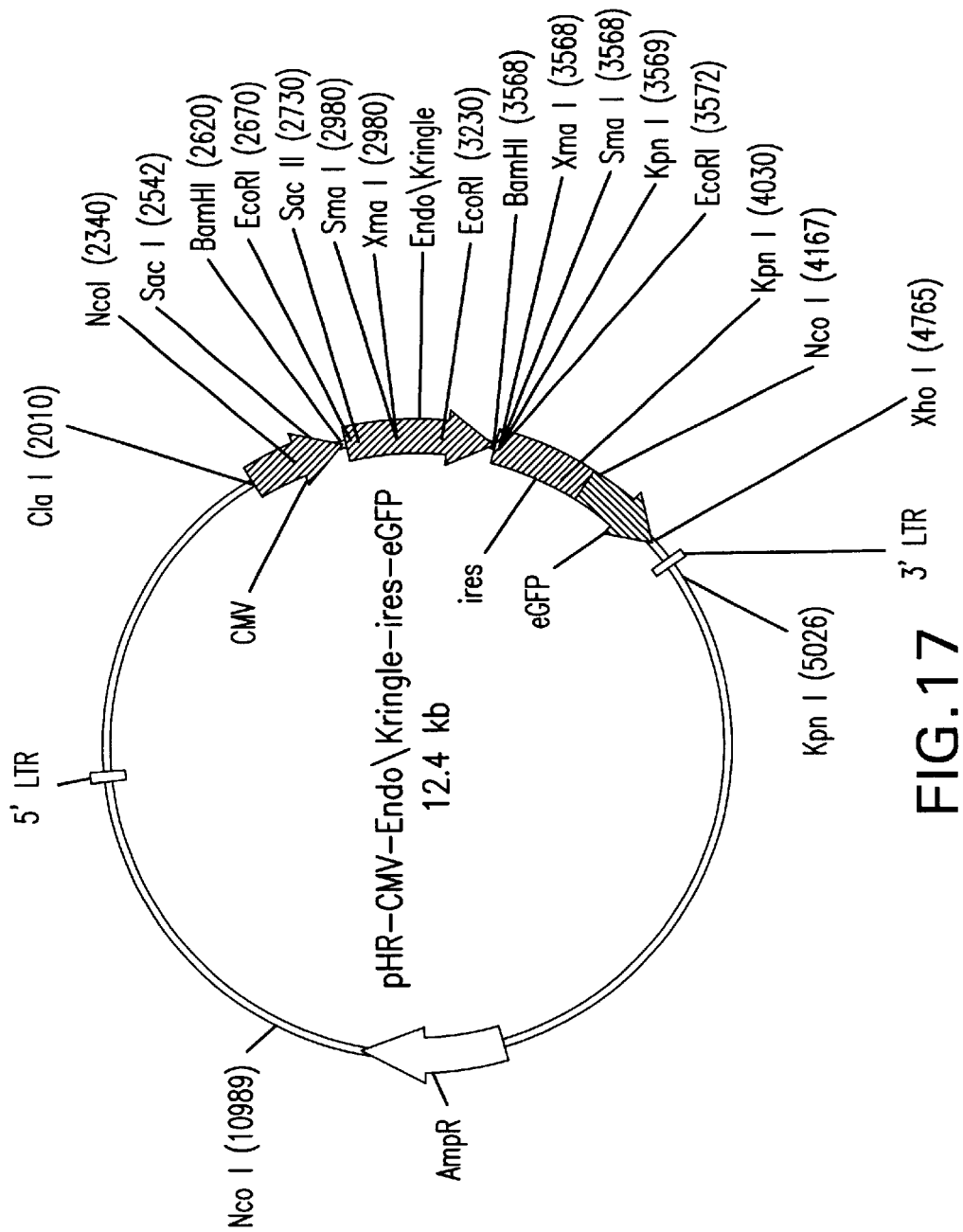
FIG. 17 shows a map for the lentiviral vector pHR-CMV-Endo/Kringle-ires-eGFP carrying an endostatin/kringle fusion gene.

An Endostatin-Kringle-5 (Endo-Kr5) fusion cDNA was amplified by PCR from the EK-5 pBlast vector (Invivogen) using the forward primer (5' CTGAGGGATCCGGC-GAAGGAG 3', SEQ ID NO. 1) containing a BamH1 site and the reverse primer (5' CAATGTATCGGATCCTGTC-GAGCTAGC 3', SEQ ID NO. 2) containing a BamH1 site. This fusion gene encodes 20 amino acids from the human Interleukin-2 secretion signal, amino acids Ala 1333-Lys 1516 from the human Collagen XVIII gene (endostatin), an 8 amino acid elastin linker motif VPGVGTAS (SEQ ID NO. 3) and amino acids Pro 466-Asp 566 from the human plasminogen gene. The PCR fragment was digested with BamH1 and ligated into a lentiviral vector under the transcriptional control of the cytomegalovirus (CMV) promoter (FIG. 17). Construction of the Endo::K-5 fusion gene was confirmed by direct sequencing of the transgene insert.

Viral Assay

The presence of viral particles was confirmed with a p≧GAG antigen ELISA kit (Zeptometrix) as per manufacturer's instructions. To ensure the infectivity of the lentiviral reagent, 10, 50, and 100 µl of virus was placed into a six-well plate of human dermal microvascular endothelial cells (HDMEC) for 20 min at 37° C. Media 131 (Cascade Biologicals; Oregon) was then added and cells were incubated at 37° C., 5% $CO_2$ for 5 days, with media changes every other day. On day 5, RNA was isolated using Trizol (Gibco-BRL) and analyzed by standard RT-PCR. The forward primer (5' TCTGAGGGTCCGCTGAAGCCCGGGG3', SEQ ID NO.4) and reverse primer (5' CAAATGAAGGGGCCG-CAC 3', SEQ ID NO. 5) flanked the elastin linker region and thus would only amplify the fusion transcript.

Corneal Transplantation in Rabbits

Sixteen 7 mm trephined donor corneas were obtained from eight New Zealand White Rabbits. Each button was incubated for 18 hours at 37° C. in 2 ml of optisol (CHIRON) containing 50 µl Endo::K-5 lentivirus, 50 µl eGFP lentivirus, or 50 µl PBS.

General anesthesia was induced by mask-administration of isoflorane. Paracentesis was created and heparin and viscoelastic were instilled into the anterior chamber (AC). A Hessburg-Barron 7 mm trephine was used to remove the host corneal button. Host buttons were placed in optisol media containing viral or control supplements for transplantation the following day. A 7 mm-trephined corneal button treated, with Enod::K-5, eGFP, or PBS was sewn in with 16 interrupted 7-0 nylon sutures. 0.1 cc subconjuntival injections of Baytril (23 mg/cc) and Kenolog (40 mg/cc) were given. Postoperatively, all animals received a single dose of topical atropine (1%) and a single dose of carprofen at 2.5 mg/kg SQ, as well as tobramycin 1 drop twice a day for 5 days and Buprenex at 0.1 mg/kg SQ as necessary. No topical steroid drops were given post-operatively.

Measurement of Neovascularization and Evaluation of Graft Rejection

Neovascularization was followed by slit lamp examinations on post-operative days 5, 9, 12, 14, 16, 24, 28, and 36. Measurements of neovascularization were made with a portable slit lamp by a single masked observer/ophthalmologist. Vessel growth onto the clear cornea was noted in mm and number of clock hours. Neovascularization was quantified by calculating the wedge shaped area of vessel growth with the formula: Area=(clock hours/12) $\pi r^2$ (FIG. 33). In most cases, vessel growth did not span the entire wedge section. To correct for this, the area of the section void of vessel growth was subtracted from the total area (FIG. 33). Graft rejection was evaluated by portable slit-lamp. Graft failure was judged by the presence of persistent corneal graft edema with opacification of 100% of the graft. Serial photographs of the cornea were taken. Animals were sacrificed on postoperative days 9, 21, 30, & 40. Fresh corneal tissue was placed in either Trizol (Gibco-BRL) for RT-PCR or formalin for histopathologic study.

Results

Sixteen New Zealand white rabbits underwent sequential allogeneic penetrating keratoplasty in one eye. Ten rabbits received grafts soaked overnight in Optisol plus lentiviral vector carrying the endostatin/kringle 5 fusion gene. Three rabbits received grafts soaked with Optisol plus lentiviral vector carrying the eGFP marker gene. Three rabbits received grafts soaked with Optisol plus PBS.

Figure 35:
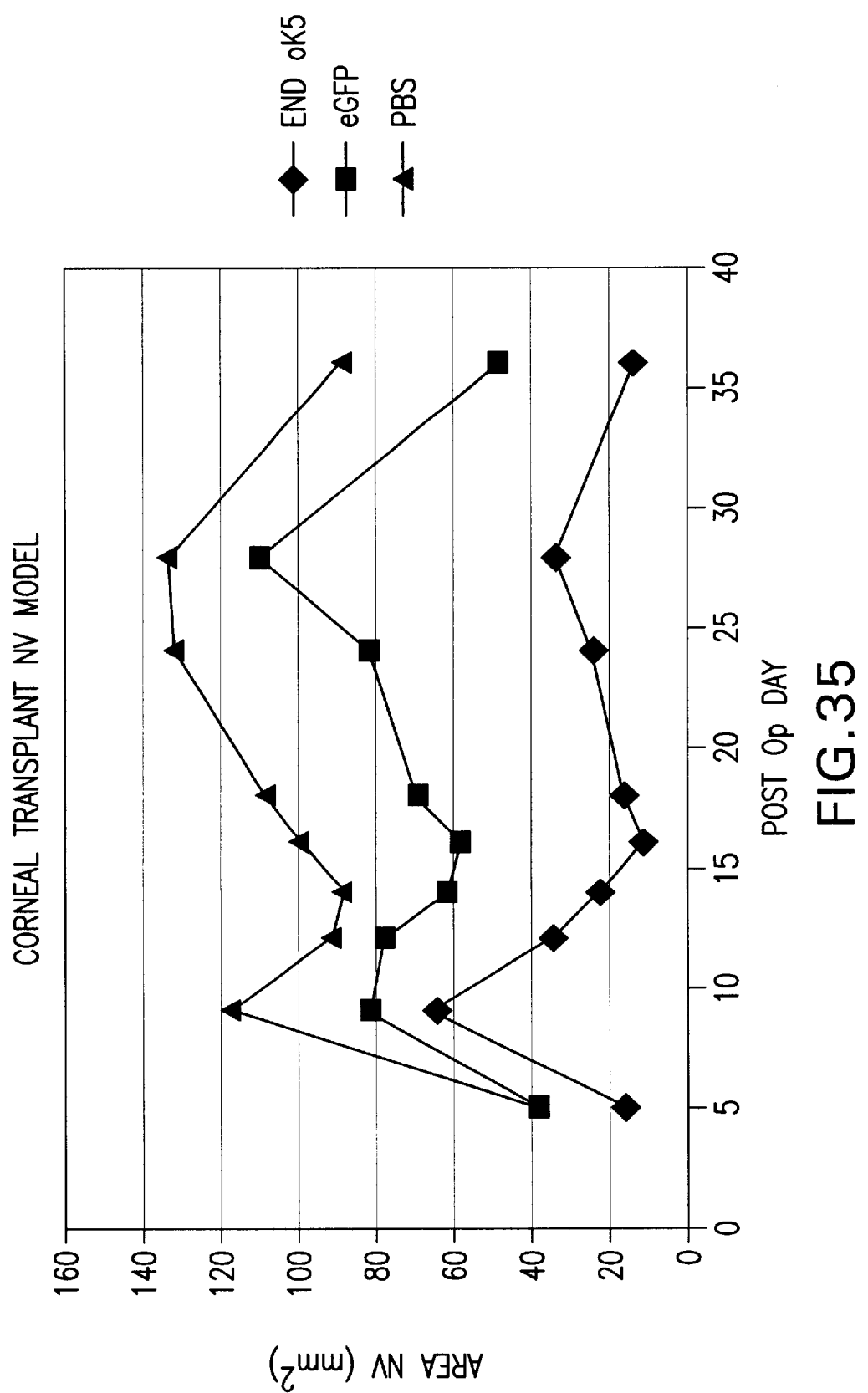
FIG. 35 shows inhibition of neovascularization in animals treated with a lentiviral Endo/K5 vector. The graph depicts average area of neovascularization in animals treated with PBS (n=3), lentiviral vector carrying the marker eGFP gene (n=3) or lentiviral vector carrying the Endo/K5 fusion gene (n=10).

Postoperative corneal neovascularization was significantly lower in lentiviral Endo::K-5 transplanted eyes than either lentiviral eGFP or PBS control eyes on postoperative days 5, 9, 12, 14, 16, 18, 24, 28 and 36 (FIG. 35). All PBS and all lentiviral eGFP treated corneas exhibited neovascular arborization into the graft bed. None of the ten Endo::K-5 treated corneas had new vessels into the graft. Three of three PBS and two of three eGFP treated corneas exhibited corneal opacification and graft failure, while none of the ten Endo::K-5 grafts completely opacified or failed by postoperative day 39.

All of the five grafts tested by RT-PCR for the presence of fusion gene transcripts were positive on postoperative days 30 and 40. All control and non-operative eyes were negative by fusion gene RT-PCR. Histopathology of the grafts revealed thicker, more edematous corneas in the control eyes when compared to the Endo::K-5 treated eyes. Analysis of serial sections revealed more neovascularization and basophilic inflammatory infiltrates in control eyes than in Endo::K-5 treated or non-operated eyes. Histopathologic study of a site of retained suture, often the location of an inflammatory infiltrate, was void of inflammatory cells in the examined Endo::K-5 cornea.

The success of corneal transplantation has expanded the indications for this surgery and has increased the number of keratoplasties performed annually. Despite the relative success of this surgery, graft rejection for a number of reasons remains a major problem. A major risk factor for graft rejection is neovascularization of the recipient corneal bed, the graft/host interface or, subsequently, of the graft itself. The development of new blood vessels into the graft is associated with high levels of inflammatory cells, plasma proteins, and cytokines within the graft and is often a presage to rejection and failure. Believing that neovascularization promotes rejection, investigators have long sought medical or surgical approaches to abort the process of corneal neovascularization.

The present example describes a successful approach to inhibit the development of post-penetrating keratoplasty neovascularization in a rabbit model. This approach is based upon the ability of lentiviral vectors to transduce corneal tissues ex vivo with genes known to be anti-angiogenic in animal models of tumor angiogenesis. A fusion gene that combines the human endostatin gene and the fifth kringle element of the human plasminogen gene as an inhibitor of new blood vessel growth was tested herein.

Treatment of corneal buttons with lentiviral Endo::K-5 was able to prevent new vessel growth onto the donor graft in all treated corneas. Histologic study revealed a marked decrease in inflammation in Endo::K-5 treated corneas. This included the areas around retained sutures, a commonly inflamed area. Furthermore, there was no evidence of graft failure as measured by persistent corneal edema and corneal opacification in Endo::K-5 treated corneas, whereas five of six control corneas exhibited evidence of opacification and failure. These results indicate that ex vivo lentiviral transduction of donor corneal tissue with a fusion anti-angiogenic gene prior to penetrating keratoplasty may increase the likelihood of long-term graft survival and can be a useful surgical adjunct.

EXAMPLE 9
Inhibition of Neovascularization by Kringle 1-5 Gene

Angiostatin K1-5, encoding a 55 kD protein composed of all five kringle domains of plasminogen, is created by protease action of plasmin on plasminogen. It is a potent anti-angiogenic factor in multiple models.

Figure 36:
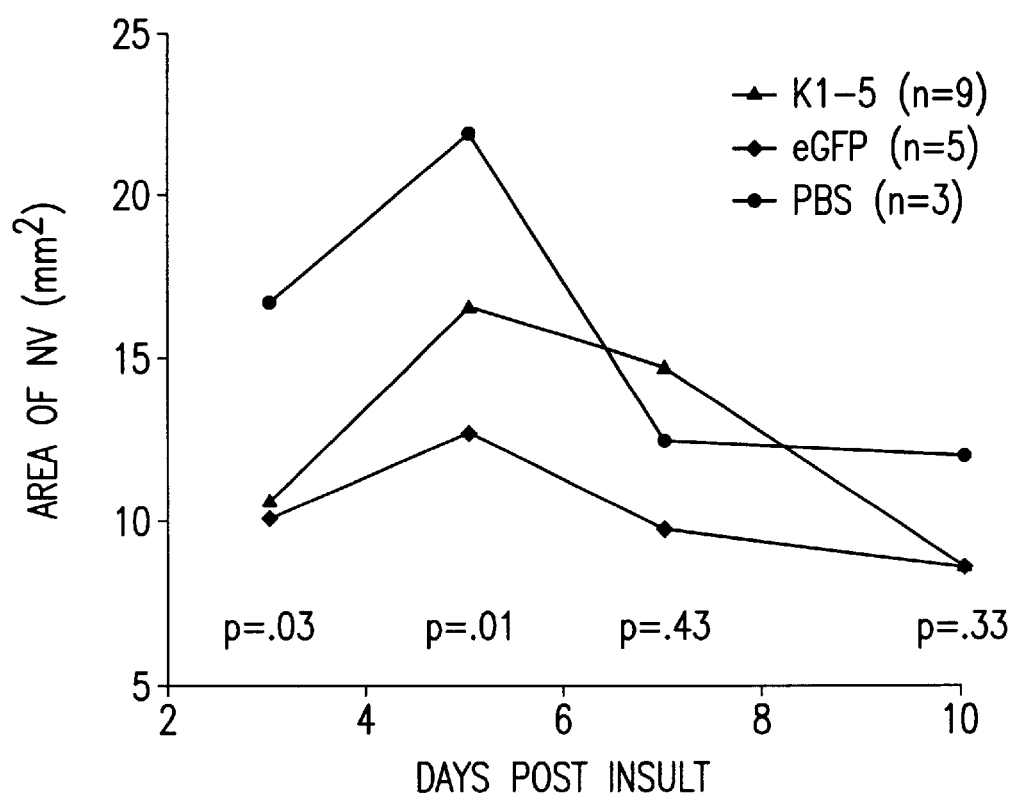
FIG. 36 shows inhibition of neovascularization in animals treated with a lentiviral K1-5 vector. The graph depicts average area of neovascularization in animals treated with PBS (n=3), lentiviral vector carrying the marker eGFP gene (n=5) or lentiviral vector carrying the K1-5 gene (n=9).
Figure 37A:
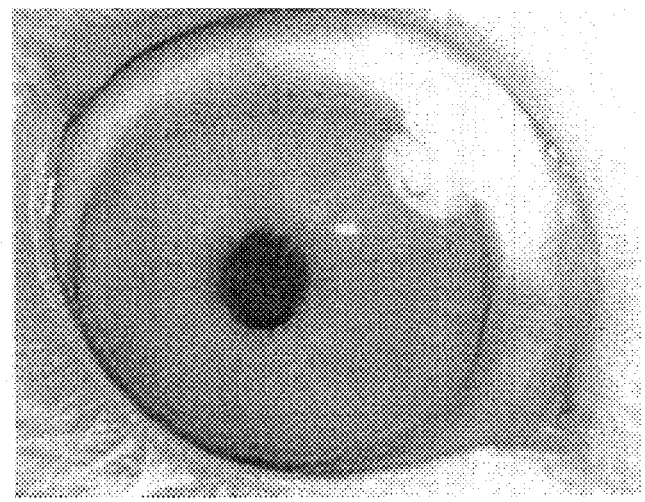
FIG. 37A shows a photograph of normal (nontreated, nonstimulated) cornea.
Figure 37B:
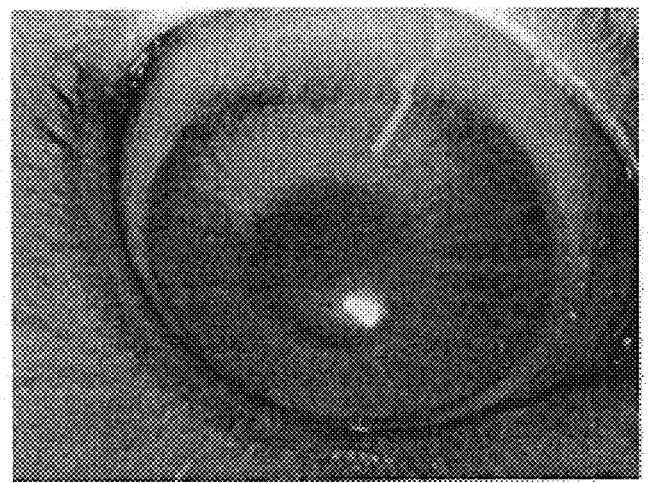
FIG. 37B shows a photograph of an alkali challenged cornea of an animal treated with a Mig/
Figure 37C:
FIG. 37C shows a photograph of an alkali challenged cornea of an animal treated with a control lentiviral vector without a therapeutic anti-angiogenic gene. Note the invasion of blood vessels into the cornea.
Figure 37D:
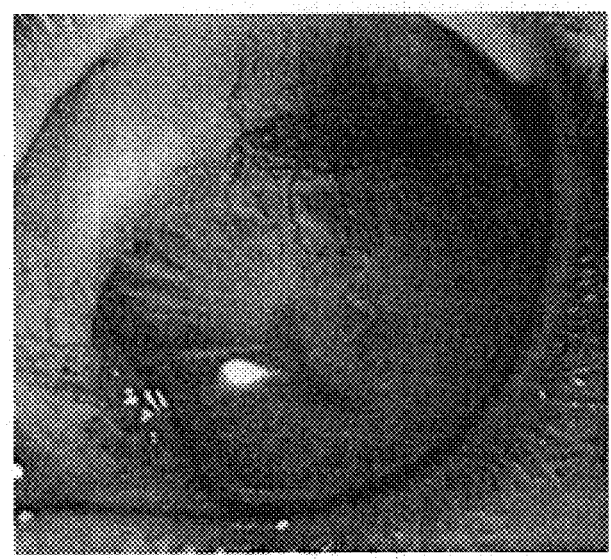
FIG. 37D shows a photograph of an alkali challenged cornea of an untreated animal. Note the invasion of blood vessels into the cornea.

Corneal pocket assay was performed on New Zealand white rabbits to determine the effects of the Kringle 1-5 gene on neovascularization in the eye. Nylon mesh were inserted as spacers into the intrastromal corneal pockets, followed by injection of either a lentiviral vector carrying a Kringle 1-5 gene and a marker gene eGFP (FIG. 26), a lentiviral vector carrying the marker gene eGFP only, or injected with PBS alone. The mesh was removed from the eyes 24 hours later, and sutures were applied to the eyes 7 days later to stimulate neovascularization. The extent of neovascularization was measured at days 3, 5, 7 and 10 after sutures application. Corneas were also harvested for histopathological and transgene expression analysis. As shown in FIG. 36, there was significant inhibition of neovascularization in animals treated with lentiviral vector carrying the Kringle 1-5 gene.

EXAMPLE 10
Inhibition of Neovascularization by the Mig/IP10 Fusion Gene

Mig is the monokine induced by interferon gamma, whereas IP10 is the interferon-alpha inducible protein 10. They have similar structure and function, and they both are chemokines belonging to the CXC family. In human these two protein are 37% identical, and their genes are located adjacent to each other on chromosome 4q21.21. Mig and IP10 bind to CXCR3, a G-protein coupled receptor expressed predominantly on memory and activated T cells. CXCR3 is also found on B cells, NK cells and monocytes. Recently, a second receptor for Mig and IP10 was found on endothelial cells. Functionally, both Mig and IP10 are chemotatic for activated T cells and are thought to effect blood vessel formation by inhibiting endothelial cell chemotaxis as well as growth factor induced angiogenesis. The effects of a Mig/IP10 fusion gene on neovascularization in the eye was examined as described below.

Figure 38:
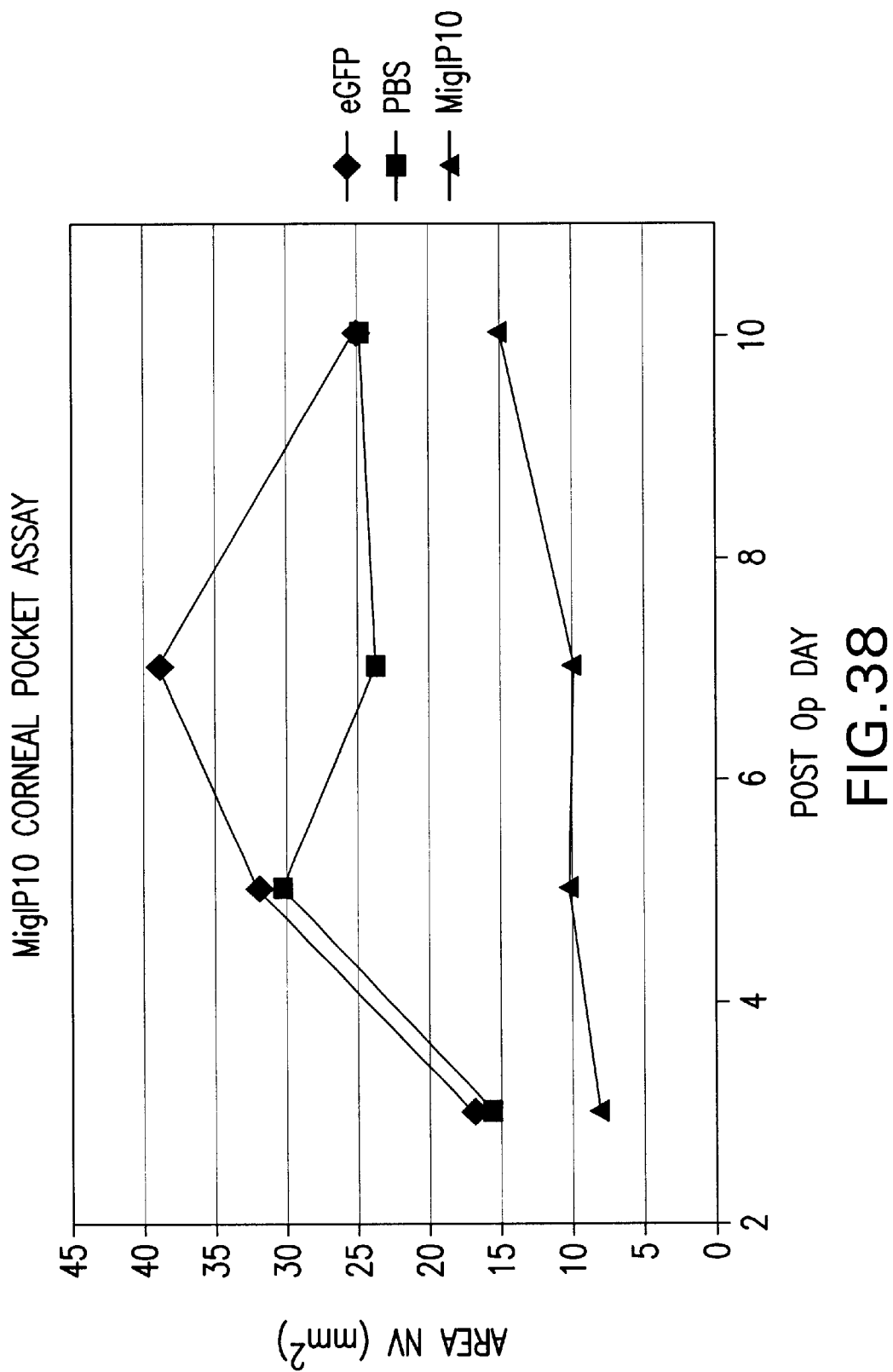
FIG. 38 shows inhibition of neovascularization in animals treated with a Mig/IP10 lentiviral vector. The graph depicts average area of neovascularization in animals treated with PBS, lentiviral vector carrying the marker eGFP gene or lentiviral vector carrying the K1-5 gene.

Corneal intrastromal micropockets were created as described in Example 7, and nylon mesh impregnated with lentivirus carrying the Mig/IP10 fusion gene (FIG. 27), lentiviral vector carrying the marker gene eGFP only, or nylon mesh impregnated with PBS alone were inserted into the micropockets. The mesh was removed after 24 hours. To induce neovascularization, the corneas were exposed to 6 mm Whatman #3 filter disks saturated with 20 µl of 1.0M NaOH. Neovascularization was then measured over a 10 day time course. As shown in FIGS. 37–38, there was significant inhibition of neovascularization in animals treated with lentiviral vector carrying the Mig/IP10 fusion gene.

EXAMPLE 11
Inhibition of Neovascularization by KDR Gene

Figure 39:
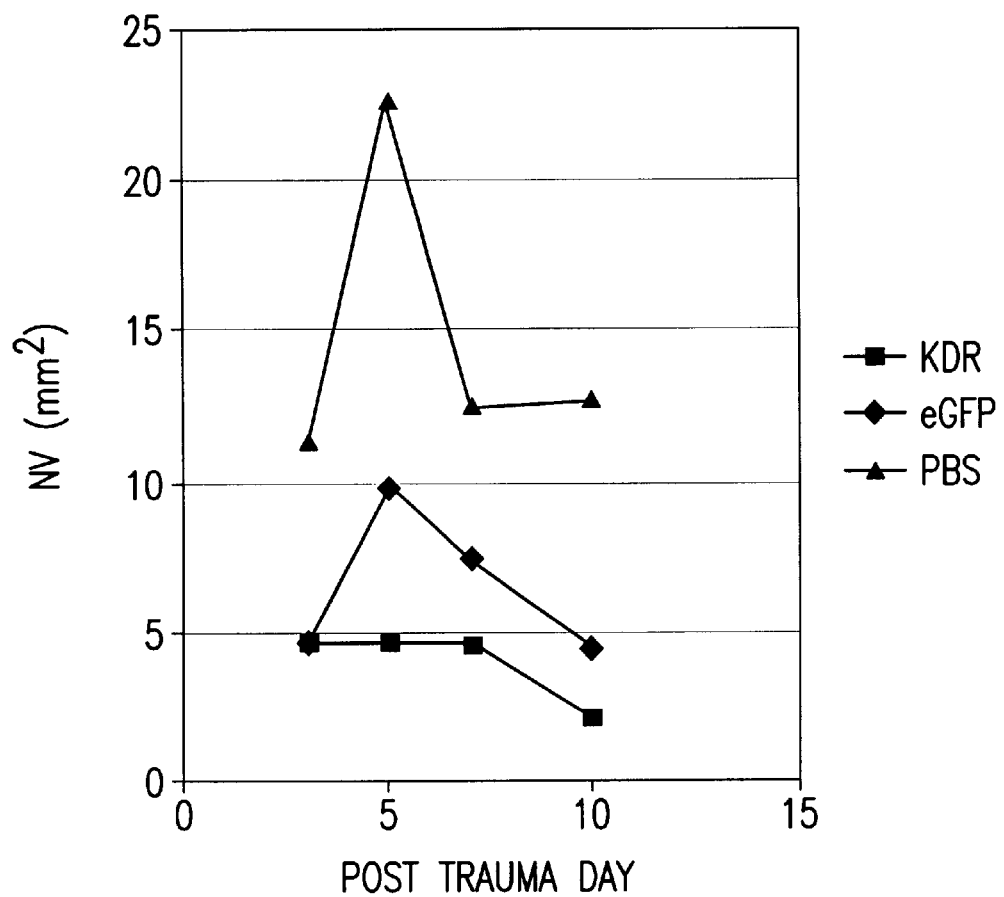
FIG. 39 shows inhibition of neovascularization in animals treated with a lentiviral KDR vector. The graph depicts average area of neovascularization in animals treated with PBS (n=3), lentiviral vector carrying the marker eGFP gene (n=6) or lentiviral vector carrying the KDR gene (n=9).

KDR (kinase insert domain receptor) is a membrane-bound receptor of VEGF (VEGF Receptor 2). VEGF is a potent mitogen for vascular endothelial cells and induces proliferation, migration and protease production. It has been shown that a soluble fragment of KDR (sKDR) has angiostatic properties by way of its antagonist activity against VEGF. The sKDR also binds and blocks the external domain of the membrane-bound KDR. The effects of a sKDR gene delivered by lentiviral vector (FIG. 18) on neovascularization in the eyes were examined in animal model as described above. Results in FIG. 39 show that there was significant inhibition of neovascularization in animals treated with lentiviral vector carrying the sKDR gene.

The following references were cited herein:
Anand-Apte et al., (1996) Biochem. Cell. Biol. 74: 853–862.
Bergers et al., (1999) Science 284: 808–812.
Bigg et al., (1997) J. Biol. Chem. 272: 15496–15500.
Boehm et al., (1997) Nature 390: 404–407.
Brooks et al., (1998) Cell 92: 391–400.
Cao et al., (1997) J. Biol. Chem. 272: 22924–22928.
Chittenden et al., (1995) Nature 374: 733–736.
Docherty et al., (1985) Nature 318: 666–669.
Dole et al., (1996) Cancer Res. 56: 5734–5740.
Ealovega et al., (1996) Cancer Res. 56: 1965–1969.
Gomez et al., (1997) Eur. J. Cell. Biol. 74: 111–122.
Greene et al., (1996) J. Biol. Chem. 271: 30375–30380.
Innes et al., (1999) Exp. Hematol. 27: 75–87.
Ji et al., (1998) Biochem. Biophys. Res. Commun. 247: 414–419.

Kirsch et al., (1998) Cancer Res. 58: 4654–4659.
Kobayashi et al., (1998) Oncogene 16: 1587–1591.
Luster and Leder, (1996) J. Exp. Med. 178: 1057–1065.
Martin et al., (1996) Oncogene 13: 569–576.
Mauceri et al., (1998) Nature 394: 287–291.
Miyake et al., (1999) Br. J. Cancer 79: 1651–1656.
Miyoshi et al., (1997) Proc. Natl. Acad. Sci. USA 94: 10319–10323.
Musso et al., (1997) J. Hepatol. 26: 593–605.
Naldini et al., (1996) Science 272: 263–267.
O'Reilly et al., (1997) Cell 88: 277–85.
Perlman et al., (1999) Gene Ther. 6: 758–763.
Perlman et al., (1998) EMBO 17: 3576–3586.
Saille et al., (1999) Neuroscience 92: 1455–1463.
Sasaki et al., (2000) J Mol Biol. 301(5):1179–90.
Sgadari et al., (1997) Blood 89:2635–2643.
Sgadari et al., (1996) Proc. Natl. Acad. Sci. USA 93: 13791–13796.
Stetler-Stevenson et al., (1990) J. Biol. Chem. 265: 13933–13938.
Tannenbaum et al., (1998) J. Immunol. 161: 927–932.
Valente et al., (1998) Int. J. Cancer 75: 246–253.
Wang et al., (1997) Oncogene 14: 2767–2774.
Zetter (1998) EMBO. J. 17: 1656–1664.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments and specific compounds described herein are representative of preferred embodiments and are not intended as limitations on the scope of the invention. Changes therein will occur to those skilled in the art which are encompassed within the spirit of the invention as defined by the scope of the claims.

What is claimed is:

1. A method of inhibiting intraocular neovascularization in an individual having an age-related macular degeneration, comprising administering to the eye of said individual a pharmacologically effective dose of a lentiviral vector comprising a therapeutic gene that regulates angiogenesis.

2. The method of claim 1, wherein said lentiviral vector is administered in a dosage of from about $10^6$ to $10^9$ transducing particles into the cornea, capsular, vitreal or sub-retinal space.

3. The method of claim 1, wherein said gene that regulates angiogenesis encodes proteins or polypeptides selected from the group consisting of a tissue inhibitor of metalloproteinase, endostatin, angiostatin, endostatin XVIII, endostatin XV, kringle 1–5, PEX, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fins-like tyrosine kinase 1 receptor), and kinase insert domain receptor (KDR).

4. The method of claim 3, wherein said gene that regulates angiogenesis encodes kinase insert domain receptor (KDR).

5. The method of claim 3, wherein said gene that regulates angiogenesis encodes tissue inhibitor of metalloproteinase (TIMP)-1.

6. The method of claim 3, wherein said gene that regulates angiogenesis encodes tissue inhibitor or metalloproteinase (TIMP)-2.

7. The method of claim 3, wherein said gene that regulates angiogenesis encodes tissue inhibitor of metalloproteinase (TIMP)-3.

8. The method of claim 3, wherein said gene that regulates angiogenesis encodes tissue inhibitor of metalloproteinase (TIMP)-4.

9. The method of claim 3, wherein said gene that regulates angiogenesis encodes endostatin.

10. The method of claim 3, wherein said gene that regulates angiogenesis encodes angiostatin.

11. The method of claim 3, wherein said gene that regulates angiogenesis encodes endostatin XVIII.

12. The method of claim 3, wherein said gene that regulates angiogenesis encodes endostatin XV.

13. The method of claim 3, wherein said gene that regulates angiogenesis encodes the C-terminal hemopexin domain of matrix metalloproteinase-2.

14. The method of claim 3, wherein said gene that regulates angiogenesis encodes the kringle 5 domain of human plasminogen.

15. The method of claim 3, wherein said gene that regulates angiogenesis encodes a fusion protein of endostatin and angiostatin.

16. The method of claim 3, wherein said gene that regulates angiogenesis encodes a fusion protein of endostatin and the kringle 5 domain of human plasminogen.

17. The method of claim 3, wherein said gene that regulates angiogenesis encodes the monokine-induced by interferon-gamma (Mig).

18. The method of claim 3, wherein said gene that regulates angiogenesis encodes the interferon-alpha inducible protein 10 (IP10).

19. The method of claim 3, wherein said gene that regulates angiogenesis encodes a fusion protein of Mig and IP10.

20. The method of claim 3, wherein said gene that regulates angiogenesis encodes soluble FLT-1 (fins-like tyrosine kinase 1 receptor).

21. The method of claim 3, wherein the gene that regulates angiogenesis encodes kringle 1–5.

22. The method of claim 3, wherein the gene that regulates angiogenesis encodes PEX.

23. The method of claim 1, wherein the lentiviral vector further expresses a marker gene.

24. The method of claim 23, wherein said marker gene is enhanced green fluorescent protein gene.

25. The method of claim 1, wherein the lentiviral vector comprises an IRES (internal ribosome entry site) element between two cloning sites so that two different proteins are produced from a single transcript.

26. The method of claim 1, wherein the lentiviral vector is selected from the group consisting of pHR-CMV-KDR-ires-eGFP, pHR-CMV-Timp1-ires-eGFP, pHR-EF1/HTLV-Ang-ires-eGFP, pHR-EF1/HTLV-Endo XV-ires-eGFP, pHR-EF1/HTLV-Kringle 1–5-ires-eGEP, pHR-EF1/HTLV-Timp1-ires-eGFP, pHR-EF1/HTLV-Timp4-ires-eGFP and pHR-EF1/HTLV-Endo XVIII-ires-eGFP.

* * * * *

UNITED STATES PATENT AND TRADEMARK OFFICE
CERTIFICATE OF CORRECTION

PATENT NO. : 7,122,181 B2 Page 1 of 1
APPLICATION NO. : 10/245050
DATED : October 17, 2006
INVENTOR(S) : Stout et al.

It is certified that error appears in the above-identified patent and that said Letters Patent is hereby corrected as shown below:

In claim 26, column 28, line 60, delete "eGEP" and insert --eGFP-- therefor.

Signed and Sealed this

Ninth Day of January, 2007

JON W. DUDAS
*Director of the United States Patent and Trademark Office*